US008143248B2

(12) United States Patent
Dubois et al.

(10) Patent No.: US 8,143,248 B2
(45) Date of Patent: Mar. 27, 2012

(54) TRICYCLIC N-HETEROARYL-CARBOXAMIDE DERIVATIVES CONTAINING A BENZIMIDAZOLE UNIT, METHOD FOR PREPARING SAME AND THEIR THERAPEUTIC USE

(75) Inventors: Laurent Dubois, Antony (FR); Yannick Evanno, Antony (FR); Luc Even, Antony (FR); Catherine Gille, Antony (FR); Andre Malanda, Antony (FR); David Machnik, Antony (FR); Nathalie Rakotoarisoa, Antony (FR)

(73) Assignee: Sanofi-Aventis, Paris (FR)

( * ) Notice: Subject to any disclaimer, the term of this patent is extended or adjusted under 35 U.S.C. 154(b) by 734 days.

(21) Appl. No.: 12/184,437

(22) Filed: Aug. 1, 2008

(65) Prior Publication Data

US 2009/0042873 A1    Feb. 12, 2009

Related U.S. Application Data

(63) Continuation of application No. PCT/FR2007/000183, filed on Feb. 1, 2007.

(30) Foreign Application Priority Data

Feb. 3, 2006 (FR) ..................... 06 01007

(51) Int. Cl.
  *A61K 31/535* (2006.01)
(52) U.S. Cl. .................. 514/230.2; 514/292; 514/338; 514/300; 514/267; 546/273.1; 546/113; 546/85; 548/302.4; 544/101; 544/250
(58) Field of Classification Search .................. 514/230, 514/292, 338, 300, 267; 546/273.1, 113, 546/85; 548/302.4; 544/101, 250
See application file for complete search history.

(56) References Cited

FOREIGN PATENT DOCUMENTS

| EP | 1535922 | | 6/2005 |
|---|---|---|---|
| WO | WO 03/037274 | * | 5/2003 |
| WO | WO 2005/028445 | | 3/2005 |
| WO | WO 2005/105798 | | 11/2005 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Database Chemcats, (2006), Database Accession No. 2006:2135904.
Cabranes A. et al., "Decreased endocannabinoid levels in the brain and beneficial effects of agents activating cannabinoid and/or vanilloid receptors in a rat model of multiple sclerosis" Neurobiology of Disease, 20:207-217 (2005).
Cortright D. et al., "Biochemical pharmacology of the vanilloid receptor TRPV1" Eur. J. Biochem., 271:1814-1819 (2004).
Davidson E. et al., "Activity and expression of the vanilloid receptor 1 (TRPV1) is altered by long-term diabetes in epineurial arterioles of the rat sciatic nerve" Diabetes/Metabolism Research and Reviews, 22:211-219 (2006).
Holzer P., "TRPV1 and the gut: from a tasty receptor for a painful vanilloid to a key player in hyperalgesia" European Journal of Pharmacology, 500:231-241 (2004).
Hong S. et al., "Early Painful Diabetic Neuropathy Is Associated with Differential Changes in the Expression and Function of Vanilloid Receptor 1" The Journal of Biological Chemistry, 280(1):618-627 (2005).
Razavi R. et al., "TRPV1 Sensory Neurons Control β Cell Stress and Islet Inflammation in Autoimmune Diabetes" Cell, 127:1123-1135 (2006).
Stein R. et al. "Cool (TRPM8) and Hot (TRPV1) Receptors in the Bladder and Male Genital Tract" The Journal of Urology, 172:1175-1178 (2004).
Yiangou Y. et al.. "Vannilloid receptor 1 immunoreactivity in inflamed human bowel" The Lancet, 357:1338-1339 (2001).

* cited by examiner

*Primary Examiner* — Yong Chu
*Assistant Examiner* — Valerie Rodriguez-Garcia
(74) *Attorney, Agent, or Firm* — Scully, Scott, Murphy & Presser, P.C.

(57) ABSTRACT

The invention concerns tricyclic N-heteroarylcarboxamide derivatives containing a benzimidazole unit of general formula (I):

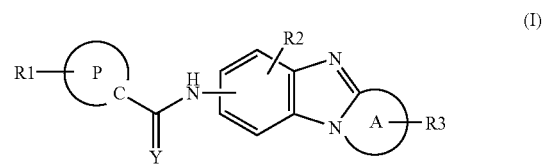

Wherein A, P, Y, $R_1$, $R_2$ and $R_3$ are as defined herein. The invention also concerns a method of preparing the compounds and their therapeutic use.

19 Claims, No Drawings

TRICYCLIC N-HETEROARYL-CARBOXAMIDE DERIVATIVES CONTAINING A BENZIMIDAZOLE UNIT, METHOD FOR PREPARING SAME AND THEIR THERAPEUTIC USE

This application is a continuation of International application No. PCT/FR2007/000,183, filed Feb. 1, 2007, which is incorporated herein by reference in its entirety; which claims the benefit of priority of French Patent Application No. 06/01, 007, filed Feb. 3, 2006.

The invention relates to tricyclic N-heteroarylcarboxamide derivatives containing a benzimidazole unit, to the preparation thereof and to the therapeutic use thereof.

A subject of the invention is compounds derived from tricyclic N-heteroarylcarboxamides containing a benzimidazole unit, which have an antagonist or agonist activity in vitro and in vivo with respect to TRPV1 (or VR1) type receptors.

A subject of the invention is the compounds corresponding to formula (I)

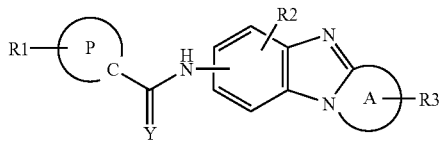

in which:

A is, with the C—N bond of the benzimidazole unit with which it is fused, a 4- to 7-membered monocyclic heterocycle or monocyclic heteroaryl, containing from one to three heteroatoms selected from O, S and N, including the nitrogen atom of the benzimidazole unit;

P is an 8-, 9-, 10- or 11-membered bicyclic hetero-cycle or bicyclic heteroaryl, comprising from 1 to 6 heteroatoms selected from N, O and S; P being linked to the —C(Y)— group by a carbon atom;

with the proviso that, when A is a 7-membered saturated heterocycle, P is other than the 2,3-dihydro-1,4-benzodioxane group, the 1-benzopyran-2-one group and the isoindole group;

$R_1$ is from one to four atoms or groups, which may be identical or different, selected from a hydrogen atom, a halogen atom, and an oxo, thio, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, hetero-arylthio-$C_1$-$C_6$-alkyl, aryl-$C_1$-$C_3$-alkylenethio-$C_1$-$C_6$-alkyl, heteroaryl-$C_1$-$C_3$-alkylenethio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)$NR_4R_5$, nitro, $NR_4R_5$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $SO_2NR_4R_5$, $SF_5$, $NR_6C(O)R_7$, $NR_6SO_2R_8$, $R_4R_5NC(O)$—$C_1$-$C_3$-alkylene, aryl, heteroaryl, aryl-$C_1$-$C_5$-alkylene, heteroaryl-$C_1$-$C_5$-alkylene, aryloxy, arylthio, heteroaryloxy or heteroarylthio group;

said heteroaryl or aryl groups of $R_1$ being optionally substituted with one or more substituents $R_9$, which may be identical to or different from one another;

with the proviso that, when $R_1$ is attached to a nitrogen atom of P, then $R_1$ is different from a halogen atom, and from an oxo, thio, cyano, nitro, $SF_5$, $NR_4R_5$, $C_1$-$C_6$-thioalkyl, thioaryl, thioheteroaryl, $C_1$-$C_6$-alkoxy, aryloxy, heteroaryloxy, —$NR_6COR_7$ and $NR_6SO_2R_8$ group;

Y is an oxygen or sulphur atom;

$R_2$ is a hydrogen atom, a halogen atom, or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl or $C_1$-$C_6$-alkoxy group;

$R_3$ is from one to three atoms or groups, which may be identical or different, selected from a hydrogen atom, a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy or $C_3$-$C_7$-cycloalkyl-$C_1$-$C_3$-alkylenoxy group, when $R_3$ is carried by a carbon atom;

or $R_3$ is from one to two atoms or groups, which may be identical or different, selected from a hydrogen atom, a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)— or heteroaryl-O—C(O)— group, when $R_3$ is carried by a nitrogen atom;

$R_4$ and $R_5$ are, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl group;

or $R_4$ and $R_5$ form, together with the nitrogen atom which carries them, an azetidine, pyrrolidine, piperidine, azepine, morpholine, thiomorpholine, piperazine or homopiperazine group, the $NR_4R_5$ group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cyclo-alkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_1$-$C_6$-fluoroalkyl, aryloxy-$C_1$-$C_6$-alkylene, aryloxy, heteroaryloxy-$C_1$-$C_6$-alkylene or heteroaryloxy group;

$R_6$ and $R_7$ are, independently of one another, a hydrogen atom, or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

or $R_6$ and $R_7$ together form a 4- to 7-membered lactam comprising the nitrogen atom and the C(O) group which carry them;

$R_8$ is a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

or $R_6$ and $R_8$ together form a 4- to 7-membered sultam comprising the nitrogen atom and the S(O)$_2$ group which carry them;

$R_9$ is a halogen atom, or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano, $NR_4R_5$, $R_4R_5N$—$C_1$-$C_3$-alkylene, aryl, heteroaryl, aryloxy, arylthio, heteroaryloxy or heteroarylthio group, said heteroaryl or aryl groups being optionally substituted with one or more substituents selected from a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano, $NR_4R_5$ or $R_4R_5N$—$C_1$-$C_3$-alkylene group.

In the compounds of formula (I):
the sulphur atom(s) of the heterocycle A may be in oxidized form (S(O) or S(O)$_2$);
the nitrogen atom(s) may be in oxidized form (N-oxide).

The compounds of formula (I) may contain one or more asymmetrical carbon atoms. They may therefore exist in the form of enantiomers or of diastereoisomers. These enantiomers and diastereoisomers, and also mixtures thereof, including racemic mixtures, are part of the invention.

The compounds of formula (I) may exist in the form of bases or of addition salts with acids. Such addition salts are part of the invention.

These salts may be prepared with pharmaceutically acceptable acids, but the salts of other acids that can be used, for example, for purifying or isolating the compounds of formula (I) are also part of the invention.

The compounds of formula (I) may also exist in the form of hydrates or of solvates, i.e. in the form of associations or of combinations with one or more molecules of water or with a solvent. Such hydrates and solvates are also part of the invention.

In the context of the present invention, the term:
"a halogen atom" is intended to mean: a fluorine, a chlorine, a bromine or an iodine;
"$C_t$-$C_z$" is intended to mean: a carbon-based chain that may have from t to z carbon atoms where t and z can have the values from 1 to 7; for example, $C_1$-$C_3$ is a carbon-based chain which may have from 1 to 3 carbon atoms;
"an alkyl" is intended to mean: a linear or branched, saturated aliphatic group. By way of examples, mention may be made of methyl, ethyl, propyl, isopropyl, butyl, isobutyl, tert-butyl, pentyl, etc., groups;
"an alkylene" is intended to mean: a linear or branched, saturated divalent alkyl group, for example a $C_{1-3}$-alkylene group is a linear or branched, divalent carbon-based chain having from 1 to 3 carbon atoms, more particularly a methylene, ethylene, 1-methylethylene or propylene;
"a cycloalkyl" is intended to mean: a cyclic alkyl group. By way of examples, mention may be made of cyclopropyl, cyclobutyl, cyclopentyl, cyclohexyl, etc., groups;
"a fluoroalkyl" is intended to mean: an alkyl group of which one or more of the hydrogen atoms have been substituted with a fluorine atom;
"an alkoxy" is intended to mean: an —O-alkyl radical where the alkyl group is as defined above;
"a fluoroalkoxy" is intended to mean: an alkoxy group of which one or more hydrogen atoms have been substituted with a fluorine atom;
"a thioalkyl or alkylthio" is intended to mean: an —S-alkyl radical where the alkyl group is as defined above;
"an aryl" is intended to mean: a monocyclic or bicyclic aromatic group containing between 6 and 10 carbon atoms. By way of examples of aryl groups, mention may be made of phenyl or naphthyl groups;
"a heterocycle" is intended to mean: a 5- to 17-membered, saturated or partially unsaturated, mono-cyclic, bicyclic or tricyclic group containing from 1 to 8 heteroatoms selected from O, S and N.

By way of examples of a monocyclic heterocycle, mention may be made of azetidinyl, pyrrolidinyl, piperidinyl, azepinyl, morpholinyl, thiomorpholinyl, piperazinyl, homopiperazinyl, dihydrooxazolyl, dihydrothiazolyl, dihydroimidazolyl, dihydropyrrolyl or tetrahydropyridinyl groups;

by way of examples of a bicyclic heterocycle, mention may be made of indolinyl, isoindolinyl, dihydrobenzofuranyl, dihydrobenzothiophenyl, dihydrobenzoxazolinyl, dihydroisobenzofuranyl, dihydrobenzimidazolyl, dihydroisobenzothiazolyl, dihydroquinolinyl, tetrahydro-quinolinyl, dihydroisoquinolinyl, tetrahydroiso-quinolinyl, dihydrobenzoxazinyl, benzothiazinyl, dihydrobenzothiazinyl, dihydroquinazolinyl, tetrahydro-quinazolinyl, dihydroquinoxalinyl, tetrahydro-quinoxalinyl, dihydrophthalazinyl, tetrahydrophthalazinyl, tetrahydrobenzazepinyl, tetrahydro-benzo[1,4]diazepinyl, tetrahydrobenzo[1,4]oxazepinyl or tetrahydrobenzo[1,4]thiazepinyl groups;

by way of examples of a tricyclic heterocycle, mention may be made of dihydroimidazo[1,2-a]benzimidazolyl, dihydropyrrolo[1,2-a]benzimidazolyl, tetrahydropyrido-[1,2-a]benzimidazolyl, dihydrothiazolo[1,2-a]-benzimidazolyl, tetrahydropyrimido[1,2-a]benzimidazolyl, tetrahydrodiazepino[1,3][1,2-a]benzimidazolyl, dihydrooxazino[1,4][4,3-a]benzimidazolyl or tetrahydropyrazino[1,2-a]benzimidazolyl groups;

"a heteroaryl" is intended to mean: a 5- to 14-membered aromatic monocyclic, bicyclic or tricyclic group containing from 1 to 8 heteroatoms selected from O, S and N.

By way of examples of a monocyclic heteroaryl, mention may be made of imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl and triazinyl groups;

by way of examples of a bicyclic heteroaryl, mention may be made of indolyl, isoindolyl, benzofuranyl, benzothiophenyl, benzoxazolyl, benzimidazolyl, indazolyl, benzothiazolyl, isobenzofuranyl, isobenzothiazolyl, pyrrolo[2,3-c]pyridinyl, pyrrolo[2,3-b]pyridinyl, pyrrolo[3,2-b]pyridinyl, pyrrolo[3,2-c]pyridinyl, quinolinyl, isoquinolinyl, cinnolinyl, quinazolinyl or quinoxalinyl groups;

by way of examples of a tricyclic heteroaryl, mention may be made of pyrido[1,2-a]benzimidazolyl, thiazolo[1,2-a]-benzimidazolyl, imidazo[1,2-a]benzimidazolyl, pyrimido[1,2-a]benzimidazolyl or pyrazino[1,2-a]-benzimidazolyl groups;

"oxo" signifies "=O";
"thio" signifies "=S".

Among the compounds of the invention, a first group of compounds comprises the compounds of formula (II)

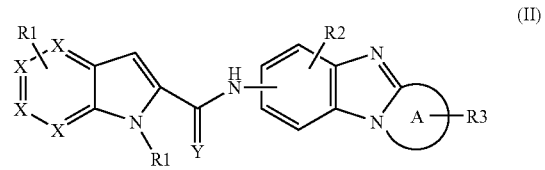

(II)

in which:
X is a carbon atom or a nitrogen atom; said X being identical to or different from one another and the number of X=N not being greater than 2;
$R_1$, $R_2$, $R_3$, Y and A being as defined in formula (I), it being possible for $R_1$ to be linked to the 6-element or 5-element unit of the bicycle.

Among the compounds of the invention, a second group of compounds comprises the compounds of formula (III)

(III)

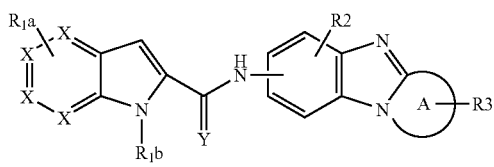

in which:
R$_{1a}$ is one or more atoms or groups, which may be identical or different, selected from a hydrogen atom, a halogen atom or a C$_1$-C$_6$-alkyl, C$_1$-C$_6$-fluoroalkyl, C$_1$-C$_6$-alkoxy, C$_1$-C$_6$-thioalkyl, C$_1$-C$_6$-alkyl-S(O)$_2$—, NR$_4$R$_5$ or nitro group;
R$_{1b}$ is a hydrogen atom, or a C$_1$-C$_6$-alkyl, heteroaryloxy-C$_1$-C$_6$-alkyl, aryl-C$_1$-C$_3$-alkylenoxy-C$_1$-C$_6$-alkyl, R$_4$R$_5$NC(O)—C$_1$-C$_3$-alkylene, aryl, heteroaryl, aryl-C$_1$-C$_6$-alkylene or heteroaryl-C$_1$-C$_6$-alkylene group;
said heteroaryl or aryl groups of R$_{1b}$ being optionally substituted with one or more substituents R$_9$, which may be identical to or different from one another;
R$_9$ is a halogen atom or a C$_1$-C$_6$-alkyl, C$_1$-C$_6$-alkoxy, C$_1$-C$_6$-fluoroalkyl, aryl, heteroaryl, NR$_4$R$_5$ or arylthio group, said heteroaryl or aryl groups being optionally substituted with one or more substituents selected from a halogen atom, and a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_1$-C$_6$-fluoroalkoxy, nitro, cyano or R$_4$R$_5$N—C$_1$-C$_3$-alkylene group;
R$_2$, R$_3$, R$_4$, R$_5$, A, X and Y being as defined in formula (II).

Among the compounds of the invention, a third group of compounds comprises the compounds of formula (IV):

(IV)

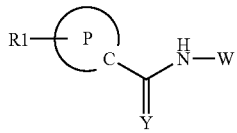

in which W is a tricyclic heterocycle or a tricyclic heteroaryl selected from:

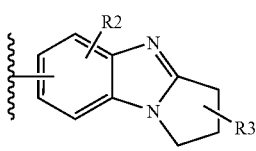

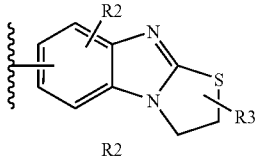

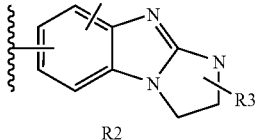

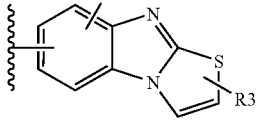

-continued

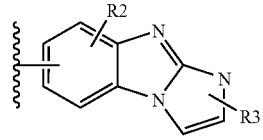

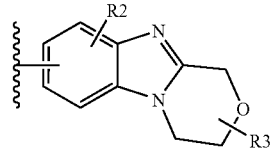

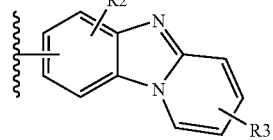

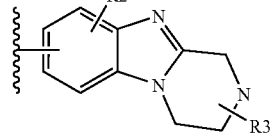

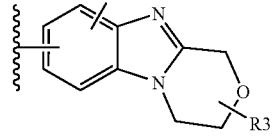

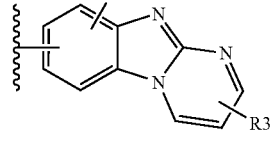

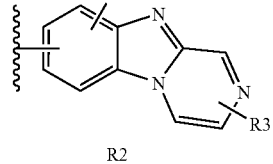

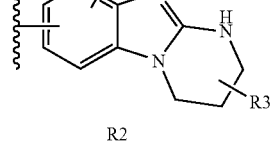

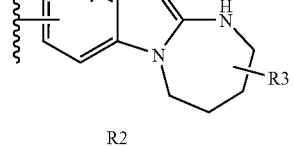

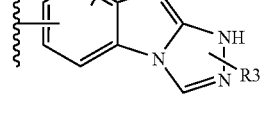

R$_1$, R$_2$, R$_3$, P and Y being as defined in formula (I).
Among the compounds of the invention, a fourth group of compounds comprises the compounds of formula (V)

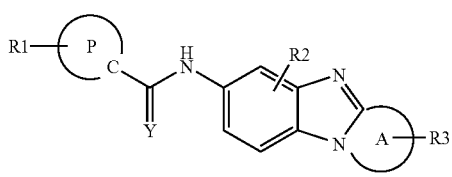

in which:

R₁, R₂, R₃, A and P are as defined in formula (I).

Among the compounds of the invention, a fifth group of compounds comprises the compounds of formula (V) in which:

$R_2$ is a hydrogen atom, or a $C_1$-$C_6$-alkyl or $C_1$-$C_6$-alkoxy group;

$R_3$ is from one to three atoms or groups, which may be identical or different, selected from a hydrogen atom, and a $C_1$-$C_6$-alkyl, $C_1$-$C_6$-alkoxy or hydroxyl group, when $R_3$ is carried by a carbon atom;

or $R_3$ is from one to two atoms or groups, which may be identical or different, selected from a hydrogen atom, and a $C_1$-$C_6$-alkyl, $C_1$-$C_6$-alkyl-O—C(O)— or aryl-$C_1$-$C_3$-alkyl-O—C(O)— group, when $R_3$ is carried by a nitrogen atom;

$R_1$, A and P being as defined in formula (I).

Among the compounds of the invention, a sixth group of compounds comprises the compounds of formula (V) in which:

A is, with the C—N bond of the benzimidazole unit with which it is fused, a 5- to 7-membered monocyclic heterocycle or monocyclic heteroaryl containing from one to three heteroatoms selected from O, S and N, including the nitrogen atom of the benzimidazole unit;

$R_1$, $R_2$, $R_3$ and P being as defined in formula (I).

Among the compounds of the invention, a seventh group of compounds comprises the compounds of formula (Va) in which:

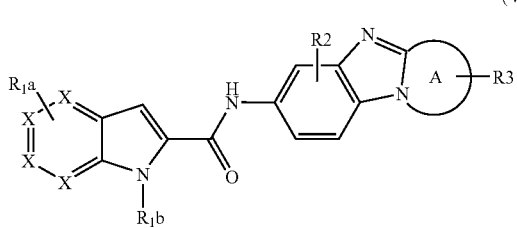

A is, with the C—N bond of the benzimidazole unit with which it is fused, a 5- to 7-membered monocyclic heterocycle or monocyclic heteroaryl containing one or two heteroatoms selected from O, S and N, including the nitrogen atom of the benzimidazole unit;

X is a carbon atom or a nitrogen atom; said X being identical to or different from one another and the number of X=N not being greater than 1;

$R_{1a}$ is one or more atoms or groups, which may be identical or different, selected from a hydrogen atom, a halogen atom, more particularly fluorine, bromine or chlorine, or a $C_1$-$C_6$-alkyl group, more particularly methyl, ethyl, isopropyl or tert-butyl, a $C_1$-$C_6$-fluoroalkyl group, more particularly trifluoromethyl, a $C_1$-$C_6$-alkoxy group, more particularly methoxy, a $C_1$-$C_6$-thioalkyl group, more particularly SCH₃, a $C_1$-$C_6$-alkyl-S(O)₂— group, more particularly —SO₂CH₃, an NR₄R₅ group or a nitro group;

$R_{1b}$ is a hydrogen atom, or a $C_1$-$C_6$-alkyl, more particularly methyl, heteroaryloxy-$C_1$-$C_6$-alkyl, more particularly pyridinyloxyethyl, aryl-$C_1$-$C_3$-alkylenoxy-$C_1$-$C_6$-alkyl, more particularly benzyloxyethyl, R₄R₅NC(O)—$C_1$-$C_3$-alkylene, more particularly R₄R₅NC(O)CH₂—, aryl, more particularly phenyl, heteroaryl, more particularly pyridinyl, aryl-$C_1$-$C_6$-alkylene, more particularly benzyl or naphthylmethyl, phenylethyl, phenylpropyl, or heteroaryl-$C_1$-$C_6$-alkylene, more particularly pyridinylmethyl, pyridinylethyl, pyridinylpropyl, thiazolylmethyl, pyrimidinylmethyl, quinolinylmethyl, quinoxalinylmethyl, furanylmethyl, pyrazinylmethyl or benzothiazolylmethyl group;

said heteroaryl or aryl groups of $R_{1b}$ being optionally substituted with one or more substituents R₉, which may be identical to or different from one another;

$R_2$ is a hydrogen atom;

$R_3$ is an atom or group selected from a hydrogen atom, a $C_1$-$C_6$-alkyl group, more particularly methyl, a $C_1$-$C_6$-alkoxy group, more particularly methoxy, or a hydroxyl group, when $R_3$ is carried by a carbon atom;

or $R_3$ is an atom or group selected from a hydrogen atom, a $C_1$-$C_6$-alkyl group, more particularly methyl, and a $C_1$-$C_6$-alkyl-O—C(O)— group, more particularly (CH₃)₃C—O—C(O)—, when $R_3$ is carried by a nitrogen atom;

R₄ and R₅ are, independently of one another, a $C_1$-$C_6$-alkyl group, more particularly methyl or ethyl;

or R₄ and R₅ form, together with the nitrogen atom which carries them, a pyrrolidine or morpholine group;

R₉ is a halogen atom, more particularly fluorine or chlorine, or a $C_1$-$C_6$-alkyl, more particularly methyl, $C_1$-$C_6$-alkoxy, more particularly methoxy, $C_1$-$C_6$-fluoroalkyl, more particularly trifluoromethyl, aryl, more particularly phenyl, heteroaryl, more particularly imidazolyl, NR₄R₅, or arylthio, more particularly phenylthio, group, said aryl groups being optionally substituted with one or more $C_1$-$C_6$-alkyl groups, more particularly methyl.

Among the compounds of the invention, an eighth group of compounds comprises the compounds of formula (I) in which at the same time $R_1$ and/or $R_2$ and/or $R_3$, and/or A, and/or P and/or Y are as defined in the groups above.

Among the compounds of the invention, a ninth group of compounds comprises the compounds of formula (I')

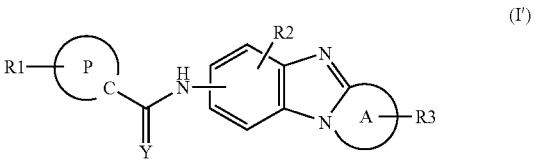

in which

A is, with the C—N bond of the benzimidazole unit with which it is fused, a 4- to 7-membered monocyclic heterocycle or monocyclic heteroaryl containing from 1 to 3 heteroatoms chosen from O, S and N, including the nitrogen atom of the benzimidazole unit;

P is an 8-, 9-, 10- or 11-membered bicyclic hetero-cycle or bicyclic heteroaryl containing from 1 to 6 heteroatoms selected from N, O and S;

with the proviso that, when A is a 7-membered saturated heterocycle, P is different from the 2,3-dihydro-1,4-benzodioxane group and from the 1-benzopyran-2-one group;

$R_1$ is from 1 to 4 atoms or groups, which may be identical or different, selected from a hydrogen atom, a halogen atom, and an oxo, thio, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, $C(O)NR_4R_5$, nitro, $NR_4R_5$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-$S(O)_2$—, $C_1$-$C_6$-fluoroalkyl-$S(O)_2$—, $C_3$-$C_7$-cycloalkyl-$S(O)_2$—, $C_3$-$C_7$-cycloalkyl-$C_1$-$C_3$-alkylene-$S(O)_2$—, $SO_2NR_4R_5$, $NR_6C(O)R_7$, $NR_6SO_2R_8$, $R_4R_5NC(O)$—$C_1$-$C_3$-alkylene, aryl, heteroaryl, aryl-$C_1$-$C_5$-alkylene, heteroaryl-$C_1$-$C_5$-alkylene, aryloxy, arylthio, heteroaryloxy or heteroarylthio group, said heteroaryl or aryl groups being optionally substituted with one or more substituents selected from a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano, $NR_4R_5$ or $R_4R_5N$—$C_1$-$C_3$-alkylene group;

with the proviso that, when $R_1$ is attached to a nitrogen atom of P, then $R_1$ is different from a halogen atom, and from an oxo, thio, cyano, nitro, $NR_4R_5$, $C_1$-$C_6$-thioalkyl, thioaryl, thioheteroaryl, $C_1$-$C_6$-alkoxy, aryloxy, heteroaryloxy, —$NR_6COR_7$ and —$NR_6SO_2R_8$ group;

Y is an oxygen or sulphur atom;

$R_2$ is a hydrogen atom, a halogen atom, or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl or $C_1$-$C_6$-alkoxy group;

$R_3$ is from 1 to 3 atoms or groups, which may be identical or different, selected from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_3$-alkylenoxy, when $R_3$ is carried by a carbon atom;

or is from 1 to 2 atoms or groups, which may be identical or different, selected from a hydrogen atom, a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-$S(O)_2$—, $C_1$-$C_6$-alkyl-$S(O)_2$—, $C_1$-$C_6$-fluoroalkyl-$S(O)_2$—, $C_3$-$C_7$-cyclo-alkyl-$S(O)_2$—, $C_3$-$C_7$-cycloalkyl-$C_1$-$C_3$-alkylene-$S(O)_2$—, $C_1$-$C_6$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)— or heteroaryl-O—C(O)— group, when $R_3$ is carried by a nitrogen atom;

$R_4$ and $R_5$ are, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl group;

or $R_4$ and $R_5$ form, together with the nitrogen atom which carries them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-$S(O)_2$—, $C_1$-$C_6$-alkyl-$S(O)_2$—, $C_1$-$C_6$-fluoroalkyl-$S(O)_2$—, $C_3$-$C_7$-cycloalkyl-$S(O)_2$—, $C_3$-$C_7$-cycloalkyl-$C_1$-$C_3$-alkylene-$S(O)_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)— or $C_1$-$C_6$-fluoroalkyl-C(O)— group;

$R_6$ and $R_7$ are, independently of one another, a hydrogen atom, or a $C_1$-$C_6$-alkyl, $C_3$-$C_7$-cycloalkyl, $C_3$-$C_7$-cycloalkyl-$C_1$-$C_3$-alkylene-, aryl-$C_1$-$C_6$-alkylene- or aryl group;

$R_8$ is a $C_1$-$C_6$-alkyl, $C_3$-$C_7$-cycloalkyl, $C_3$-$C_7$-cycloalkyl-$C_1$-$C_3$-alkylene-, aryl-$C_1$-$C_6$-alkylene- or aryl group.

Among the compounds of the invention, a tenth group of compounds comprises the compounds of formula (II') in which

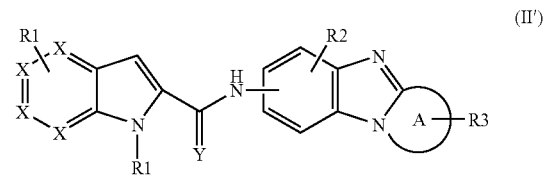

in which

X is a carbon atom or a nitrogen atom; said X being identical to or different from one another and the number of X=N not being greater than 2;

$R_1$, $R_2$, $R_3$, Y and A being as defined in formula (I); it being possible for $R_1$ to be linked to the 5- or 6-element unit of the bicycle.

Among the compounds of the invention, an eleventh group of compounds comprises the compounds of formula (III')

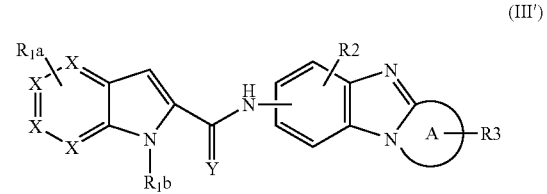

in which $R_{1a}$ is one or more atoms or groups, which may be identical or different, selected from a hydrogen atom, a halogen atom or a $C_1$-$C_6$-fluoroalkyl group;

$R_{1b}$ is a hydrogen atom, or a $C_1$-$C_6$-alkyl, aryl, hetero-aryl, aryl-$C_1$-$C_6$-alkylene- or heteroaryl-$C_1$-$C_6$-alkylene- group, said groups being optionally substituted with one or more groups or atoms, which may be identical or different, selected from a halogen atom or a $C_1$-$C_6$-alkyl group;

$R_2$, $R_3$, A, X and Y being as defined in formula (II).

Among the compounds of the invention, a twelfth group of compounds comprises the compounds of formula (IV'):

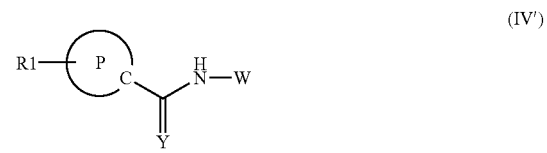

in which W is a tricyclic heterocycle or a tricyclic heteroaryl selected from:

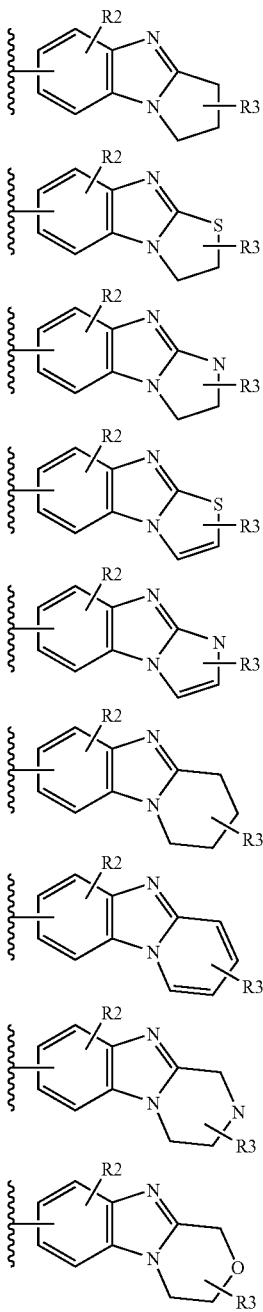

$R_1$, $R_2$, $R_3$, P and Y being as defined in formula (I).

Among the compounds of the invention, a thirteenth group of compounds comprises the compounds of formula (V'),

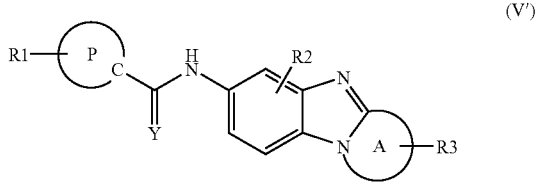

in which
$R_1$, $R_2$, $R_3$, A, P and Y are as defined in formula (I).

Among the compounds of the invention, a fourteenth group of compounds comprises the compounds of formula (V') in which
$R_2$ and $R_3$ are, independently of one another, a hydrogen atom or a $C_1$-$C_6$-alkyl group;
$R_1$, A, P and Y being as defined in formula (I).

Among the compounds of the invention, a fifteenth group of compounds comprises the compounds of formula (I) in which at the same time $R_1$ and/or $R_2$ and/or $R_3$, and/or A, and/or P and/or Y are as defined in the groups 9 to 14 above.

In the subsequent text, the term "leaving group" is intended to mean a group that can be readily cleaved from a molecule through the breaking of a heterolytic bond, with the departure of a pair of electrons. This group can thus be readily replaced with another group during a substitution reaction, for example. Such leaving groups are, for example, halogens or an activated hydroxyl group such as a methanesulphonate, benzenesulphonate, p-toluenesulphonate, triflate, acetate, etc. Examples of leaving groups and also references for the preparation thereof are given in "Advances in Organic Chemistry", J. March, 5th Edition, Wiley Interscience, 2001.

In the subsequent text, the term "protective group" is intended to mean a group that can be momentarily incorporated into a chemical structure with the aim of temporarily inactivating a part of the molecule during a reaction, and that can be readily removed at a subsequent step of the synthesis. Examples of protective groups and also references regarding their properties are given in T. W. Greene, P. G. M. Wutz, 3rd Edition, Wiley Interscience 1999.

In accordance with the invention, the compounds of formula (I) can be prepared according to the process illustrated by general scheme 1 which follows:

Scheme 1

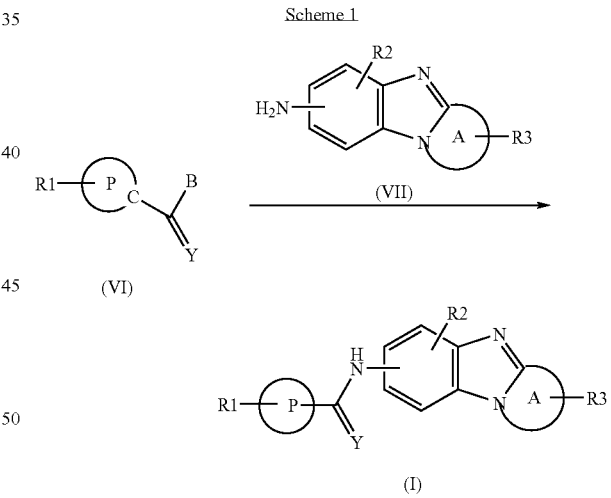

The compounds (I) can be obtained by reaction of a compound of formula (VI) in which B is a $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy group, and P, Y and $R_1$ are as defined in formula (I), with an amide of the compound of formula (VII), in which A, $R_2$ and $R_3$ are as defined in formula (I) above, at the reflux of a solvent such as toluene. The aluminum amide of the compound of formula (VII) is prepared by the prior action of trimethylaluminum on the amines of formula (VII).

Starting from compounds of formula (VI), in which B is a hydroxyl group, and P, Y and $R_1$ are as defined in formula (I), the carboxylic acid function can be converted beforehand to an acid halide such as an acid chloride by the action, for example, of thionyl chloride, at the reflux of a solvent such as dichloromethane or dichloroethane. The compound of formula (I) is then obtained by reaction of the compounds of formula (VI), in which B is a chlorine atom, and P, Y and $R_1$ are as defined in formula (I), with the compound of formula (VII), in which A, $R_2$ and $R_3$ are as defined in formula (I) above, in the presence of a base such as triethylamine or sodium carbonate.

Alternatively, the compounds of formula (VI), in which B is a hydroxyl group, and P, Y and $R_1$ are as defined in formula (I), can be coupled with the compounds of formula (VII) in the presence of a coupling agent such as a dialkylcarbodiimide, [(benzotriazol-1-yl)oxy][tris(pyrrolidino)]phosphonium hexafluorophosphate, diethylcyanophosphonate or any other coupling agent known to those skilled in the art, in the presence of a base such as triethylamine, in a solvent such as, for example, dimethylformamide.

In scheme 1, the compounds of formulae (VI) and (VII) and the other reagents, when the method of preparing them is not described, are commercially available, described in the literature, or prepared by analogy to processes described in the literature (R. S. Begunov et al., *Russian J. Org. Chem.*, 2004, 40(11), 1740-1742; V. M. Reddy et al., *J. Indian Chem. Soc.*, 1984, (111), 89-91; K. V. B. Rao et al., *Eur. J. Med. Chem.*, 1981, 16(1), 35-38; R. J. North et al., *J. Het. Chem.*, 1969, 6, 655; A. R. Freedman et al., *J. Het. Chem.*, 1966, 3(3), 257; Mullock, E. B. *J. Chem. Soc. Section C*, 1970, (6), 829-833), for example.

The compounds of formula (VI) or (I), that are C-substituted on an aryl or heteroaryl group with an alkyl group, can be obtained by a coupling reaction, catalyzed by a metal such as palladium or iron, carried out on the corresponding compounds of formula (VI) or (I), substituted with a halogen atom, such as a chlorine, in the presence, for example, of an alkylmagnesium halide or of an alkylzinc halide, according to the methods described in the literature (A. Furstner et al., *J. Am. Chem. Soc.*, 2002, 124(46), 13856; G. Quéguiner et al., *J. Org. Chem.*, 1998, 63(9), 2892), for example, or known to those skilled in the art.

The compounds of formula (VI) or (I), that are C-substituted on an aryl or heteroaryl group with a cyano, aryl or heteroaryl group, can be obtained by a coupling reaction, catalyzed by a metal such as palladium, carried out on the corresponding compounds of formula (VI) or (I), substituted, for example, with a bromine atom, in the presence of trimethylsilyl cyanide, of arylboronic acid or of heteroarylboronic acid, or by any other method described in the literature or known to those skilled in the art.

The compounds of formula (VI) or (I), in which P is N-substituted with a substituent $R_1$ corresponding to an aryl or heteroaryl group, can be obtained by a coupling reaction, catalyzed by a metal such as copper, carried out on the corresponding amines of formula (VI) or (I), in the presence of an aryl halide or a heteroaryl halide, according to the Buchwald method (S. L. Buchwald et al., *J. Am. Chem. Soc.*, 2002, 124, 11684), or by any other method described in the literature or known to those skilled in the art.

The compounds of formula (I) or (VI), that are C-substituted on an aryl or heteroaryl group with an $NR_4R_5$, $NR_6COR_7$ or $NR_6SO_2R_8$ group, can be obtained from the corresponding compounds of formula (I) or (VI), substituted, for example, with a bromine atom, by a coupling reaction respectively with an amine, an amide or a sulphonamide in the presence of a base, of a phosphine and of a palladium-based catalyst, according to methods described in the literature or known to those skilled in the art.

The compounds of formula (I) or (VI), that are substituted with a $C(O)NR_4R_5$ group, can be obtained from the corresponding compounds of formula (I) or (VI), substituted with a cyano group, according to methods described in the literature or known to those skilled in the art.

The compounds of formula (I) or (VI), that are substituted with an —S(O)-alkyl or —S(O)$_2$-alkyl group, can be obtained by oxidation of the corresponding compounds of formula (VI) or (I), substituted with a thioalkyl group, according to methods described in the literature or known to those skilled in the art.

The compounds of formula (VI) or (I), that are substituted with an $NR_4R_5$, $NR_6COR_7$ or $NR_6SO_2R_8$ group, can be obtained from the corresponding compounds of formula (VI) or (I), substituted with a nitro group, for example by reduction, then acylation or sulphonylation, according to methods described in the literature or known to those skilled in the art.

The compounds of formula (VI) or (I), that are substituted with an $SO_2NR_4R_5$ group, can be obtained by a method similar to that described in *Pharmazie*, 1990, 45, 346, or according to methods described in the literature or known to those skilled in the art.

The compounds of formula (I) or (VI) in which Y is a sulphur atom can, for example, be obtained by reaction of the corresponding compounds of formula (I) or (VI) in which Y is an oxygen atom, with a reagent such as Lawesson's reagent.

The compounds of formula (I) for which $R_3$ corresponds to a protective group carried by a nitrogen, such as an ethoxycarbonyl group, a tert-butyloxycarbonyl group or a benzyloxycarbonyl group, can be deprotected, according to chemical methods known to those skilled in the art, so as to give compounds of formula (I) where $R_3$ is a hydrogen atom.

A subject of the invention, according to another of its aspects, is also the compounds of formula (VII-x) with x ranging from a to n. These compounds can be used as synthesis intermediates of the compounds of formula (I).

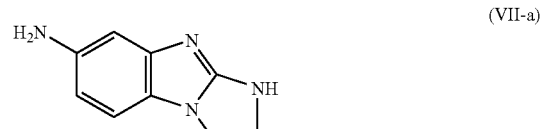

(VII-a)

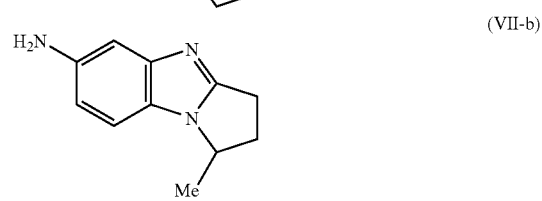

(VII-b)

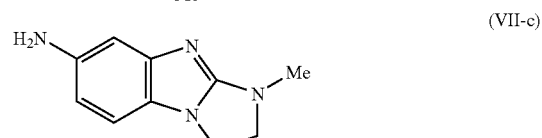

(VII-c)

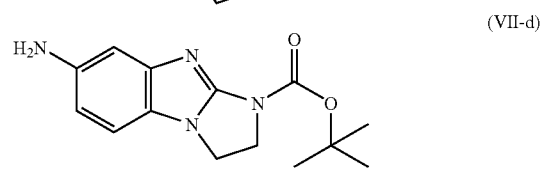

(VII-d)

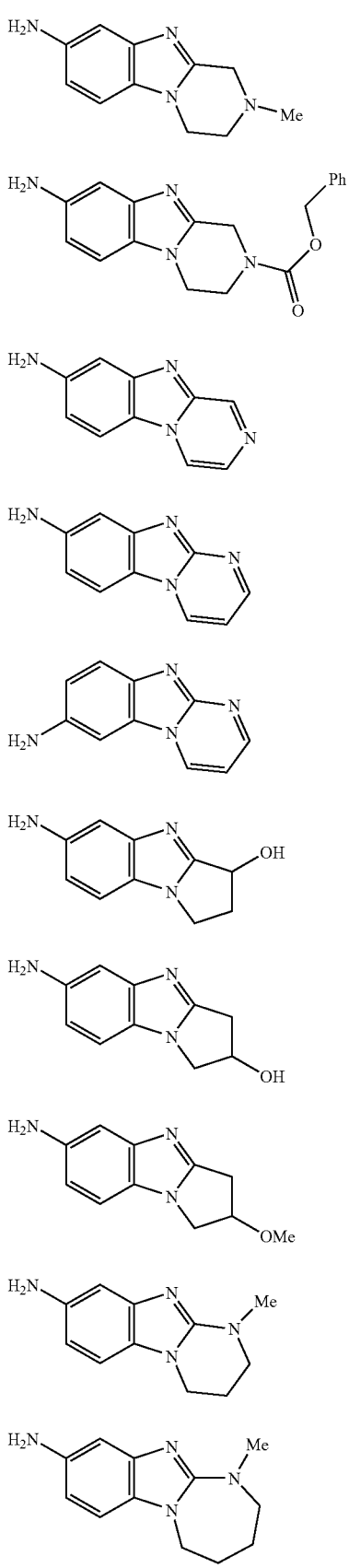

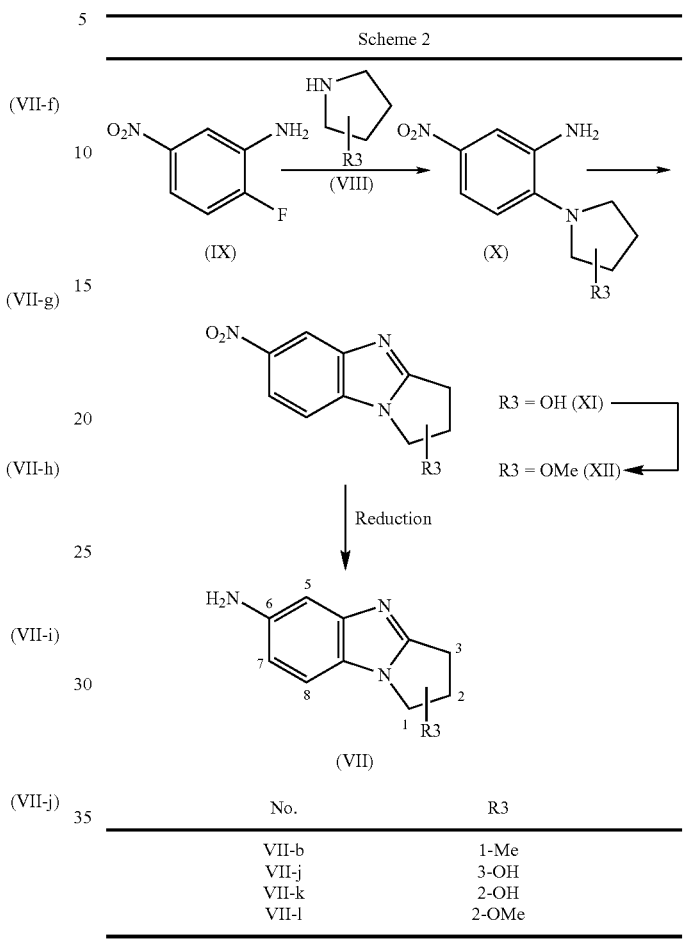

The amines (VII-b), (VII-j), (VII-k) and (VII-l) can be prepared according to scheme 2 hereinafter:

| No. | R3 |
|---|---|
| VII-b | 1-Me |
| VII-j | 3-OH |
| VII-k | 2-OH |
| VII-l | 2-OMe |

A process for preparing the amines (VII-b), (VII-j), (VII-k) and (VII-l), in their racemic forms, is summarized in scheme 2. It consists, in a first step, in substituting 2-fluoro-5-nitroaniline (IX) with the racemic amine (VIII). This reaction is carried out, for example, by heating the two reagents without solvent. The addition products (X) thus obtained are subsequently cyclized to heterocycles (XI) in the presence of a reagent such as trifluoroacetic acid and of a reagent such as hydrogen peroxide, the reaction being carried out in solution in a solvent such as dichloromethane (by optimization of a process described in A. R. Freedman et al., *J. Het. Chem.*, 1966, 3(3), 257). In the case where $R_3$ is different from a hydrogen atom, the cyclization can give a mixture of regioisomers.

The compound (XI) ($R_3$=hydroxyl) can be converted to the compound (XII) with $R_3$=methoxy, for example by alkylation in the presence of a base such as sodium hydride and of an alkylating agent such as methyl iodide or dimethyl sulphate. The nitro group of the compound (XI) or (XII) is subsequently reduced to give the amines (VII-b), (VII-j), (VII-k) or (VII-l), by catalytic hydrogenation in the presence of a catalyst such as palladium-on-charcoal, or by any other method of reduction of a nitro group to an amine, known to those skilled in the art.

The amines (VII-e) and (VII-f) can be prepared according to scheme 3 hereinafter:

Scheme 3

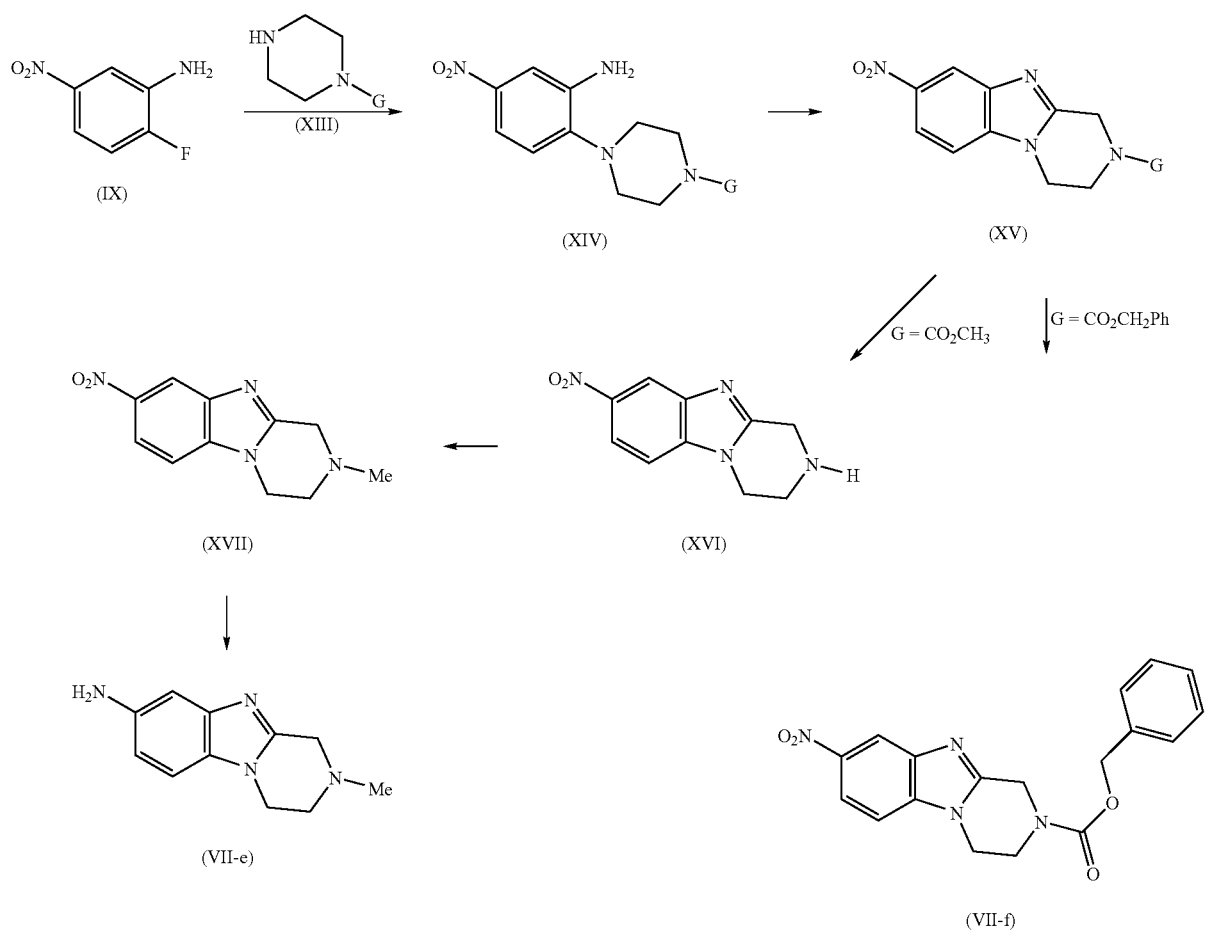

A process for preparing the amines (VII-e) and (VII-f) consists, in a first step, in substituting 2-fluoro-5-nitroaniline (IX) with piperazine (XIII), which is substituted on one of the nitrogens with a protective group G. This reaction is carried out, for example, by heating the two reagents without solvent. The addition product (XIV) thus obtained is subsequently cyclized to a heterocyclic compound (XV) in the presence of a reagent such as trifluoroacetic acid or formic acid and of a reagent such as hydrogen peroxide, the reaction being carried out in solution in a solvent such as dichloromethane. The heterocyclic compound (XV) can then be deprotected; for example, if G=CO$_2$CH$_3$, the hydrolysis of (XV) in the presence of an acid such as hydrochloric acid gives the amine (XVI) which can be alkylated, for example in the presence of a base such as sodium hydride and of an alkylating agent such as methyl iodide, in a solvent such as tetrahydrofuran or dimethylformamide, to give the heterocycle (XVII). The nitro group of the compound (XVII) is subsequently reduced to give the amine (VII-e) by catalytic hydrogenation in the presence of a catalyst such as palladium-on-charcoal, or by any other method of reduction of a nitro group to an amine, known to those skilled in the art. The amine (VII-f) is prepared by reducing the nitro group of the compound (XV), for example if G=CO$_2$CH$_2$Ph, by reaction with a reagent such as tin chloride, in a solvent such as dimethylformamide.

The amines (VII-a), (VII-c) and (VII-d) can be prepared according to scheme 4 hereinafter:

Scheme 4

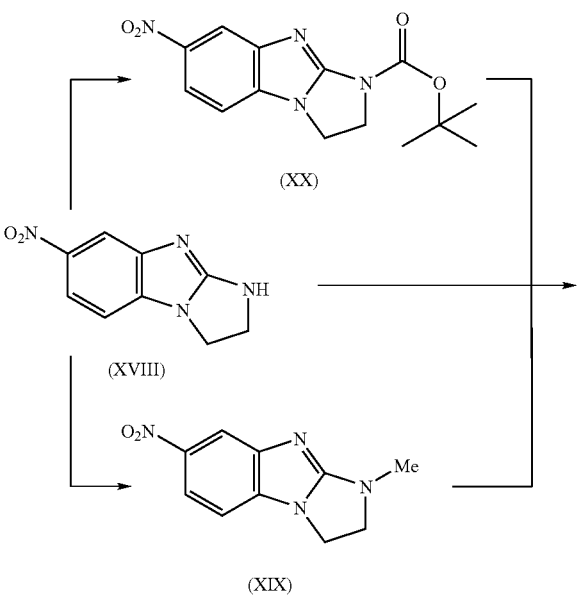

G = H:(VII-a)
G = Me:(VII-c)
G = CO₂tBu:(VII-d)

The amine (VII-a) can be prepared by reduction of a corresponding nitro precursor (XVIII), described in the literature (R. J. North et al., *J. Het. Chem.*, 1969, 6, 655), for example, by catalytic hydrogenation in the presence of a catalyst such as palladium-on-charcoal, or according to any other method of reduction of a nitro group to an amine, known to those skilled in the art.

The amine (VII-c) can be prepared in two steps from the nitro precursor (XVIII) described above. The intermediate (XIX) is prepared from the precursor (XVIII), using a base such as sodium hydride and an alkylating agent such as methyl iodide, in a solvent such as tetrahydrofuran or dimethylformamide. The compound (XIX) thus obtained can subsequently be converted to an amine (VII-c) by catalytic hydrogenation in the presence of a catalyst such as palladium-on-charcoal, or by any other method of reduction of a nitro group to an amine, known to those skilled in the art.

The amine (VII-d) can be prepared in two steps from the nitro precursor (XVIII) described above. The intermediate (XX) is prepared from the precursor (XVIII), using a base such as sodium hydride and di-tert-butyl dicarbonate. The compound (XX) thus obtained can subsequently be converted to an amine (VII-d) by catalytic hydrogenation in the presence of a catalyst such as palladium-on-charcoal, or by any other method of reduction of a nitro group to an amine, known to those skilled in the art.

The amine (VII-g) can be prepared according to scheme 5 hereinafter:

Scheme 5

(XXI)

(XXIII)

(VII-g)

The amine (VII-g) can be prepared in two steps from 2-iodo-4-nitrochlorobenzene (XXI) (G. A. Olah, *J. Org. Chem.*, 1993 (58), 3194-3195). Firstly, the compound (XXI) reacts with aminopyrazine (XXII) in the presence of a catalyst such as palladium diacetate, of a phosphine and of a base such as cesium carbonate, in a solvent such as toluene. Under these conditions, the cyclization product (XXIII) is isolated and can finally give the amine (VII-g) by catalytic hydrogenation in the presence of a catalyst such as palladium-on-charcoal, or according to any other method of reduction of a nitro group to an amine, known to those skilled in the art.

The amines (VII-h) and (VII-i) can be prepared according to scheme 6 hereinafter:

Scheme 6

(XXIV)

(XXV)

(XXVI)

(VII-h)

(VII-i)

The condensation of 2-amino-5-nitrobenzimidazole (XXIV) with a reagent such as diacetal (XXV) makes it possible to isolate a cyclization product (XXVI), which is a mixture of two isomers. The nitro group of the hetero-cycle (XXVI) can be reduced to an amine group by reaction with tin chloride, or according to any other method of reduction of a nitro group to an amine, known to those skilled in the art. The amines (VII-h) and (VII-i) are thus obtained.

The amines (VII-m) and (VII-n) can be prepared according to scheme 7 hereinafter:

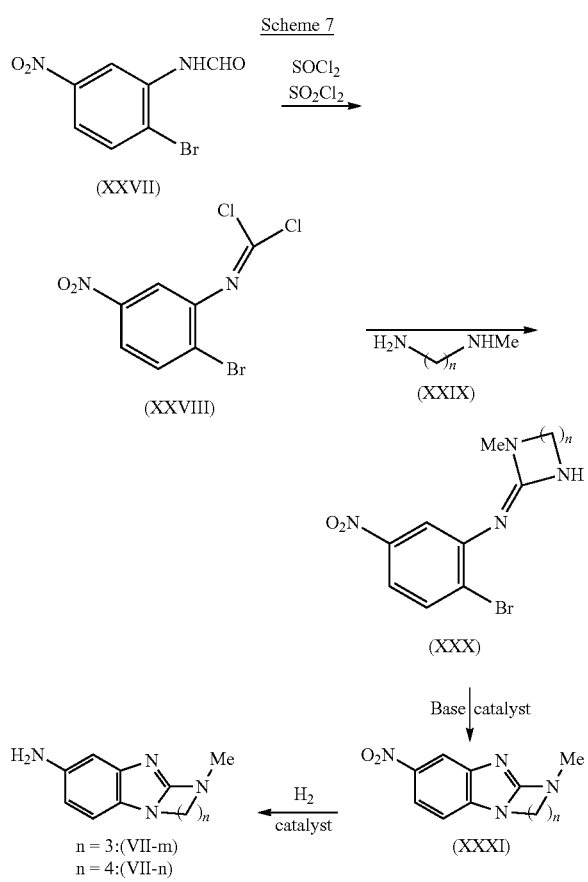

Scheme 7

The amines (VII-m) and (VII-n) can be prepared in four steps from formamide (XXVII) (S. L. Chupak, US2006135447). The formamide (XXVII) can be activated in the form of dichloroimine (XXVIII) by reaction with a mixture of $SOCl_2$ and $SO_2Cl_2$. The compound (XXVIII) can subsequently be substituted with a diamine of structure (XXIX), in which n=3 or 4, to give a compound of structure (XXX). The latter can subsequently be converted to a tricyclic benzimidazole (XXXI) in the presence of a catalyst such as palladium diacetate, of a phosphine and of a base such as cesium carbonate. Reduction of the nitro group of (XXXI) by catalytic hydrogenation in the presence of a catalyst such as palladium-on-charcoal, or according to any other method of reduction of a nitro group to an amine, known to those skilled in the art, makes it possible to obtain the amine (VII-m) or (VII-n).

The table which follows illustrates the chemical structures and the physical properties of some examples of intermediate compounds of formula (VII) according to the invention.

In this table:

the column "Mp (° C.)" gives the melting points of the products in degrees Celsius (° C.), failing this "NMR" indicates that the NMR spectrum is described in the examples;

in the "salt/base" column, "-" represents a compound in free base form, whereas "HCl" represents a compound in hydrochloride form and the ratio between brackets is the (acid:base) ratio.

TABLE 1

| No. | structure | Salt/Base | Mp (° C.) |
| --- | --- | --- | --- |
| VII-a | 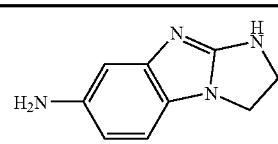 | — | 235-236 |
| VII-b | 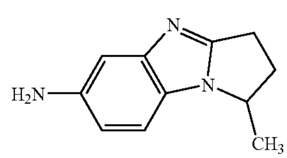 | — | 168-172 |
| VII-c | 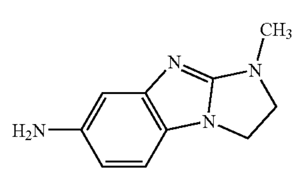 | — | 195-190 |
| VII-d | 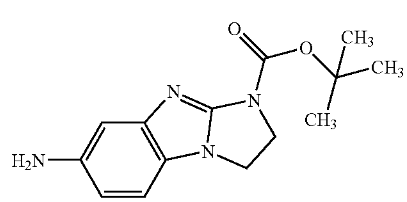 | — | 198-200 |

TABLE 1-continued

| No. | structure | Salt/Base | Mp (° C.) |
|---|---|---|---|
| VII-e | 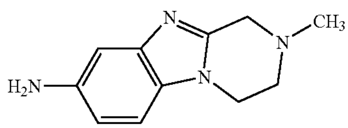 | — | NMR (Example V) |
| VII-f | 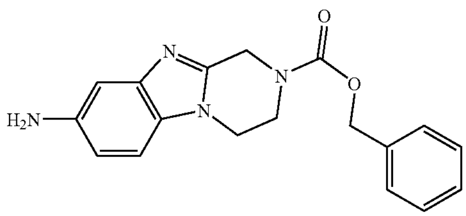 | — | 115-118 |
| VII-g | 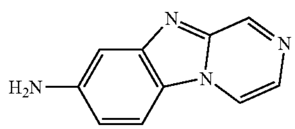 | — | 249-253 |
| VII-h | 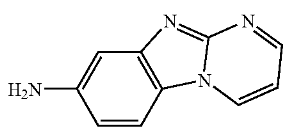 | — | NMR (Example VIII-2) |
| VII-i | 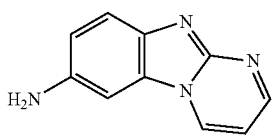 | — | NMR (Example VIII-3) |
| VII-j | 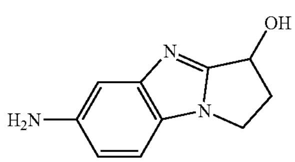 | — | NMR (Example X-3) |
| VII-k | 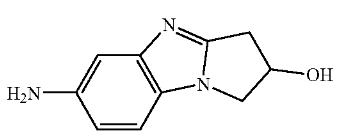 | HCl (1:1) | NMR (Example X-4) |
| VII-l | 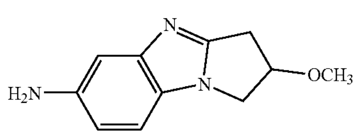 | — | 140-142 |
| VII-m | 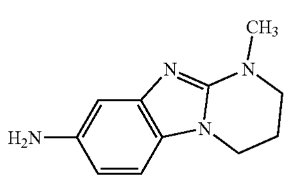 | HCl (1:1) | 335-340 |
| VII-n | 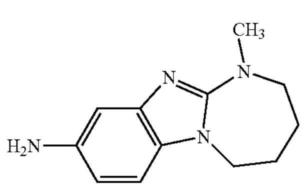 | HCl (2:1) | 330-336 |

The following examples describe the preparation of some intermediate compounds of formula (VII) in accordance with the invention. The numbers of the compounds exemplified refer to those in Table 1. The elemental microanalyses, the LC-MS (liquid chromatography-mass spectrometry) analyses, or the IR or NMR spectra confirm the structures of the compounds obtained.

EXAMPLE I

Compound No. VII-a

6-amino-2,3-dihydro-1H-imidazo[1,2-a]benzimidazole 1 g of palladium-on-charcoal at 10% is added, under argon, to a vigorously stirred solution of 2.7 g (13.22 mmol) of 2,3-dihydro-6-nitro-1H-imidazo[1,2-a]-benzimidazole (R. J. North et al., *J. Het. Chem.*, 1969, 6, 655) in 100 ml of methanol. 15 g (0.23 mol) of ammonium formate are added to the reaction mixture and the suspension is subsequently stirred for 12 h. A solid is recovered by filtration and is purified by silica column chromatography (eluent: dichloromethane-methanol). 0.82 g of the expected product is obtained in the form of a grey solid after drying under reduced pressure.

Melting point (base): 235-236° C.

$^1$H NMR (DMSO D$_6$), δ (ppm): 3.89 (m, 4H); 4.38 (m, 2H); 6.18 (dxd, 1H); 6.46 (d, 1H); 6.58 (s, 1H); 6.73 (d, 1H).

EXAMPLE II

Compound No. VII-b

6-amino-2,3-dihydro-1-methyl-1H-pyrrolo[1,2-a]-benzimidazole

II-1 2-(2-methylpyrrolidin-1-yl)-5-nitroaniline 5 g (32.03 mmol) of 2-fluoro-5-nitroaniline and 4.9 ml (48.04 mmol) of 2-methylpyrrolidine (racemic) are placed in a screw reactor. The reactor is closed and the mixture is heated at 100° C. for 5 h. After cooling, the mixture is taken up with 100 ml of water and 100 ml of dichloromethane. The organic phase is separated, washed with 50 ml of a saturated solution of sodium chloride, dried over magnesium sulphate and then concentrated under reduced pressure. The resulting product is used as it is in the subsequent reaction.

II-2 2,3-dihydro-1-methyl-6-nitro-1H-pyrrolo[1,2-a]-benzimidazole 2 ml (22.6 mmol) of a 35% aqueous solution of hydrogen peroxide are added, dropwise, to a solution of 1 g (4.52 mmol) of 2-(2-methylpyrrolidin-1-yl)-5-nitro-aniline, obtained in the preceding step, and 4 ml (51.92 mmol) of trifluoroacetic acid in 20 ml of dichloromethane. The mixture is refluxed for 30 min and then cooled and taken up in 100 ml of dichloromethane and 100 ml of a saturated aqueous solution of sodium hydrogen carbonate. The organic phase is separated, washed with 50 ml of a saturated solution of sodium chloride, dried over magnesium sulphate and then concentrated under reduced pressure. The resulting orange oil (0.89 g) is used as it is in the subsequent reaction.

II-3 6-amino-2,3-dihydro-1-methyl-1H-pyrrolo[1,2-a]-benzimidazole (VIIb)

A mixture of 0.25 g (1.15 mmol) of 2,3-dihydro-1-methyl-6-nitro-1H-pyrrolo[1,2-a]benzimidazole, obtained in the preceding step, and 10 mg of palladium-on-charcoal at 10%, in suspension in 15 ml of ethanol and 1 ml of a 1N aqueous solution of hydrochloric acid, is stirred for four hours at ambient temperature under 4 bar of hydrogen. After this period of time, the mixture is filtered, concentrated under reduced pressure, and taken up with 100 ml of dichloromethane and 100 ml of a 30% aqueous solution of sodium hydroxide. The organic phase is separated, washed with 50 ml of a saturated solution of sodium chloride, dried over magnesium sulphate and then concentrated under reduced pressure. The resulting solid is purified by silica column chromatography (eluent: dichloromethane-methanol). 0.133 g of the expected product is obtained in the form of a beige solid after drying under reduced pressure.

Melting point (base): 168-172° C.

$^1$H NMR (DMSO D$_6$), δ (ppm): 1.49 (d, 3H); 2.16 (m, 1H); 2.75 (m, 1H); 2.9 (m, 2H); 3.2 (m, 2H); 4.41 (sext., 1H); 6.51 (dxd, 1H); 6.92 (d, 1H); 7.08 (d, 1H).

EXAMPLE III

6-amino-2,3-dihydro-3-methyl-1H-imidazo-1,2-a]benzimidazole (Compound No. VII-c)

III-1 2,3-dihydro-3-methyl-6-nitro-1H-imidazo[1,2-a]-benzimidazole (Compound XIX)

0.1 g (0.49 mmol) of 2,3-dihydro-6-nitro-1H-imidazo[1,2-a]benzimidazole (R. J. North et al., *J. Het. Chem.*, 1969, 6, 655) in 10 ml of tetrahydrofuran is added, under argon, to a suspension, stirred at 20° C., of 0.023 g (0.59 mmol) of sodium hydride at 60% in 5 ml of tetrahydrofuran. After stirring at 20° C. for 45 minutes, 30 μl (0.54 mmol) of iodomethane are added and the mixture is then stirred at 20° C. for 12 hours. After this period of time, the reaction mixture is poured into 100 ml of water and then extracted with three times 30 ml of dichloromethane. The organic phases are combined, dried over sodium sulphate, and then concentrated under reduced pressure. 0.1 g of the expected product (XIX) is thus obtained in the form of a yellow solid which will be used as it is in the subsequent synthesis.

Melting point (base): 208-209° C.

III-2 6-amino-2,3-dihydro-3-methyl-1H-imidazo[1,2-a]-benzimidazole (Compound No. VII-c)

0.5 g of palladium-on-charcoal at 10% is added, under argon, to a vigorously stirred solution of 0.81 g (3.71 mmol) of compound (XIX), prepared in the preceding step, in 70 ml of methanol. 10 g (0.153 mol) of ammonium formate are added to the reaction mixture and the suspension is subsequently stirred for 12 h. A solid is collected by filtration and is purified by silica column chromatography (eluent: dichloromethane-methanol). 0.26 g of the expected product is obtained in the form of a grey solid after drying under reduced pressure.

Melting point (base): 185-190° C.

$^1$H NMR (DMSO D$_6$), δ (ppm): 2.84 (s, 3H); 3.76 (m, 2H); 3.91 (m, 2H); 4.41 (s, NH$_2$); 6.19 (dxd, 1H); 6.48 (d, 1H); 7.71 (d, 1H).

EXAMPLE IV 6-amino-2,3-dihydro-3-tert-butoxycarbonyl-1H-imidazo[1,2-a]benzimidazole Compound No. VII-d

IV-1 6-nitro-2,3-dihydro-3-tert-butoxycarbonyl-1H-imidazo[1,2-a]benzimidazole (Compound No. XX)

13.9 g (57.86 mmol) of 2,3-dihydro-6-nitro-1H-imidazo[1,2-a]benzimidazole (R. J. North et al., *J. Het. Chem.*, 1969, 6, 655) are added, in several steps, to a suspension, stirred at 20° C. under argon, of 3.47 g (86.8 mmol) of sodium hydride at 60% in 482 ml of tetrahydrofuran. After stirring at 20° C. for 2 hours, 15.1 ml (65.73 mmol) of di-tert-butyl dicarbonate are added and the mixture is then stirred for 1 h 30 at 20° C. After this period of time, the reaction mixture is poured into 50 ml of water. A precipitate is collected by filtration and is dried under reduced pressure. 14.31 g of the expected product (XX) are thus obtained in the form of a yellow solid that will be used as it is in the subsequent synthesis.

Melting point (base): 222-224° C.

IV-2 6-amino-2,3-dihydro-3-tert-butoxycarbonyl-1H-imidazo[1,2-a]benzimidazole (Compound No. VII-d)

A suspension of 0.1 g (0.33 mmol) of compound (XX) and 0.5 g of palladium-on-charcoal at 10% in 150 ml of ethanol is stirred at 20° C. under 5 bar of hydrogen for four hours. After removal of the insoluble material by filtration, the resulting ethanolic solution is concentrated under reduced pressure. 70 mg of the expected product are thus obtained in the form of a white solid.

Melting point (base): 198-200° C.

$^1$H NMR (CDCl$_3$), δ (ppm): 1.51 (s, 9H); 2.25-3.55 (broad peak, NH$_2$); 4.01 (m, 2H); 4.32 (m, 2H); 6.48 (dxd, 1H); 6.83 (d, 1H); 6.91 (d, 1H)

EXAMPLE V 7-amino-3-methyl-1,2,3,4-tetrahydropyrazino-[1,2-a]benzimidazole (Compound No. VII-e)

V-1 2-[4-(ethoxycarbonyl)pyrazin-1-yl]-5-nitroaniline (Compound No. XIV, G=CO$_2$Et)

A mixture of 10 g (64.06 mmol) of 2-fluoro-5-nitroaniline and 20.08 ml (137.72 mmol) of N-(ethoxy-carbonyl)piperazine is heated at 140° C. for 12 h. After this period of time, the mixture is concentrated under reduced pressure and then 5 ml of acetic acid are added. A precipitate is collected by filtration and is washed with water and then dried under reduced pressure. 18.5 g of the expected product are thus isolated in the form of a yellow solid.

$^1$H NMR (DMSO D$_6$), δ (ppm): 1.15 (t, 3H); 2.82 (m, 4H); 3.51 (m, 4H); 4.02 (q, 2H); 5.35 (s, NH$_2$); 6.95 (d, 1H); 7.38 (dxd, 1H); 7.5 (d, 1H).

V-2 3-ethoxycarbonyl-7-nitro-1,2,3,4-tetrahydropyrazino[1,2a]benzimidazole (Compound No. XV, G=CO$_2$Et)

15 ml (169.5 mmol) of an aqueous solution of hydrogen peroxide at 35% are added, dropwise, to a solution of 17 g (57.76 mmol) of the compound (XIV) obtained in the preceding step, and of 60 ml (51.92 mmol) of formic acid. The mixture is heated for one hour at 50° C. and then cooled, concentrated under reduced pressure, and taken up in 200 ml of dichloromethane and 300 ml of a saturated aqueous solution of potassium bicarbonate. The organic phase is separated, washed with 100 ml of a saturated solution of sodium chloride, dried over sodium sulphate and then concentrated under reduced pressure. The resulting foam is purified by silica column chromatography, elution being carried out with a mixture of dichloromethane and methanol. 3.9 g of the expected compound are thus isolated in the form of a solid that will be used as it is in the subsequent synthesis.

V-3 7-nitro-1,2,3,4-tetrahydropyrazino[1,2-a]-benzimidazole (Compound No. XVI)

A solution of 3.9 g (13.44 mmol) of compound (XV), obtained in the preceding step, in 100 ml of 6N hydrochloric acid is refluxed for 12 hours. After this period of time, the cooled solution is brought to pH>9 by successive additions of concentrated sodium hydroxide, and then extracted three times with 100 ml of dichloromethane. The organic phases are combined, washed with 150 ml of water, dried over sodium sulphate and then concentrated under reduced pressure. The resulting product is purified by silica column chromatography, elution being carried out with a mixture of dichloromethane and methanol. 0.3 g of the expected compound is thus isolated in the form of a solid that will be used as it is in the subsequent synthesis.

$^1$H NMR (CDCl$_3$), δ (ppm): 1.91 (1 broad peak, NH); 5.56 (m, 2H); 4.28 (m, 2H); 4.48 (s, 2H); 7.5 (d, 1H); 8.31 (dxd, 1H); 8.72 (d, 1H).

V-4 3-methyl-7-nitro-1,2,3,4-tetrahydropyrazino-[1,2-a]benzimidazole (Compound No. XVII)

0.3 g (1.37 mmol) of compound (XVI), obtained in the preceding step, in 20 μl (1.65 mmol) of iodomethane is added, under argon, to a suspension, stirred at 20° C., of 0.07 g (1.65 mmol) of sodium hydride at 60% in 15 ml of tetrahydrofuran, and then the mixture is stirred at 20° C. for 12 hours. After this period of time, the reaction mixture is poured into 100 ml of water and then extracted with three times 30 ml of dichloromethane. The organic phases are combined, dried over sodium sulphate, and then concentrated under reduced pressure. 0.13 g of the expected product (XVII) is thus obtained and will be used as it is in the subsequent synthesis.

$^1$H NMR (CDCl$_3$), δ (ppm): 2.49 (s, 3H); 2.93 (m, 2H); 3.82 (s, 2H); 4.11 (m, 2H); 7.29 (d, 1H); 8.09 (dxd, 1H); 8.49 (d, 1H).

V-5 7-amino-3-methyl-1,2,3,4-tetrahydropyrazino-[1,2-a]benzimidazole (Compound No. VII-e)

A suspension of 0.13 g (0.56 mmol) of compound (XVII) obtained in the preceding step, of 0.2 g of palladium-on-charcoal at 10% and of 5 g (79.36 mmol) of ammonium formate is stirred at 20° C. for 12 hours. After removal of the insoluble material by filtration, the filtrate is concentrated under reduced pressure. 80 mg of the expected product are thus obtained in the form of an oil.

$^1$H NMR (CDCl$_3$), δ (ppm): 2.48 (s, 3H); 2.89 (m, 2H); 3.75 (s, 2H); 3.85 (broad peak, NH$_2$); 3.97 (m, 2H); 6.57 (dxd, 1H); 6.91 (d, 1H); 7 (d, 1H).

EXAMPLE VI 7-amino-3-benzyloxycarbonyl-1,2,3,4-tetra-hydropyrazino[1,2-a]benzimidazole (Compound No. VII-f)

VI-1 2-[4-(benzyloxycarbonyl)pyrazin-1-yl]-5-nitroaniline (Compound No. XIV, G=CO$_2$CH$_2$Ph)

A mixture of 9.44 g (60.5 mmol) of 2-fluoro-5-nitroaniline and 24.98 ml (130.08 mmol) of N-(benzyloxy-carbonyl)piperazine is heated at 140° C. for 12 h. After this period of time, the mixture is taken up in 200 ml of dichloromethane. The organic phase is successively washed with a saturated aqueous solution of potassium carbonate, and three times with 50 ml of water, and is then dried over magnesium sulphate and concentrated under reduced pressure. The residue obtained is purified by silica column chromatography, elution being carried out with a mixture of dichloromethane and ethyl acetate. 8.6 g of the expected product are thus isolated.
$^1$H NMR (CDCl$_3$), δ (ppm): 2.91 (m, 4H); 3.68 (m, 4H); 4.16 (s, NH$_2$); 5.18 (s, 2H); 6.92 (d, 1H); 7.35 (m, 5H); 7.6 (m, 2H).

VI-2 3-benzyloxycarbonyl-7-nitro-1,2,3,4-tetrahydro-pyrazino[1,2-a]benzimidazole (Compound No. XV, G=CO$_2$CH$_2$Ph)

17.7 ml (0.2 mol) of an aqueous solution of hydrogen peroxide at 35% are added, dropwise in two hours, to a solution, stirred at 0° C., of 8.6 g (24.13 mmol) of 2-[4-(benzyloxycarbonyl)pyrazin-1-yl]-5-nitroaniline obtained in the preceding step and 34.4 ml (29.4 mmol) of formic acid. The mixture is stirred for 3 hours at 0° C. and for 12 hours at 20° C. and is then poured over 300 g of ice. The pH of the medium is adjusted to 8 by adding an aqueous ammonia solution, and then extracted with 200 ml of dichloromethane. The organic phase is washed with 100 ml of a saturated solution of sodium chloride, dried over magnesium sulphate and then concentrated under reduced pressure. A residue is obtained, which is purified by silica column chromatography, elution being carried out with a mixture of dichloromethane and ethyl acetate. 1.2 g of the expected product are thus isolated. $^1$H NMR (CDCl$_3$), δ (ppm): 4.11 (m, 2H); 4.21 (m, 2H); 5.05 (s, 2H); 5.18 (s, 2H); 7.38 (m, 6H); 8.21 (dxd, 1H); 8.61 (d, 1H).

VI-3 7-amino-3-benzyloxycarbonyl-1,2,3,4-tetrahydro-pyrazino[1,2-a]benzimidazole (Compound No. VII-f)

7.68 g (34.06 mmol) of tin chloride dihydrate are added, in several steps, to a solution, in 56 ml of dimethylformamide, of 2 g (5.68 mmol) of compound (XV), obtained in the preceding step, and of 2.6 g (8.85 mmol) of tetrabutylammonium bromide. The mixture is stirred at 20° C. for 24 hours and then concentrated and taken up with 100 ml of water. The pH of the solution thus obtained is adjusted to 9 by adding an aqueous ammonia solution. The mixture is subsequently extracted twice with 100 ml of ethyl acetate. The organic phases are combined, washed twice with 50 ml of water and once with 50 ml of a saturated solution of sodium chloride, dried over magnesium sulphate and then concentrated under reduced pressure. A residue is obtained, which is purified by silica column chromatography, elution being carried out with a mixture of dichloromethane and methanol. 1.45 g of the expected product are thus isolated.
Mp=115-118° C.

$^1$H NMR (CDCl$_3$), δ (ppm): 3.89 (m, 2H); 4 (m, 2H); 4.7 (m, 4H); 5.12 (s, 2H); 6.51 (dxd, 1H); 6.71 (d, 1H); 7.12 (d, 1H); 7.38 (m, 5H).

EXAMPLE VII 7-aminopyrazino[1,2-a]benzimidazole (Compound No. VII-g)

VII-1 7-nitropyrazino[1,2-a]benzimidazole (Compound No. XXIII)

A mixture of 0.6 g (2.12 mmol) of 2-iodo-4-nitrochlorobenzene (XXI) (G. A. Olah, *J. Org. Chem.*, 1993 (58), 3194-3195), 0.2 g (2.1 mmol) of 2-aminopyrazine (XXII), 2.8 g (8.5 mmol) of cesium carbonate, 0.15 g (0.25 mmol) of Xantphos® (9,9-dimethyl-4,5-bis-(diphenylphosphino)xanthene) and 30 mg (0.13 mmol) of palladium diacetate in 20 ml of dry toluene is heated at 120° C. for 12 hours. After this period of time, the mixture is concentrated under reduced pressure and then taken up in 350 ml of dichloromethane and 200 ml of water. The organic phase is separated, washed with 100 ml of a saturated solution of sodium chloride, dried over magnesium sulphate, and then concentrated under reduced pressure. The resulting product is taken up in 10 ml of dichloromethane, and 0.23 g of the expected product is isolated in the form of a precipitate which is recovered by filtration. The filtrate is purified by silica column chromatography, elution being carried out with a mixture of ethyl acetate and heptane. A further 25 mg of product are thus isolated.

VII-2 7-aminopyrazino[1,2-a]benzimidazole (Compound No. VII-g)

A suspension of 0.22 g (1.03 mmol) of 7-nitropyrazino-[1,2-a]benzimidazole, obtained in the preceding step, of 0.5 g of Raney nickel and of 0.1 ml of hydrazine monohydrate (2.05 mmol) in 100 ml of ethanol is stirred at 20° C. for 2 hours. The insoluble material is removed by filtration and the filtrate is concentrated under reduced pressure. 0.16 g of expected product is thus obtained in the form of a beige solid.
Mp=249-253° C.
$^1$H NMR (DMSO D$_6$), δ (ppm): 5.27 (broad peak, NH$_2$); 6.72 (m, 2H); 7.71 (d, 1H); 7.89 (d, 1H); 8.73 (d, 1H); 8.89 (s, 1H).

EXAMPLES VIII 7-aminopyrimido[1,2-a]benzimidazole (Compound No. VII-h and
8-aminopyrimido[1,2-a]-benzimidazole (Compound No. VII-i)

VIII-1 7-nitropyrimido[1,2-a]benzimidazole hydrochloride and 8-nitropyrimido[1,2-a]benzimidazole hydrochloride (Compounds No. XXVI)

A mixture of 2 g (11.2 mmol) of 2-amino-5-nitro-benzimidazole (J. Med. Chem., 1995, 38(20), 4098-4105) and of 3.6 ml (15 mmol) of 1,1,3,3-tetraethoxypropane in 50 ml of ethanol and 2 ml of concentrated hydrochloric acid is refluxed for 12 hours. 1.97 g of a beige precipitate is recovered by filtration and is dried under reduced pressure. A mixture of isomers is obtained, which is used as it is in the subsequent step.

VIII-2 7-aminopyrimido[1,2-a]benzimidazole (Compound No. VII-h)

4.5 g (19.95 mmol) of tin chloride dihydrate in 4 ml of water are added to a suspension, heated to 100° C., of 1 g (3.99 mmol) of the mixture of compounds (XXVI), prepared in the preceding step, in 8 ml of concentrated hydrochloric acid. The reaction mixture is heated for 3 hours and then cooled and the pH of the medium is adjusted to 8 by successive additions of a 30% aqueous ammonia solution. The mixture is extracted three times with 100 ml of dichloromethane. The organic phases are combined, dried over magnesium sulphate, concentrated under reduced pressure and then purified by silica column chromatography, elution being carried out with a mixture of dichloromethane and methanol. 7-aminopyrimido[1,2-a]benzimidazole is thus isolated in the form of an orange solid.

$^1$H NMR (DMSO $D_6$), δ (ppm): 5.21 (m, $NH_2$); 6.7 (d, 1H); 6.81 (s, 1H); 6.95 (m, 1H); 7.9 (d, 1H); 7.58 (m, 1H); 9.25 (dxd, 1H).

VIII-3 8-aminopyrimido[1,2-a]benzimidazole (Compound No. VII-i)

During the extraction described in Example VIII-2, insoluble material precipitates in the aqueous phase. This insoluble material is recovered by filtration over sintered glass, which makes it possible to isolate 0.13 g of an orange solid corresponding to Compound No. VII-i.

$^1$H NMR (DMSO $D_6$), δ (ppm): 5.21 (m, $NH_2$); 6.91 (m, 2H); 7.2 (d, 1H); 7.51 (d, 1H); 8.57 (m, 1H); 9.12 (dxd, 1H).

EXAMPLE IX

6-amino-2,3-dihydro-3-hydroxy-1H-pyrrolo[1,2-a]benzimidazole (Compound No. VII-j) and 6-amino-2,3-dihydro-2-hydroxy-1H-pyrrolo[1,2-a]benzimidazole hydrochloride (Compounds No. VII-k)

IX-1 2-(3-hydroxypyrrolidin-1-yl)-5-nitroaniline

According to a process similar to that described in Example II-1, starting from 3 g (19.22 mmol) of 2-fluoro-5-nitroaniline and 1.76 ml (21.14 mmol) of 3-hydroxypyrrolidine, 2 g of expected compound are obtained in the form of a yellow solid.

IX-2 2,3-dihydro-3-hydroxy-6-nitro-1H-pyrrolo-[1,2-a]benzimidazole and 2,3-dihydro-2-hydroxy-6-nitro-1H-pyrrolo[1,2-a]benzimidazole According to a process similar to that described in Example II-2, starting from 2 g (7.7 mmol) of 2-(3-hydroxypyrrolidin-1-yl)-5-nitroaniline, obtained in the preceding step, 48 mg of a yellow solid corresponding to 2,3-dihydro-3-hydroxy-6-nitro-1H-pyrrolo[1,2-a]benzimidazole and 280 mg of a yellow solid corresponding to 2,3-dihydro-2-hydroxy-6-nitro-1H-pyrrolo[1,2-a]benzimidazole are obtained after purification by silica column chromatography.

IX-3 6-amino-2,3-dihydro-3-hydroxy-1H-pyrrolo-[1,2-a]benzimidazole (Compound No. VII-j)

According to a process similar to that described in Example VII-2, starting from 0.13 g (0.56 mmol) of 2,3-dihydro-3-hydroxy-6-nitro-1H-pyrrolo[1,2-a]-benzimidazole, prepared in step IX-2, 0.1 g of the expected amine is isolated in the form of a brown solid (the reaction mixture is stirred for 2 days at 20° C. in this case).

$^1$H NMR ($CDCl_3$), δ (ppm): 2.61 (m, 1H); 2.92 (m, 1H); 3.94 (m, 1H); 4.18 (m, 1H); 5.29 (m, 1H); 6.61 (d, 1H); 6.98 (s, 1H); 7.05 (d, 1H).

IX-4 6-amino-2,3-dihydro-2-hydroxy-1H-pyrrolo[1,2-a]-benzimidazole hydrochloride (Compounds No. VII-k)

A mixture of 0.3 g (1.36 mmol) of the 2,3-dihydro-2-hydroxy-6-nitro-1H-pyrrolo[1,2-a]benzimidazole obtained in step IX-2 and of 100 mg of palladium-on-charcoal at 10% in 15 ml of ethanol and 2 ml of 1N hydrochloric acid is stirred for 5 hours at 20° C. under 4 bar of hydrogen. After this period of time, the reaction mixture is filtered over a celite buffer, the filtrate is concentrated under reduced pressure, and 0.35 g of the expected product is obtained in the form of a solid.

$^1$H NMR (DMSO $D_6$), δ (ppm): 3.05 (m, 1H); 3.55 (dxd, 1H); 4.15 (m, 1H); 4.45 (dxd, 1H); 5.1 (m, 1H); 7.0 (m, 1H); 7.3 (m, 1H); 7.66 (m, 1H).

EXAMPLE X

6-amino-2,3-dihydro-2-methoxy-1H-pyrrolo[1,2-a]benzimidazole (Compound No. VII-l)

X-1 2,3-dihydro-2-methoxy-6-nitro-1H-pyrrolo-[1,2-a]benzimidazole

A solution of 0.28 g (1.28 mmol) of 2,3-dihydro-2-hydroxy-6-nitro-1H-pyrrolo[1,2-a]benzimidazole (step IX-2 of Example IX) in 5 ml of tetrahydrofuran is added to a suspension, stirred under argon at 20° C., of 0.2 g (5 mmol) of sodium hydride at 60% in 10 ml of tetrahydrofuran. After stirring for fifteen minutes, 0.24 ml (2.5 mmol) of dimethyl sulphate is added. The reaction mixture is stirred at 20° C. for 12 hours and then poured in 100 ml of water and extracted three times with 50 ml of ethyl acetate. The organic phases are combined, washed with a saturated aqueous solution of sodium chloride, dried over magnesium sulphate and concentrated under reduced pressure. The residue obtained is purified by silica column chromatography, elution being carried out with a mixture of dichloromethane and methanol. 70 mg of the expected product are thus isolated in the form of a foam.

X-2 6-amino-2,3-dihydro-2-methoxy-1H-pyrrolo-[1,2-a]benzimidazole (Compound No. VII-l)

According to a process similar to that described in Example VII-2, starting from 0.185 g (0.79 mmol) of 2,3-dihydro-2-methoxy-6-nitro-1H-pyrrolo[1,2-a]-benzimidazole, 60 mg of a beige solid corresponding to the expected product are obtained after purification by silica column chromatography.

Mp=140-142° C.

$^1$H NMR ($CDCl_3$), δ (ppm): 3.01 (dxd, 1H); 3.25 (dxd, 1H); 3.38 (s, 3H); 3.94 (dxd, 1H); 4.19 (dxd, 1H); 4.62 (m, 1H); 6.57 (dxd, 1H); 6.95 (d, 1H); 7.02 (d, 1H).

EXAMPLE XI

7-amino-4-methyl-1,2,3,4-tetrahydro-pyrimido[1,2-a]benzimidazole hydrochloride (1:1) (Compound No. VII-m)

XI-1 N-(2-bromo-5-nitrophenyl)formimidoyl dichloride (XXVIII)

A solution of 5 g (20.4 mmol) of N-(2-bromo-5-nitrophenyl)formamide (XXVII) in 12 ml (164 mmol) of thionyl chloride and 4.5 ml (56 mmol) of sulphuryl chloride is heated at 60° C. for 24 hours. The reaction mixture is concentrated under reduced pressure and 5.3 g of a grey solid is obtained, which will be used as it is in the subsequent synthesis.

XI-2 N-(2-bromo-5-nitrophenyl)-N-(1-methyl-1H-3,4,5,6-tetrahydropyrimidin-2-ylidene)amine (XXX)

A suspension of 5.3 g (17.8 mmol) of the intermediate (XXVIII) in 30 ml of tetrahydrofuran is added, in several steps, to a solution, stirred at 0° C., of 10.5 ml (0.1 mol) of N-methyl-1,3-propanediamine (XXIX, n=3) in 50 ml of tetrahydrofuran. The reaction mixture is subsequently stirred at 20° C. for 48 hours and then poured into 200 ml of water. The mixture is extracted with three times 50 ml of ethyl acetate. The organic phases are combined, washed with 100 ml of a saturated aqueous solution of sodium chloride and then dried over sodium sulphate and concentrated under reduced pressure. The product obtained is purified by silica column chromatography, elution being carried out with a mixture of dichloromethane and methanol. 0.72 g of the expected product (XXIX) is thus isolated in the form of a yellow solid.

XI-3 4-methyl-7-nitro-1,2,3,4-tetrahydropyrimido[1,2-a]benzimidazole (XXXI)

A mixture of 0.72 g (2.3 mmol) of intermediate (XXX), 0.16 g (0.28 mmol) of Xantphos® (9,9-dimethyl-4,5-bis-(diphenylphosphino)xanthene), 1.5 g (4.6 mmol) of cesium carbonate and 30 mg (0.14 mmol) of palladium diacetate in 20 ml of toluene is heated at 120° C. for 24 hours. After this period of time, the mixture is concentrated under reduced pressure and then purified by silica column chromatography, elution being carried out with a mixture of dichloromethane and methanol. 0.44 g of the expected product (XXXI) is thus isolated.

Mp=172-178° C.
$^1$H NMR (CDCl$_3$), δ (ppm): 2.42 (quint., 2H); 3.39 (s, 3H); 3.58 (t, 2H); 4.15 (t, 2H); 7.09 (d, 1H); 8.09 (dxd, 1H); 8.38 (d, 1H).

XI-4 7-amino-4-methyl-1,2,3,4-tetrahydropyrimido[1,2-a]benzimidazole hydrochloride (1:1) (Compound No. VII-m)

0.2 ml (3.8 mmol) of hydrazine monohydrate is added to a suspension of 0.44 g (1.89 mmol) of compound (XXX) and 0.3 g of Raney nickel. The mixture is stirred at 20° C. for 3 hours and then filtered over a celite buffer, concentrated under reduced pressure and purified by silica column chromatography, elution being carried out with a mixture of dichloromethane and methanol. 0.36 g of the expected product (VII-m) is thus isolated. The compound can optionally be isolated in the form of a hydrochloride by taking up the product obtained in 50 ml of a 0.1N solution of hydrochloric acid in isopropanol and concentrating the solution obtained under reduced pressure. The hydrochloride of the amine (VII-m) is thus isolated.

Mp (HCl 1:1): 335-340° C.
$^1$H NMR (CDCl$_3$), δ (ppm): 2.17 (quint., 2H); 3.1 (s, 3H); 3.25 (t, 2H); 3.82 (t, 2H); 6.31 (dxd, 1H); 6.7 (d, 1H); 6.76 (d, 1H).

EXAMPLE XII 8-amino-5-methyl-1,2,3,4-tetrahydro-5-H-[1,3]diazepino[1,2-a]benzimidazole (Compound No. VII-n)

The compound (VII-n) is prepared according to a process similar to that described in Example (XIII), using the intermediates (XXVIII) and (XXIX, n=4).

Mp (2HCl): 330-336° C.
$^1$H NMR (CDCl$_3$), δ (ppm): 1.84 (m, 4H); 3.06 (s, 3H); 3.08 (m, 2H); 3.8 (m, 2H); 6.42 (dxd, 1H); 6.81 (d, 1H); 6.85 (s, 1H).

The following examples describe the preparation of certain compounds in accordance with the invention. These examples are not limiting and merely illustrate the present invention. The numbers of the compounds exemplified refer to those in Tables 2, 3 and 4. The elemental microanalyses, the LC-MS (liquid chromatography-mass spectrometry) analyses and the IR or NMR spectra confirm the structures of the compounds obtained.

EXAMPLE 1

Compound No. 1 of Table 2

N-(1,2,3,4-tetrahydropyrido[1,2-a]benzimidazol-7-yl)-5-fluoro-1-[(pyridin-4-yl)methyl]-1H-indole-2-carboxamide 1.1. ethyl 5-fluoro-1-[(pyridin-4-yl)methyl]-1H-indole-2-carboxylate A solution of 5.5 g (21.72 mmol) of 1,1'-azodicarbonyl-dipiperidine, in solution in 15 ml of dry toluene, is added, under argon at 20° C., dropwise, to a solution of 3 g (14.48 mmol) of ethyl 5-fluoro-1H-indole-2-carboxylate, 2.37 g (21.72 mmol) of 4-pyridylcarbinol and 5.45 ml (21.72 mmol) of n-tributylphosphine in 200 ml of toluene. The mixture is stirred at 20° C. for 48 h. The reaction mixture is subsequently concentrated under reduced pressure. The residue is purified by silica column chromatography (eluent: heptane/ethyl acetate). 3.2 g of the expected product are thus isolated, which product is used as it is in the subsequent synthesis.

1.2 N-(1,2,3,4-tetrahydropyrido[1,2-a]benzimidazol-7-yl)-5-fluoro-1-[(pyridin-4-yl)methyl]-1H-indole-2-carboxamide (Compound No. 1)

1.26 ml of trimethylaluminum (2M in toluene) are added, under argon, to a solution of 0.376 g (2.01 mmol) of 7-amino-1,2,3,4-tetrahydropyrido[1,2-a]benzimidazole (Saunders et al., *J. Chem. Soc.*, 1955, 3275-3287) in 70 ml of dry toluene. After stirring at 0° C. for 15 min, the mixture is brought to 50° C. and the stirring is maintained for 30 min. The mixture is subsequently cooled to 0° C. 0.5 g (1.68 mmol) of ethyl 5-fluoro-1-[(pyridin-4-yl)methyl]-1H-indole-2-carboxylate, obtained in step 1.1, is added. The reaction mixture is brought to reflux for 12 h, then cooled and added to 20 ml of an ice-cold 1N solution of hydrochloric acid. The pH of the aqueous phase is adjusted to 9. Insoluble material, recovered by filtration, is purified by silica column chromatography (eluent: dichloromethane-methanol). The product thus purified is recrystallized from a mixture of dichloromethane and heptane. 0.41 g of a white solid is obtained after drying under reduced pressure.

Melting point (base): 292-293° C.
$^1$H NMR (DMSO D$_6$), δ (ppm): 1.91 (m, 4H); 2.89 (t, 2H); 4.02 (t, 2H); 5.9 (s, 2H); 6.93 (d, 2H); 7.09 (txd, 1H); 7.5 (m, 5H); 7.89 (d, 1H); 8.4 (d, 2H); 10.35 (s, 1H).

EXAMPLE 2

Compound No. 2 of Table 2

N-(1,2,3,4-tetrahydropyrido[1,2-a]benzimidazol-7-yl)-5-fluoro-1-(3-fluorobenzyl)-1H-indole-2-carboxamide

2.1 ethyl 5-fluoro-1-(3-fluorobenzyl)-1H-indole-2-carboxylate

A suspension of 1.035 g (5 mmol) of ethyl 5-fluoro-1H-indole-2-carboxylate, 0.865 g (6 mmol) of 3-fluorobenzyl chloride and 1.38 g (10 mmol) of potassium carbonate in 50 ml of dimethylformamide is stirred for 24 h at 60° C. The reaction mixture is subsequently cooled and poured into a mixture of ice-cold water and of ethyl acetate. After separation by settling out, the organic phase is separated and is then washed with twice 200 ml of water then with 200 ml of a saturated solution of sodium chloride. The solution is dried over magnesium sulphate and filtered and the filtrate is then concentrated under reduced pressure. 0.97 g of an oil is obtained, which oil is used as it is in the subsequent step.

2.2 N-(1,2,3,4-tetrahydropyrido[1,2-a]benzimidazol-7-yl)-5-fluoro-1-(3-fluorobenzyl)-1H-indole-2-carboxamide (Compound No. 2)

1.43 ml of trimethylaluminum (2M in toluene) are added, under argon, to a solution of 0.426 g (2.28 mmol) of 7-amino-1,2,3,4-tetrahydropyrido[1,2-a]benzimidazole (Saunders et al., *J. Chem. Soc.*, 1955, 3275-3287) in 70 ml of dry toluene. After stirring at 0° C. for 15 min, the mixture is brought to 50° C. and the stirring is maintained for 30 min. The mixture is subsequently cooled to 0° C. and 0.6 g (1.9 mmol) of ethyl 5-fluoro-1-(3-fluorobenzyl)-1H-indole-2-carboxylate, obtained in step 2.1, is added. The reaction mixture is brought to reflux for 12 h, then cooled and added to 20 ml of an ice-cold 1N solution of hydrochloric acid. The pH of the aqueous phase is adjusted to pH 9. An insoluble material is recovered by filtration and is purified by silica column chromatography (eluent: dichloromethane-methanol). The product thus purified is recrystallized from methanol. 0.46 g of a white solid is obtained after drying under reduced pressure.

Melting point (base): 286-287° C.

$^1$H NMR (DMSO $D_6$), δ (ppm): 2 (m, 4H); 2.9 (t, 2H); 4.05 (t, 2H); 5.88 (s, 2H); 7.11 (m, 10H); 7.91 (s, 1H); 10.38 (s, 1H).

EXAMPLE 3

Compound No. 3 of Table 2

N-(1,2,3,4-tetrahydropyrido[1,2-a]benzimidazol-7-yl)-1-benzyl-1H-pyrrolo[2,3-b]pyridine-2-carboxamide

3.1 ethyl 1-benzyl-1H-pyrrolo[2,3-b]pyridine-2-carboxylate 2 g (10 mmol) of ethyl pyrrolo[2,3-b]pyridine-2-carboxylate (WO2004101563) are added, portionwise, to a suspension of 0.44 g (11 mmol) of sodium hydride in 50 ml of DMF, stirred at 20° C. After stirring at ambient temperature for 1 h, 2.1 g (12 mmol) of benzyl bromide are added, dropwise, and the reaction mixture is stirred at ambient temperature for 20 h. 150 ml of water and 150 ml of ethyl ether are subsequently added with stirring. The aqueous phase is separated and extracted twice with 50 ml of ethyl ether. The organic phases are combined, washed with 100 ml of water, dried over sodium sulphate and then concentrated under reduced pressure. The resulting product is purified by silica column chromatography, elution being carried out with a mixture of heptane and dichloromethane. 2.3 g of the expected product are thus isolated.

Melting point=71-72° C.

3.2 N-(1,2,3,4-tetrahydropyrido[1,2-a]benzimidazol-7-yl)-1-benzyl-1H-pyrrolo[2,3-b]pyridine-2-carboxamide (Compound No. 3)

1.1 ml of trimethylaluminum (2M in toluene) are added, under argon, to a solution of 0.32 g (1.71 mmol) of 7-amino-1,2,3,4-tetrahydropyrido[1,2-a]benzimidazole (Saunders et al., *J. Chem. Soc.*, 1955, 3275-3287) in 20 ml of dry toluene. After stirring at 0° C. for 15 min, the mixture is brought to 50° C. and the stirring is maintained for 30 min. The mixture is subsequently cooled to 0° C. and 0.4 g (1.43 mmol) of ethyl 1-benzyl-1H-pyrrolo[2,3-b]pyridine-2-carboxylate, obtained in step 3.1, is added. The reaction mixture is brought to reflux for 6 h and then cooled and 150 ml of water, 2 drops of a 35% aqueous solution of sodium hydroxide and 150 ml of dichloromethane are added with stirring. The aqueous phase is separated and extracted twice with 50 ml of dichloromethane. The organic phases are combined, washed with 100 ml of water, dried over sodium sulphate and then concentrated under reduced pressure. The resulting product is purified by silica column chromatography, elution being carried out with a mixture of methanol-dichloromethane. 0.55 g of product is thus isolated, which product is recrystallized from ethanol so as to obtain, after drying under vacuum, 0.45 g of the expected compound in the form of a powder.

Melting point=233-235° C.

$^1$H NMR (DMSO $D_6$), δ (ppm): 1.91 (m, 4H); 2.91 (t, 2H); 4.02 (t, 2H); 5.9 (s, 2H); 7.12 (m, 6H); 7.38 (m, 2H); 7.48 (m, 1H); 7.9 (s, 1H); 8.18 (dxd, 1H); 8.4 (dxd, 1H).

EXAMPLE 4

Compound No. 4 of Table 2

N-(1,2,3,4-tetrahydropyrido[1,2-a]benzimidazol-7-yl)-1-benzyl-5-trifluoromethyl-1H-pyrrolo[2,3-b]pyridine-2-carboxamide

4.1 ethyl 1-benzyl-5-trifluoromethyl-1H-pyrrolo[2,3-b]pyridine-2-carboxylate 0.58 g (5.23 mmol) of benzyl alcohol, 1.4 g (5.23 mmol) of triphenylphosphine and 0.94 g (5.23 mmol) of diethyl azodicarboxylate (DEAD) are added, with stirring, to a suspension of 0.9 g (3.5 mmol) of ethyl 5-trifluoro-methyl-1H-pyrrolo[2,3-b]pyridine-2-carboxylate (Nazare, M. et al., *Angewandte Chemie, International Ed.*, 2004, 43(34), 4526-4528) in 45 ml of dry tetrahydrofuran. After stirring at ambient temperature for 20 h, the reaction mixture is concentrated under reduced pressure and the resulting product is purified by silica column chromatography, elution being carried out with a mixture of dichloromethane and heptane. 1 g of the expected product is thus obtained.

Melting point=72-73° C.

4.2 N-(1,2,3,4-tetrahydropyrido[1,2-a]benzimidazol-7-yl)-1-benzyl-5-trifluoromethyl-1H-pyrrolo[2,3-b]pyridine-2-carboxamide (Compound No. 4)

0.65 ml of trimethylaluminum (2M in toluene) is added, under argon, to a solution of 0.19 g (1.03 mmol) of 7-amino-1,2,3,4-tetrahydropyrido[1,2-a]benzimidazole (Saunders et al., *J. Chem. Soc.*, 1955, 3275-3287) in 20 ml of dry toluene. After stirring at 0° C. for 15 min, the mixture is brought to 50° C. and the stirring is maintained for 30 min. The mixture is subsequently cooled to 0° C. and 0.3 g (0.86 mmol) of ethyl 1-benzyl-5-trifluoromethyl-1H-pyrrolo[2,3-b]pyridine-2-carboxylate, obtained in step 4.1, is added. The reaction mixture is brought to reflux for 6 h and then cooled and 150 ml of water, 2 drops of a 35% aqueous solution of sodium hydroxide and 150 ml of dichloromethane are added with stirring. The aqueous phase is separated and extracted twice with 50 ml of dichloromethane. The organic phases are combined, washed with 100 ml of water, dried over sodium sulphate and then concentrated under reduced pressure. The resulting product is purified by silica column chromatography, elution being carried out with a mixture of methanol-dichloromethane. 0.4 g of product is thus isolated, which product is recrystallized from acetonitrile so as to obtain, after drying under vacuum, 0.35 g of the expected compound in the form of a powder.

Melting point=241-243° C.

$^1$H NMR (DMSO D$_6$), δ (ppm): 1.91 (m, 4H); 2.93 (t, 2H); 4.05 (t, 2H); 5.98 (s, 2H); 7.15 (m, 5H); 7.42 (m, 3H); 7.9 (d, 1H), 8.7 (dxd, 2H), 10.5 (s, 1H).

EXAMPLE 5

Compound No. 5 of Table 2

N-(2,3-dihydro-1H-pyrrolo[1,2-a]benzimidazol-6-yl)-5-fluoro-1-[(pyridin-4-yl)methyl]-1H-indole-2-carboxamide 1.26 ml of trimethylaluminum (2M in toluene) are added, under argon, to a solution of 0.35 g (2.01 mmol) of 6-amino-2,3-dihydro-1H-pyrrolo[1,2-a]benzimidazole (Freedman et al., *J. Het. Chem.*, 1966, 3, (3), 257-259) in 70 ml of dry toluene. After stirring at 0° C. for 15 min, the mixture is brought to 50° C. and the stirring is maintained for 30 min. The mixture is cooled to 0° C. and 0.5 g (1.68 mmol) of ethyl 5-fluoro-1-[(pyridin-4-yl)methyl]-1H-indole-2-carboxylate, obtained in step 1.1, is added. The reaction mixture is brought to reflux for 12 h and then cooled and poured into 20 ml of an ice-cold 1N solution of hydrochloric acid. The pH of the aqueous phase is adjusted to 9. An insoluble material is recovered by filtration and is purified by silica column chromatography (eluent: dichloromethane-methanol). The product thus purified is recrystallized from a mixture of dichloromethane-heptane. 0.23 g of a white solid is obtained after drying under reduced pressure.

Melting point (base): 266-267° C.

$^1$H NMR (DMSO D$_6$), δ (ppm): 2.6 (m, 2H); 2.9 (t, 2H); 4.08 (t, 2H); 5.9 (s, 2H); 6.95 (d, 2H); 7.1 (txd, 1H); 7.45 (m, 5H); 7.92 (d, 1H); 8.42 (d, 2H); 10.31 (s, 1H).

EXAMPLE 6

Compound No. 6 of Table 2

N-(2,3-dihydro-1H-pyrrolo[1,2-a]benzimidazol-6-yl)-5-fluoro-1-(3-fluorobenzyl)-1H-indole-2-carboxamide 1.43 ml of trimethylaluminum (2M in toluene) are added, under argon, to a solution of 0.39 g (2.28 mmol) of 6-amino-2,3-dihydro-1H-pyrrolo[1,2-a]benzimidazole (Freedman et al., *J. Het. Chem.*, 1966, 3, (3), 257-259) in 70 ml of dry toluene. After stirring at 0° C. for 15 min, the mixture is brought to 50° C. and the stirring is maintained for 30 min. The mixture is subsequently cooled to 0° C. and 0.6 g (1.9 mmol) of ethyl 5-fluoro-1-(3-fluorobenzyl)-1H-indole-2-carboxylate, obtained in step 2.1, is added. The reaction mixture is brought to reflux for 12 h and is then cooled and poured into 20 ml of an ice-cold 1N solution of hydrochloric acid. The pH of the aqueous phase is adjusted to 9. An insoluble material is recovered by filtration and is purified by silica column chromatography (eluent: dichloromethane-methanol). The product thus purified is recrystallized from a mixture of dichloromethane and heptane. 0.45 g of a white solid is obtained after drying under reduced pressure.

Melting point (base): 256-257° C.

$^1$H NMR (DMSO D$_6$), δ (ppm): 2.56 (m, 2H); 2.91 (t, 2H); 4.04 (t, 2H); 5.9 (s, 2H); 7.2 (m, 10H); 7.92 (d, 1H); 10.32 (s, 1H).

EXAMPLE 7

Compound No. 7 of Table 2

N-(2,3-dihydro-1H-pyrrolo[1,2-a]benzimidazol-6-yl)-1-benzyl-1H-pyrrolo[2,3-b]pyridine-2-carboxamide 0.67 ml of trimethylaluminum (2M in toluene) is added, under argon, to a solution of 0.185 g (1.07 mmol) of 6-amino-2,3-dihydro-1H-pyrrolo[1,2-a]benzimidazole (Freedman et al., *J. Het. Chem.*, 1966, 3, (3), 257-259) in 20 ml of dry toluene. After stirring at 0° C. for 15 min, the mixture is brought to 50° C. and the stirring is maintained for 30 min. The mixture is subsequently cooled to 0° C. and 0.25 g (0.89 mmol) of ethyl 1-benzyl-1H-pyrrolo[2,3-b]pyridine-2-carboxylate, obtained in step 3.1, is added. The reaction mixture is brought to reflux for 6 h and then cooled and 150 ml of water, 2 drops of a 35% aqueous solution of sodium hydroxide and 150 ml of dichloromethane are added with stirring. The aqueous phase is separated and extracted twice with 50 ml of dichloromethane. The organic phases are combined, washed with 100 ml of water, dried over sodium sulphate and then concentrated under reduced pressure. The resulting product is purified by silica column chromatography, elution being carried out with a mixture of methanol and dichloromethane. 0.34 g of product is thus isolated, which product is recrystallized from ethanol so as to obtain, after drying under vacuum, 0.31 g of the expected compound in the form of a powder.

Melting point=251-252° C.

$^1$H NMR (DMSO D$_6$), δ (ppm): 2.6 (m, 2H); 2.9 (t, 2H); 4.04 (t, 2H); 5.9 (s, 2H); 7.15 (m, 9H); 7.9 (d, 1H); 8.18 (dxd, 1H); 8.4 (dxd, 1H).

EXAMPLE 8

Compound No. 8 of Table 2

N-(2,3-dihydro-1H-pyrrolo[1,2-a]benzimidazol-6-yl)-1-benzyl-5-trifluoromethyl-1H-pyrrolo[2,3-b]pyridine-2-carboxamide 0.65 ml of trimethylaluminum (2M in toluene) is added, under argon, to a solution of 0.18 g (1.03 mmol) of 6-amino-2,3-dihydro-1H-pyrrolo[1,2-a]benzimidazole (Freedman et al., *J. Het. Chem.*, 1966, 3, (3), 257-259) in 20 ml of dry toluene. After stirring at 0° C. for 15 min, the mixture is brought to 50° C. and the stirring is maintained for 30 min. The mixture is subsequently cooled to 0° C. and 0.3 g (0.86 mmol) of ethyl 1-benzyl-5-trifluoromethyl-1H-pyrrolo[2,3-b]pyridine-2-carboxylate, obtained in step 4.1, is added. The reaction mixture is brought to reflux for 6 h and then cooled and 150 ml of water, 2 drops of a 35% aqueous solution of sodium hydroxide and 150 ml of dichloromethane are added with stirring. The aqueous phase is separated and extracted twice with 50 ml of dichloromethane. The organic phases are combined, washed with 100 ml of water, dried over sodium sulphate and then concentrated under reduced pressure. The resulting product is purified by silica column chromatography, elution being carried out with a mixture of methanol-dichloromethane. 0.37 g of product is thus isolated, which product is recrystallized from acetonitrile so as to obtain, after drying under vacuum, 0.3 g of the expected compound in the form of a powder. Melting point=268-270° C.

$^1$H NMR (DMSO D$_6$), δ (ppm): 2.6 (m, 2H); 2.9 (t, 2H); 4.04 (t, 2H); 6 (s, 2H); 7.12 (m, 5H); 7.42 (m, 3H); 7.92 (s, 1H); 8.7 (d, 2H).

EXAMPLE 9

Compound No. 148 of Table 3

N-(pyrido[1,2-a]benzimidazol-7-yl)-5-fluoro-1-(3-fluorobenzyl)-1H-indole-2-carboxamide 1.19 ml of trimethylaluminum (2M in toluene) are added, under argon, to a solution of 0.348 g (1.9 mmol) of 7-aminopyrido[1,2-a]benzimidazole (Begunov et al., *Russian J. Org. Chem.*, 2004, (40), 11, 1694-1696) in 70 ml of dry toluene. After stirring at 0° C. for 15 min, the mixture is brought to 50° C. and the stirring is maintained for 30 min. The mixture is subsequently cooled to 0° C. and 0.5 g (1.9 mmol) of ethyl 5-fluoro-1-(3-fluorobenzyl)-1H-indole-2-carboxylate, obtained in step 2.1, is added. The reaction mixture is brought to reflux for 12 h and then cooled and added to 20 ml of an ice-cold 1N solution of hydrochloric acid. The pH of the aqueous phase is adjusted to 9. An insoluble material is recovered by filtration and purified by preparative chromatography (eluent: dichloromethane-methanol). The product thus purified is recrystallized from methanol. 0.53 g of the expected product is obtained in the form of a white solid after drying under reduced pressure.

Melting point (base): 261-262° C.

$^1$H NMR (DMSO D$_6$), δ (ppm): 5.9 (s, 2H); 7.01 (m, 6H); 7.55 (m, 6H); 8.2 (d, 2H); 9.0 (s, 1H).

EXAMPLE 10

Compound No. 149 of Table 3

N-(pyrido[1,2-a]benzimidazol-7-yl)-5-fluoro-1-[(pyridin-4-yl)methyl]-1H-indole-2-carboxamide 1.51 ml of trimethylaluminum (2M in toluene) are added, under argon, to a solution of 0.442 g (2.41 mmol) of 7-aminopyrido[1,2-a]benzimidazole (Begunov et al., *Russian J. Org. Chem.*, 2004, (40), 11, 1694-1696) in 70 ml of dry toluene. After stirring at 0° C. for 15 min, the mixture is brought to 50° C. and the stirring is maintained for 30 min. The mixture is subsequently cooled to 0° C. and 0.6 g (2.01 mmol) of ethyl 5-fluoro-1-[(pyridin-4-yl)methyl]-1H-indole-2-carboxylate, obtained in step 1.1, is added. The reaction mixture is brought to reflux for 12 h and then cooled and added to 20 ml of an ice-cold 1N solution of hydrochloric acid. The pH of the aqueous phase is adjusted to 9. An insoluble material is filtered off and purified by preparative chromatography (eluent: dichloromethane-methanol). The product thus purified is recrystallized from methanol. 0.35 g of the expected product is obtained in the form of a white solid after drying under reduced pressure.

Melting point (base): 277-278° C.

$^1$H NMR (DMSO D$_6$), δ (ppm): 5.9 (s, 2H); 6.99 (m, 3H); 7.11 (dxt, 1H); 7.58 (m, 6H); 8.21 (m, 2H); 8.44 (d, 2H); 9.05 (d, 1H).

EXAMPLE 11

Compound No. 150 of Table 3

N-(pyrimido[1,2-a]benzimidazol-7-yl)-5-fluoro-1-(3-fluorobenzyl)-1H-indole-2-carboxamide 11.1
5-fluoro-1-(3-fluorobenzyl)-1H-indole-2-carboxylic acid An aqueous solution of sodium hydroxide, prepared from 1.15 g (28.92 mmol) of sodium hydroxide pellets in 50 ml of water, is added to a solution of 7.6 g (24.10 mmol) of ethyl 5-fluoro-1-(3-fluorobenzyl)-1H-indole-2-carboxylate (obtained in step 2.1) in 240 ml of ethanol. The mixture is heated for two hours and then concentrated under reduced pressure. The resulting solid is taken up in 200 ml of water. The solution is washed with twice 100 ml of ethyl ether, acidified by successive additions of small amounts of concentrated hydrochloric acid and then extracted with 200 ml of ethyl acetate. The organic phase is finally washed twice with 100 ml of water and once with 50 ml of a saturated solution of sodium chloride, dried over magnesium sulphate and concentrated under reduced pressure. After drying at 50° C. under reduced pressure, 6.4 g of the expected product are obtained in the form of a solid that will be used as it is in the subsequent step.

11.2 N-(pyrimido[1,2-a]benzimidazol-7-yl)-5-fluoro-1-(3-fluorobenzyl)-1H-indole-2-carboxamide (Compound No. 150)

140 mg (0.532 mmol) of 70% pure 7-aminopyrimido[1,2-a]-benzimidazole (VII-h) are added to a solution, stirred at 20° C., of 0.22 g (0.76 mmol) of compound prepared in step 11.1, 146 mg (0.76 mmol) of N-(3-dimethylaminopropyl)-N'-ethylcarbodiimide hydrochloride (EDAC) and 103 mg (0.76 mmol) of 1-hydroxybenzotriazole (HOBT) in 5 ml of DMF. The reaction mixture is stirred at 20° C. for 48 hours and is then poured into 50 ml of water. The mixture is subsequently extracted with 3 times 30 ml of ethyl acetate. The combined organic phases are washed twice with 20 ml of water, dried over magnesium sulphate and then concentrated under reduced pressure. The product obtained is purified by silica column chromatography, elution being carried out with a mixture of dichloromethane and methanol. 90 mg of the expected product are thus isolated.

Mf=295-298° C.

$^1$H NMR (DMSO D$_6$), δ (ppm): 10.7 (s, 1H); 9.49 (d, 1H); 8.82 (d, 1H); 8.3 (m, 2H); 7.79 (d, 1H); 7.6 (m, 2H); 7.47 (s, 1H); 7.31 (m, 1H); 7.17 (m, 2H); 7.05 (m, 1H); 6.82 (m, 2H); 5.93 (s, 2H).

EXAMPLE 12

Compound No. 154 of Table 4

N-(2-methoxypyrrolo[1,2-a]benzimidazol-6-yl)-5-fluoro-1-(3-fluorobenzyl)-1H-indole-2-carboxamide hydrochloride (1:1)

Compound 154 is prepared, according to a process similar to the method described in Example 11.2, from the acid prepared in step 11.1 and 6-amino-2-methoxypyrrolo[1,2-a]benzimidazole (VII-l). The resulting solid is subsequently dissolved under hot conditions in a mixture of 2.1 ml of 0.1N hydrochloric acid in isopropanol and 1 ml of methanol. After cooling of the medium, a precipitate is recovered by filtration and is dried under reduced pressure. The expected product is thus isolated in the form of a hydrochloride.

Mp (HCl 1:1)=220-225° C.

$^1$H NMR (DMSO D$_6$), δ (ppm): 3.21 (d, 1H); 3.35 (s, 3H); 3.52 (dxd, 1H); 4.38 (m, 2H); 4.8 (m, 1H); 5.89 (s, 2H); 6.89 (m, 2H); 6.91-7.33 (m, 3H); 7.4-7.8 (m, 4H); 8.27 (s, 1H); 10.68 (s, 1H).

EXAMPLE 13

No. 151 of Table 3

N-(pyrazino[1,2-a]benzimidazol-7-yl)-5-fluoro-1-(3-fluorobenzyl)-1H-indole-2-carboxamide hydrochloride (1:1)

Compound 151 is prepared, according to a process similar to the method described in Example 12, from the acid prepared in step 11.1 and 7-aminopyrazino[1,2-a]-benzimidazole (VII-g).

Mp (HCl 1:1)=225-230° C.

$^1$H NMR (DMSO D$_6$), δ (ppm): 5.91 (s, 2H); 6.81-7.38 (m, 5H); 7.58 (m, 3H); 7.91 (d, 1H); 8.22 (d, 1H); 8.49 (m, 2H); 9.2 (d, 1H); 9.33 (s, 1H); 10.8 (s, 1H).

EXAMPLE 14

No. 26 of Table 2

N-(2,3-dihydro-3-methylimidazo[1,2-a]benzimidazol-6-yl)-5-fluoro-1-(3-fluorobenzyl)-1H-indole-2-carboxamide Compound 26 is prepared, according to a process similar to the method described in Example 1.2, from ethyl 5-fluoro-1-(3-fluorobenzyl)-1H-indole-2-carboxylate, obtained in step 2.1, and 6-amino-2,3-dihydro-1-methyl-imidazo[1,2-a]benzimidazole (VII-c).

Mp=281-282° C.

$^1$H NMR (DMSO D$_6$), δ (ppm): 3.1 (s, 3H); 4.1-4.35 (m, 4H); 5.89 (s, 2H); 6.82 (m, 2H); 6.92-7.2 (m, 2H); 7.21-7.35 (m, 2H); 7.39 (s, 1H); 7.53 (m, 3H); 7.91 (s, 1H).

EXAMPLE 15

No. 50 of Table 2

N-(2,3-dihydro-1H-pyrrolo[1,2-a]benzimidazol-6-yl)-1-[(quinolin-2-yl)methyl]-5-trifluoromethyl-1H-pyrrolo[2,3-b]pyridine-2-carboxamide

15.1 ethyl 1-[(quinolin-2-yl)methyl]-5-trifluoro-methyl-1H-pyrrolo[2,3-b]pyridine-2-carboxylate 0.14 g (0.871 mmol) of (quinolin-2-yl)methanol, 0.228 g (0.871 mmol) of triphenylphosphine and 0.151 g (0.871 mmol) of diethyl azodicarboxylate (DEAD) are added, with stirring, to a suspension of 0.15 g (0.581 mmol) of ethyl 5-trifluoromethyl-1H-pyrrolo[2,3-b]pyridine-2-carboxylate (Nazare, M. et al., *Angewandte Chemie, International Ed.*, 2004, 43(34), 4526-4528) in 2 ml of dry tetrahydrofuran. After stirring at ambient temperature for 20 h, the reaction mixture is concentrated under reduced pressure and the resulting product is purified by silica column chromatography, elution being carried out with a mixture of dichloromethane and heptane. 0.18 g of the expected product is thus obtained in the form of a yellow oil.

15.2 N-(2,3-dihydro-1H-pyrrolo[1,2-a]benzimidazol-6-yl)-1-[(quinolin-2-yl)methyl]-5-trifluoromethyl-1H-pyrrolo[2,3-b]pyridine-2-carboxamide (Compound No. 50)

Compound 50 is prepared, according to a process similar to the method described in Example 5, from 0.18 g (0.45 mmol) of compound obtained in step 15.1 and 0.094 g (0.541 mmol) of 6-amino-2,3-dihydro-1H-pyrrolo[1,2-a]benzimidazole (Freedman et al., *J. Het. Chem.*, 1966, 3, (3), 257-259). 0.22 g of the expected product is thus obtained.

Mp=300-301° C.

$^1$H NMR (DMSO D$_6$), δ (ppm): 2.61 (q, 2H); 2.94 (t, 2H); 4.08 (t, 2H); 6.26 (s, 2H); 7.22 (d, 1H); 7.37 (d, 1H); 7.55-7.46 (m, 2H); 7.6 (s, 1H); 7.67 (dxt, 1H); 7.8 (d, 1H); 7.95-7.81 (m, 2H); 8.27 (d, 1H); 8.73 (s, 2H); 10.65 (s, 1H).

EXAMPLE 16

No. 25 of Table 2

N-(1,2,3,4-tetrahydropyrazino[1,2-a]benzimidazol-7-yl)-5-fluoro-1-(3-fluorobenzyl)-1H-indole-2-carboxamide

16.1 N-(2-benzyloxycarbonyl-1,2,3,4-tetrahydropyrazino[1,2-a]benzimidazol-7-yl)-5-fluoro-1-(3-fluorobenzyl)-1H-indole-2-carboxamide The compound is prepared, according to a process similar to that described in Example 11.2, from the 5-fluoro-1-(3-fluorobenzyl)-1H-indole-2-carboxylic acid described in Example 11.1 and the amine VII-f.

16.2 N-(1,2,3,4-tetrahydropyrazino[1,2-a]benzimidazol-7-yl)-5-fluoro-1-(3-fluorobenzyl)-1H-indole-2-carboxamide (Compound No. 25)

A suspension of 1 g (1.69 mmol) of the compound prepared in the preceding step and of 0.1 g of palladium-on-charcoal at 10% in 100 ml of ethanol is stirred at 20° C. for 6 hours under 5.5 bar of hydrogen. The suspension is subsequently filtered over a celite buffer and concentrated under reduced pressure. The resulting product is purified by silica column chromatography, elution being carried out with a mixture of dichloromethane and methanol. The purified product is taken up in 10 ml of a 0.1N solution of hydrochloric acid in isopropanol, the solution is concentrated under reduced pressure and the resulting solid is triturated from ethyl ether so as to make it possible to isolate 0.48 g of the expected product.

Mp (1HCl)=276-284° C.

$^1$H NMR (DMSO D$_6$), δ (ppm): 3.73 (t, 2H); 4.38 (t, 2H); 4.59 (s, 3H); 5.59 (s, 2H); 6.9 (m, 2H); 7.02 (txd, 1H); 7.15

(txd, 1H); 7.31 (m, 1H); 7.45 (s, 1H); 7.58 (m, 3H); 8.1 (s, 1H); 9.97 (s, 1H); 10.45 (s, 1H).

EXAMPLE 17

No. 81 of Table 2

N-(3-methyl-1,2,3,4-tetrahydropyrazino[1,2-a]-benzimidazol-7-yl)-5-fluoro-1-(3-fluorobenzyl)-1H-indole-2-carboxamide Compound 81 is prepared according to a process similar to that described in Example 6, from ethyl 5-fluoro-1-(3-fluorobenzyl)-1H-indole-2-carboxylate obtained in step 2.1 and 7-amino-3-methyl-1,2,3,4-tetrahydropyrazino[1,2-a]benzimidazole (VII-e).

$^1$H NMR (DMSO D$_6$), δ (ppm): 2.45 (s, 3H); 2.89 (t, 2H); 3.74 (s, 2H); 4.1 (t, 2H); 5.9 (s, 2H); 6.81-7.6 (m, 10H); 7.97 (d, 1H); 10.46 (s, 1H).

EXAMPLE 18

No. 84 of Table 2

N-(2,3-dihydro-1H-pyrrolo[1,2-a]benzimidazol-6-yl)-5-fluoro-1-(2-benzyloxyethyl)-1H-indole-2-carboxamide

18.1 ethyl 5-fluoro-1-(2-benzyloxyethyl)-1H-indole-2-carboxylate

94 μl (0.657 mmol) of 2-benzyloxyethanol and 50.4 mg (0.438 mmol) of (cyanomethylene)trimethylphosphorane (*Tet. Lett.*, 1996, 37, 2459-2462) are added to a solution of 68 mg (0.329 mmol) of ethyl 5-fluoro-1H-indole-2-carboxylate in 2 ml of toluene, stirred at 20° C. The reaction mixture is heated at 110° C. for 12 hours and then concentrated under reduced pressure, taken up in 20 ml of ethyl ether, filtered over a celite buffer and concentrated under reduced pressure. The residue obtained is purified by preparative HPLC, elution being carried out with a mixture of water, acetonitrile and trifluoroacetic acid. 99 mg of a yellow oil are thus isolated.

$^1$H NMR (DMSO D$_6$), δ (ppm): 1.3 (t, 3H); 3.72 (t, 2H); 4.28 (q, 2H); 4.38 (s, 2H); 4.81 (t, 2H); 7.28-7.07 (m, 7H); 7.45 (dxd, 1H); 7.68 (dxd, 1H).

18.2 N-(2,3-dihydro-1H-pyrrolo[1,2-a]benzimidazol-6-yl)-5-fluoro-1-(2-benzyloxyethyl)-1H-indole-2-carboxamide (Compound No. 84)

Compound 84 is prepared, according to a process similar to the method described in Example 6, from ethyl 5-fluoro-1-(2-benzyloxyethyl)-1H-indole-2-carboxylate, obtained in the preceding step, and 6-amino-2,3-dihydro-1H-pyrrolo[1,2-a]benzimidazole (Freedman et al., *J. Het. Chem.*, 1966, 3, (3), 257-259).

Mp=186-187° C.

$^1$H NMR (DMSO D$_6$), δ (ppm): 2.63 (m, 2H); 2.93 (m, 2H); 3.75 (m, 2H); 4.09 (m, 2H); 4.39 (s, 2H); 4.81 (m, 2H); 7.01-7.19 (m, 6H); 7.25 (s, 1H); 7.31-7.62 (m, 3H); 7.62 (dxd, 1H); 7.97 (m, 1H); 10.23 (s, 1H).

EXAMPLE 19

No. 82 of Table 2

N-(2,3-dihydro-1H-pyrrolo[1,2-a]benzimidazol-6-yl)-5-fluoro-1-{2-[(5-methylpyridin-2-yl)oxy]ethyl}-1H-indole-2-carboxamide

19.1 2-[(5-methylpyridin-2-yl)oxy]ethanol

A suspension of 0.291 ml (4.12 mmol) of 2-bromoethanol, of 0.3 g (2.75 mmol) of 2-hydroxy-5-methylpyridine and of 0.85 g (6.18 mmol) of potassium carbonate in 3 ml of dimethylformamide is vigorously stirred for 12 hours at reflux. The mixture is subsequently diluted with 100 ml of water and extracted with 100 ml of dichloromethane. The organic phase is washed with 50 ml of water, dried over sodium sulphate, concentrated under reduced pressure and then chromatographed on a silica column, elution being carried out with a mixture of hexane and ethyl acetate. The expected product is thus isolated.

$^1$H NMR (DMSO D$_6$), δ (ppm): 2.2 (s, 3H); 3.66-3.71 (m, 2H); 4.22 (t, 2H); 4.77 (t, 1H); 6.71 (d, 1H); 7.51 (dxd, 1H); 7.95 (dxd, 1H).

19.2 ethyl 5-fluoro-1-{2-[(5-methylpyridin-2-yl)oxy]ethyl}-1H-indole-2-carboxylate The ethyl 5-fluoro-1-[2-[(5-methylpyridin-2-yl)oxy]ethyl]-1H-indole-2-carboxylate intermediate is prepared in a manner similar to the method described in Example 18.1, from ethyl 5-fluoro-1H-indole-2-carboxylate and 2-(5-methylpyridin-2-yloxy)ethanol prepared in the preceding step.

19.3 N-(2,3-dihydro-1H-pyrrolo[1,2-a]benzimidazol-6-yl)-5-fluoro-1-{2-[(5-methylpyridin-2-yl)oxy]ethyl}-1H-indole-2-carboxamide (Compound No. 82)

Compound 82 is prepared according to a process similar to the method described in Example 6, from the compound obtained in the preceding step, and 6-amino-2,3-dihydro-1H-pyrrolo[1,2-a]benzimidazole (Freedman et al., *J. Het. Chem.*, 1966, 3, (3), 257-259).

Mp=209-210° C.

$^1$H NMR (DMSO D$_6$), δ (ppm): 2.11 (s, 3H); 2.61 (m, 2H); 2.91 (m, 2H); 4.09 (m, 2H); 4.49 (m, 2H); 4.91 (m, 2H); 6.41 (d, 1H); 7.11 (dxt, 1H); 7.21 (s, 1H); 7.32-7.56 (m, 4H); 7.62 (dxd, 1H); 7.89 (d, 1H); 7.97 (d, 1H); 10.29 (s, 1H).

EXAMPLE 20

No. 83 of Table 2

N-(2,3-dihydro-1H-pyrrolo[1,2-a]benzimidazol-6-yl)-5-fluoro-1-[2-{[(5-trifluoromethyl)pyridin-2-yl]oxy}ethyl]-1H-indole-2-carboxamide

20.1 2-[(5-trifluoromethyl)pyridin-2-yl)oxy]ethanol

The compound is prepared according to a method similar to that described in Example 19.1, from 2-bromoethanol and 2-hydroxy-5-(trifluoromethyl)pyridine.

20.2 ethyl 5-fluoro-1-[2-{[(5-trifluoromethyl)pyridin-2-yl]oxy}ethyl]-1H-indole-2-carboxylate This intermediate is prepared, in a manner similar to the method described in Example 18.1, from ethyl 5-fluoro-1H- indole-2-carboxylate and 2-[[5-(trifluoromethyl)pyridin-2-yl]oxy]ethanol prepared in the preceding step.

20.3 N-(2,3-dihydro-1H-pyrrolo[1,2-a]benzimidazol-6-yl)-5-fluoro-1-[2-{[(5-trifluoromethyl)pyridin-2-yl]oxy}-ethyl]-1H-indole-2-carboxamide (Compound No. 83)

Compound 83 is prepared, according to a process similar to the method described in Example 6, from ethyl 5-fluoro-1-[2-[[(5-trifluoromethyl)pyridin-2-yl]oxy]-ethyl]-1H-indole-2-carboxylate, obtained in the preceding step, and 6-amino-2,3-dihydro-1H-pyrrolo-[1,2-a]benzimidazole (Freedman et al., *J. Het. Chem.*, 1966, 3, (3), 257-259).
[MH]$^+$=524
$^1$H NMR (DMSO D$_6$), δ (ppm): 2.61 (m, 2H); 2.89 (m, 2H); 4.05 (m, 2H); 4.59 (m, 2H); 4.98 (m, 2H); 6.69 (d, 1H); 7.11 (dxt, 1H); 7.23 (s, 1H); 7.3-7.52 (m, 3H); 7.63 (dxd, 1H); 7.84 (dxd, 1H); 7.97 (s, 1H); 8.45 (s, 1H); 10.28 (s, 1H).

EXAMPLE 21

No. 127 of Table 2

N-(3,4-dihydro-1H-oxazino[1,4][4,3-a]benzimidazol-7-yl)-1-benzyl-5-fluoro-1H-pyrrolo[2,3-b]pyridine-2-carboxamide 21.1 2-amino-3-iodo-5-fluoropyridine 5 g (44.6 mmol) of 2-amino-5-fluoropyridine, 13.9 g (44.6 mmol) of silver sulphate and 400 ml of ethanol are introduced into a 500 ml two-necked flask equipped with a magnetic stirrer. 11.31 g (44.6 mmol) of powdered iodine are subsequently added in small portions. The stirring is continued at ambient temperature for 24 hours. The insoluble material is removed by filtration and washed with ethanol and the filtrate is concentrated under reduced pressure. The residue thus obtained is taken up in a mixture of ethyl acetate (200 ml) and of a solution of sodium carbonate (200 ml). After separation, the organic phase is washed successively with a 25% aqueous solution of sodium thiosulphate and then with a saturated aqueous solution of sodium chloride, and then dried over sodium sulphate and concentrated under reduced pressure. The resulting solid is purified by silica column chromatography, elution being carried out with a mixture of n-heptane and ethyl acetate. 2.67 g (11.22 mmol) of the expected product are obtained.
$^1$H NMR (DMSO D$_6$), δ (ppm): 7.95 (s, 1H); 7.85 (s, 1H); 5.9 (s, NH$_2$).

21.2 5-fluoro-1H-pyrrolo[2,3-b]pyridine-2-carboxylic acid 0.5 g (2.10 mmol) of 2-amino-3-iodo-5-fluoropyridine obtained in step 5.1, 0.55 g (6.3 mmol) of pyruvic acid, 0.71 g (6.3 mmol) of 1,4-diazabicyclo[2.2.2]octane (DABCO) and 15 ml of anhydrous dimethylformamide are introduced into a 25 ml sealed tube equipped with a magnetic stirrer and subjected to sparging with argon. After a few minutes, 0.05 g (0.22 mmol) of palladium acetate is added. The reaction mixture is kept stirring and subjected to sparging with argon for 20 minutes and then rapidly sealed and brought to 100° C. for 2 h 30. The cooled solution is concentrated under reduced pressure. The residue is subsequently taken up with ethyl acetate (100 ml) and water (75 ml). The organic phase is washed with water and then extracted with twice 50 ml of a 2N aqueous solution of sodium hydroxide. The basic aqueous phases are combined, cooled to 0° C. and then acidified by adding hydrochloric acid (pH 3). The medium is extracted with ethyl acetate (4×50 ml), and the combined organic phases are dried over sodium sulphate and then concentrated under reduced pressure. 0.158 g (0.88 mmol) of the expected product is obtained in the form of a yellow powder.
$^1$H NMR (DMSO D$_6$), δ (ppm): 13.2 (s, 1H); 12.4 (s, 1H); 8.4 (d, 1H); 7.95 (dd, 1H); 7.1 (d, 1H).

21.3 ethyl 5-fluoro-1H-pyrrolo[2,3-b]pyridine-2-carboxylate 0.2 g (1.11 mmol) of acid obtained in step 21.2 and 10 ml of ethanol are introduced into a 100 ml round-bottomed flask equipped with a magnetic stirrer. 1 ml of concentrated sulphuric acid is added to the reaction mixture, which is subsequently brought to reflux for 18 hours. The cooled solution is concentrated to dryness under reduced pressure. The residue is taken up with ethyl acetate (50 ml) and the product is washed successively with a normal aqueous solution of sodium hydroxide (2×10 ml), with water (10 ml) and then with a saturated aqueous solution of sodium chloride. The organic phase is dried over sodium sulphate and then concentrated under reduced pressure. 0.21 g of the expected product is isolated.
$^1$H NMR (DMSO D$_6$), δ (ppm): 12.6 (s, NH); 8.4 (d, 1H); 8.0 (dd, 1H); 7.1 (d, 1H); 4.35 (q, 2H); 1.35 (t, 3H).

21.4 ethyl 1-benzyl-5-fluoro-1H-pyrrolo[2,3-b]-pyridine-2-carboxylate

The ethyl 1-benzyl-5-fluoro-1H-pyrrolo[2,3-b]pyridine-2-carboxylate was prepared according to a method similar to that described in Example 4.1, from benzyl alcohol and the ethyl 5-fluoro-1H-pyrrolo[2,3-b]pyridine-2-carboxylate prepared in the preceding step.
Mp=74-75° C.

21.5 N-(3,4-dihydro-1H-oxazino[1,4][4,3-a]-benzimidazol-7-yl)-1-benzyl-5-fluoro-1H-pyrrolo[2,3-b]-pyridine-2-carboxamide (Compound No. 127)

Compound No. 127 is prepared, according to a method similar to that described in Example 4.2, from ethyl 1-benzyl-5-fluoro-1H-pyrrolo[2,3-b]pyridine-2-carboxylate, described in the preceding step, and 7-aminomorpholino[4,3-a]benzimidazole (Mullock, E. B., *J. Chem. Soc. Section C*, 1970, (6), 829-833).
Mp=231-232° C.
$^1$H NMR (DMSO D$_6$), δ (ppm): 4.15 (m, 4H); 4.91 (s, 2H); 5.9 (s, 2H); 7.02-7.26 (m, 5H); 7.35 (s, 1H); 7.5 (m, 2H); 8.01 (s, 1H); 8.12 (dxd, 1H); 8.46 (m, 1H); 10.44 (s, 1H).

EXAMPLE 22

Compound No. 128 of Table No. 2

N-(2,3-dihydro-1H-pyrrolo[1,2-a]benzimidazol-6-yl)-1-benzyl-5-fluoro-1H-pyrrolo[2,3-b]pyridine-2-carboxamide Compound No. 128 is prepared, according to a method similar to that described in Example 4.2, from ethyl 1-benzyl-5-fluoro-1H-pyrrolo[2,3-b]pyridine-2-carboxylate, described in Example 21.4, and 6-amino-2,3-dihydro-1H-pyrrolo[1,2-a]benzimidazole (Freedman et al., *J. Het. Chem.*, 1966, 3, (3), 257-259).

Mp=259-260° C.

$^1$H NMR (DMSO D$_6$), δ (ppm): 2.59 (m, 2H); 2.89 (t, 2H); 4.05 (t, 2H); 5.89 (s, 2H); 7.01-7.24 (m, 5H); 7.35 (m, 2H); 7.45 (dxd, 1H); 7.91 (s, 1H); 8.1 (dxd, 1H); 8.41 (m, 1H); 10.41 (s, 1H).

EXAMPLE 23

Compound No. 129 of Table No. 2

N-(2,3-dihydro-1H-pyrrolo[1,2-a]benzimidazol-6-yl)-1-benzyl-5-trifluoromethyl-1H-pyrrolo[3,2-b]pyridine-2-carboxamide 23.1 3-amino-2-iodo-6-(trifluoromethyl)pyridine 1.56 g (6.17 mmol) of iodine are added, portionwise, to a mixture, stirred under argon at 20° C., of 1 g (6.17 mmol) of 3-amino-6-(trifluoromethyl)pyridine and 1.25 g (6.17 mmol) of silver sulphate in 40 ml of ethanol. The stirring is maintained for 18 hours. The insoluble material is removed by filtration and is washed with ethanol, the filtrate is concentrated under reduced pressure, and the residue is taken up in 100 ml of dichloromethane. The organic phase is washed successively with 20 ml of a 5% aqueous solution of sodium hydroxide, 40 ml of water and 20 ml of a saturated aqueous solution of sodium chloride, dried over sodium sulphate, concentrated under reduced pressure and then purified by silica column chromatography (eluents: heptane-ethyl acetate). 1.17 g of the expected product are thus isolated, which product is used as it is in the subsequent synthesis.

23.2 5-trifluoromethylpyrrolo[3,2-b]pyridine-2-carboxylic acid 0.5 g (1.74 mmol) of 3-amino-2-iodo-6-(trifluoro-methyl)pyridine, obtained in step 23.1, 0.45 g (5.21 mmol) of pyruvic acid, 0.51 ml (5.21 mmol) of 1,4-diazabicyclo[2.2.2]octane and 10 ml of dry dimethylformamide are introduced, under argon, into a sealed tube. The solution is degassed for a few minutes and then 0.19 g (0.87 mmol) of palladium acetate is added, the tube is sealed and the whole is brought to reflux at 130° C. for 4 hours. The cooled solution is subsequently concentrated under reduced pressure and the residue is taken up with 100 ml of ethyl acetate. The organic phase is extracted successively with twice 50 ml of a 2N aqueous solution of sodium hydroxide. The basic aqueous phases are combined, cooled to 0° C., acidified by adding hydrochloric acid, and then extracted with 4 times 50 ml of ethyl acetate. These organic phases are combined, washed with 20 ml of a saturated aqueous solution of sodium chloride, dried over sodium sulphate and then concentrated under reduced pressure. 0.22 g of product is obtained, which product is used as it is in the subsequent step.

23.3 ethyl 5-(trifluoromethyl)pyrrolo[3,2-b]pyridine-2-carboxylate 1 ml (18.71 mmol) of concentrated sulphuric acid is added to a solution of 0.2 g (0.87 mmol) of 5-trifluoromethyl-1H-pyrrolo[3,2-b]pyridine-2-carboxylic acid, obtained in step 23.2, in 10 ml of ethanol. The solution is stirred at reflux for 20 hours and then cooled and concentrated under reduced pressure. The resultant residue is subsequently taken up with 50 ml of dichloromethane and then washed successively with 20 ml of a saturated aqueous solution of sodium hydrogen carbonate, 40 ml of water and 20 ml of a saturated aqueous solution of sodium chloride, dried over sodium sulphate and then concentrated under reduced pressure. 0.19 g of product is obtained, which product is used as it is in the subsequent step.

23.4 ethyl 1-benzyl-5-trifluoromethylpyrrolo[3,2-b]-pyridine-2-carboxylate

Ethyl 1-benzyl-5-trifluoromethyl-1H-pyrrolo[3,2-b]-pyridine-2-carboxylate was prepared, according to a method similar to that described in Example 4.1, from benzyl alcohol and the compound prepared in the preceding step.

23.5 N-(2,3-dihydro-1H-pyrrolo[1,2-a]benzimidazol-6-yl)-1-benzyl-5-trifluoromethyl-1H-pyrrolo[3,2-b]pyridine-2-carboxamide (Compound No. 129)

Compound No. 129 is prepared, according to a method similar to that described in Example 4.2, from ethyl 1-benzyl-5-trifluoromethyl-1H-pyrrolo[3,2-b]pyridine-2-carboxylate, described in the preceding step, and 6-amino-2,3-dihydro-1H-pyrrolo[1,2-a]benzimidazole (Freedman et al., *J. Het. Chem.*, 1966, 3, (3), 257-259).

Mp=251-252° C.

$^1$H NMR (DMSO D$_6$), δ (ppm): 2.61 (m, 2H); 2.91 (t, 2H); 4.09 (t, 2H); 5.92 (s, 2H); 7.05-7.29 (m, 5H); 7.31-7.5 (m, 2H); 7.56 (s, 1H); 7.7 (d, 1H); 7.91 (s, 1H); 8.29 (d, 1H); 10.51 (s, 1H).

EXAMPLE 24

Compound No. 130 of Table No. 2

N-(2,3-dihydro-1H-pyrrolo[1,2-a]benzimidazol-6-yl)-1-[(pyridin-4-yl)methyl]-5-fluoro-1H-pyrrolo[2,3-b]-pyridine-2-carboxamide 24.1 ethyl 1-[(pyridin-4-yl)methyl]-5-fluoro-1H-pyrrolo[2,3-b]pyridine-2-carboxylate 9.18 g (36.02 mmol) of 1,1'-(azodicarbonyl)dipiperidine are added, in a quarter of an hour, to a solution, stirred at 20° C., of 5 g (24.02 mmol) of ethyl 5-fluoro-1H-pyrrolo[2,3-b]pyridine-2-carboxylate (Example 21.3), 3.97 g (36.02 mmol) of (pyridin-4-yl)methanol and 7.5 g (36.02 mmol) of tributylphosphine in 150 ml of toluene. The reaction mixture is stirred at 20° C. for 16 hours, filtered over a celite buffer, concentrated under reduced pressure and then taken up in 100 ml of dichloromethane. The organic solution is washed twice with 50 ml of a 5% aqueous solution of potassium carbonate and then once with 50 ml of water, dried over sodium sulphate and concentrated under reduced pressure. The product obtained is chromatographed on a silica column, elution being carried out with a mixture of heptane and ethyl acetate. 4.5 g of the expected ester are thus isolated.

Mp=120-121° C.

24.2 N-(2,3-dihydro-1H-pyrrolo[1,2-a]benzimidazol-6-yl)-1-[(pyridin-4-yl)methyl]-5-fluoro-1H-pyrrolo-[2,3-b]pyridine-2-carboxamide (Compound No. 130)

Compound No. 130 is prepared, according to a method similar to that described in Example 1.2, from ethyl 1-[(pyridin-4-yl)methyl]-5-fluoro-1H-pyrrolo[2,3-b]-pyridine-2- carboxylate, described in the preceding step, and 6-amino-2,3-dihydro-1H-pyrrolo[1,2-a]benzimidazole (Freedman et al., *J. Het. Chem.*, 1966, 3, (3), 257-259).

Mp=283-285° C.

$^1$H NMR (DMSO D$_6$), δ (ppm): 2.62 (m, 2H); 2.92 (t, 2H); 4.09 (t, 2H); 5.93 (s, 2H); 7.01 (d, 2H); 7.38 (d, 1H); 7.49 (m, 2H); 7.95 (s, 1H); 8.2 (d, 1H); 8.45 (m, 3H); 10.42 (s, 1H).

EXAMPLE 25

Compound No. 131 of Table No. 2

N-(2,3-dihydro-1H-pyrrolo[1,2-a]benzimidazol-6-yl)-1-[(pyridin-4-yl)methyl]-5-trifluoromethyl-1H-pyrrolo[3,2-b]pyridine-2-carboxamide 25.1 ethyl 1-[(pyridin-4-yl)methyl]-5-trifluoromethyl-1H-pyrrolo[3,2-b]pyridine-2-carboxylate According to a process similar to that described in Example 24.1, using 5 g (18.4 mmol) of ethyl 5-tri-fluoromethyl-1H-pyrrolo[3,2-b]pyridine-2-carboxylate (Example 23.3) and 3.04 g (27.6 mmol) of (pyridin-4-yl)methanol, 4.2 g of the expected compound are isolated. Mp=130-131° C.

25.2 N-(2,3-dihydro-1H-pyrrolo[1,2-a]benzimidazol-6-yl)-1-[(pyridin-4-yl)methyl]-5-trifluoromethyl-1H-pyrrolo[3,2-b]pyridine-2-carboxamide (Compound No. 131)

According to a process similar to that described in Example 24.2, using 0.3 g (0.86 mmol) of compound obtained in the preceding step and 0.178 g (1.03 mmol) of 6-amino-2,3-dihydro-1H-pyrrolo[1,2-a]benzimidazole (Freedman et al., *J. Het. Chem.*, 1966, 3, (3), 257-259), 0.25 g of the expected compound is isolated in the form of a white solid.

Mp=270-271° C.

$^1$H NMR (DMSO D$_6$), δ (ppm): 2.61 (m, 2H); 2.92 (t, 2H); 4.09 (t, 2H); 5.99 (s, 2H); 7.01 (d, 2H); 7.43 (m, 2H); 7.71 (s, 1H); 7.79 (d, 1H); 7.95 (s, 1H); 8.25 (d, 1H); 8.43 (d, 2H); 10.51 (s, 1H).

EXAMPLE 26

Compound No. 132 of Table No. 2

N-(4-methyl-1,2,3,4-tetrahydropyrimido[1,2-a]-benzimidazol-7-yl)-5-fluoro-1-(3-fluorobenzyl)-1H-indole-2-carboxamide hydrochloride (1:1)

Compound 132 is prepared, according to a process similar to that of Example 11.2, from 0.312 g (1.09 mmol) of 5-fluoro-1-(3-fluorobenzyl)-1H-indole-2-carboxylic acid and 0.22 g (1.09 mmol) of 7-amino-4-methyl-1,2,3,4-tetrahydropyrimido[1,2-a]benzimidazole (VII-m). 0.41 g of the expected product is isolated in the form of a pale yellow solid. The compound is taken up in 50 ml of a 0.1N solution of hydrochloric acid in isopropanol. The solution obtained is concentrated under reduced pressure and compound 139 is thus isolated in the form of a hydrochloride.

Mp (HCl 1:1)=343-349° C.
$^1$H NMR (DMSO D$_6$), δ (ppm):

EXAMPLE 27

Compound No. 24 of Table No. 2

N-(3,4-dihydro-1H-oxazino[1,4][4,3-a]benzimidazol-7-yl)-1-benzyl-5-trifluoromethyl-1H-pyrrolo[2,3-b]pyridine-2-carboxamide Compound 24 was prepared, according to a method similar to that described in Example 4.2, by reaction between ethyl 1-benzyl-5-trifluoromethyl-1H-pyrrolo[2,3-b]-pyridine-2-carboxylate, described in Example 4.1, and 7-aminooxazino[1,4][4,3-a]benzimidazole (Mullock, E. B., *J. Chem. Soc. Section C*, 1970, (6), 829-833).

Mp=236-237° C.

$^1$H NMR (DMSO D$_6$), δ (ppm): 4.12 (m, 4H); 4.91 (s, 2H); 5.95 (s, 2H); 7.02-7.28 (m, 5H); 7.5 (m, 3H); 8.01 (d, 1H); 8.68 (d, 1H); 8.78 (d, 1H); 10.55 (s, 1H).

EXAMPLE 28

Compound No. 15 of Table No. 2

N-(3,4-dihydro-1H-oxazino[1,4][4,3-a]benzimidazol-7-yl)-5-fluoro-1-(3-fluorobenzyl)-1H-indole-2-carboxamide Compound 15 was prepared, according to a method similar to that described in Example 6, by reaction between ethyl 5-fluoro-1-(3-fluorobenzyl)-1H-indole-2-carboxylate, obtained in step 2.1, and 7-aminooxazino[1,4][4,3-a]benzimidazole (Mullock, E. B., *J. Chem. Soc. Section C*, 1970, (6), 829-833).

Mp=216-217° C.

$^1$H NMR (DMSO D$_6$), δ (ppm): 4.15 (m, 4H); 4.91 (s, 2H); 5.85 (s, 2H); 6.82-7.61 (m, 10H); 8 (s, 1H); 10.39 (s, 1H).

EXAMPLE 29

Compound No. 133 of Table No. 2

N-[2,3-dihydro-3-(tert-butoxycarbonyl)imidazo[1,2-a]-benzimidazol-6-yl]-1-benzyl-5-trifluoromethyl-1H-pyrrolo[3,2-b]pyridine-2-carboxamide Compound 133 is prepared, according to a process described in Example 11, from 6-amino-2,3-dihydro-1-tert-butoxycarbonylimidazo[1,2-a]benzimidazole (VII-d) and ethyl 1-benzyl-5-trifluoromethylpyrrolo[3,2-b]pyridine-2-carboxylate (23.4).

Mp=169-174° C.

$^1$H NMR (DMSO D$_6$), δ (ppm): 1.51 (s, 9H); 4.27 (m, 4H); 5.94 (s, 2H); 7.09-7.31 (m, 6H); 7.42 (dxd, 1H); 7.58 (s, 1H); 7.71 (d, 1H); 7.84 (s, 1H); 8.29 (d, 1H); 10.52 (s, 1H).

EXAMPLE 30

Compound No. 137 of Table No. 2

N-(2,3-dihydroimidazo[1,2-a]benzimidazol-6-yl)-1-benzyl-5-trifluoromethyl-1H-pyrrolo[3,2-b]pyridine-2-carboxamide A solution of 0.18 g (0.31 mmol) of compound 133 (Example 29) in 10 ml of 2M hydrochloric acid in diethyl ether is stirred at 20° C. for 16 hours. After this period of time, the expected product 137 is isolated by filtering off a yellow precipitate which is dried under reduced pressure.

$^1$H NMR (DMSO D$_6$), δ (ppm): 4.3 (m, 4H); 5.98 (s, 2H); 7.11 (m, 1H); 7.25 (m, 3H); 7.41 (d, 1H); 7.59 (dxd, 1H); 7.68 (s, 1H); 7.78 (d, 1H); 7.89 (s, 1H); 8.35 (d, 1H); 9.39 (s, 1H); 10.82 (s, 1H); 13.35 (s, 1H).

The following tables 2, 3 and 4 illustrate the chemical structures and the physical properties of some examples of compounds according to the invention.

In these tables:
- the column "G1" represents an atom or group of atoms reading from left to right;
- the column "MP (° C.) or [MH]$^+$" gives the melting points of the products in degrees Celsius (° C.) or else the peak obtained by mass spectrometry, after chemical ionization;
- in the column "Salt/base", "-" represents a compound in free base form, whereas "HCl" represents a compound in hydrochloride form and the ratio in brackets is the (acid:base) ratio;
- "CH$_3$" corresponds to a methyl group, "CF$_3$" corresponds to a trifluoromethyl group, "Et" corresponds to an ethyl group, "t-Bu" corresponds to a tert-butyl group, "i-Pr" corresponds to an isopropyl group, and "benzyl" corresponds to a phenylmethyl group.

TABLE 2

| No. | X$_1$,X$_2$,X$_3$,X$_4$ | R' | G$_1$ | Salt/Base | Mp(° C.) or [MH]$^+$ |
|---|---|---|---|---|---|
| 1. | CH, C—F, CH, CH | (pyridin-4-yl)methyl | (CH$_2$)$_2$ | — | 292-293 |
| 2. | CH, C—F, CH, CH | 3-fluorobenzyl | (CH$_2$)$_2$ | — | 286-287 |
| 3. | CH, CH, CH, N | benzyl | (CH$_2$)$_2$ | — | 233-235 |
| 4. | CH, C—CF$_3$, CH, N | benzyl | (CH$_2$)$_2$ | — | 241-243 |
| 5. | CH, C—F, CH, CH | (pyridin-4-yl)methyl | CH$_2$ | — | 266-267 |
| 6. | CH, C—F, CH, CH | 3-fluorobenzyl | CH$_2$ | — | 256-257 |
| 7. | CH, CH, CH, N | benzyl | CH$_2$ | — | 251-252 |
| 8. | CH, C—CF$_3$, CH, N | benzyl | CH$_2$ | — | 268-270 |
| 9. | CH, C—F, CH, CH | 2-(pyridin-3-yl)ethyl | CH$_2$ | — | 251-252 |
| 10. | CH, C—F, CH, CH | H | CH$_2$ | — | 350-352 |
| 11. | CH, C—F, CH, CH | 4,5-dimethylpyridin-2-yl | CH$_2$ | — | 254-255 |
| 12. | CH, C—F, CH, CH | 3-fluorobenzyl | NH | — | [MH]$^+$ = 444 |
| 13. | CH, C—F, CH, CH | Methyl | CH$_2$ | — | 269-270 |
| 14. | CH, C—CF$_3$, CH, N | H | CH$_2$ | — | 380-385 |
| 15. | CH, C—F, CH, CH | 3-fluorobenzyl | CH$_2$O | — | 218-217 |
| 16. | CH, C—F, CH. CH | (thiazol-2-yl)methyl | CH$_2$ | — | 248-249 |
| 17. | CH, C—F, CH, CH | 3-fluorobenzyl | CHOH | — | 260-263 |
| 18. | CH, C—F, CH, CH | (3-methylpyridin-2-yl)methyl | CH$_2$ | — | 247-248 |
| 19. | CH, C—F, CH, CH | 3-fluorobenzyl | S | — | 246-247 |
| 20. | CH, C—F, CH, CH | (pyridin-4-yl)methyl | CH$_2$O | — | 283-284 |
| 21. | CH, C—F, CH, CH | (5-methylpyridin-2-yl)methyl | CH$_2$ | — | 257-280 |
| 22. | CH, C—F, CH, CH | (6-methylpyridin-2-yl)methyl | CH$_2$ | — | 277-279 |
| 23. | CH, C—F, CH, CH | (pyrimidin-4-yl)methyl | CH$_2$ | — | 236-241 |
| 24. | CH, C—CF$_3$, CH, N | benzyl | CH$_2$O | — | 236-237 |
| 25. | CH, C—F, CH, CH | 3-fluorobenzyl | CH$_2$NH | HCl 1:1 | 276-284 |
| 26. | CH, C—F, CH, CH | 3-fluorobenzyl | NCH$_3$ | — | 281-282 |
| 27. | CH, C-tBu, CH, CH | (pyridin-4-yl)methyl | CH$_2$ | — | 273-274 |
| 28. | C—OCH$_3$, CH, CH, C—CH$_3$ | (pyridin-4-yl)methyl | CH$_2$ | — | 304-305 |
| 29. | CH, CH, C—N(CH$_3$)$_2$, CH | (pyridin-4-yl)methyl | CH$_2$ | — | 282-283 |
| 30. | CH, CH, C—CF$_3$, CH | (pyridin-4-yl)methyl | CH$_2$ | — | 284-285 |
| 31. | C—Br, CH, CH, CH | (pyridin-4-yl)methyl | CH$_2$ | — | 304-305 |
| 32. | CH, CH, C-tBu, CH | (pyridin-4-yl)methyl | CH$_2$ | — | 241-242 |
| 33. | CH, CCl, CH, CH | (pyridin-4-yl)methyl | CH$_2$ | — | [MH]$^+$ 442 |
| 34. | C—CH$_3$, CH, C—CH$_3$, CH | (pyridin-4-yl)methyl | CH$_2$ | — | 291-292 |
| 35. | CH, CH, CH, CH | (pyridin-4-yl)methyl | CH$_2$ | — | 290-291 |
| 36. | C—CH$_3$, CH, C—H, CH | (pyridin-4-yl)methyl | CH$_2$ | — | 310-311 |
| 37. | CH, CH, C—SCH$_3$, CH | (pyridin-4-yl)methyl | CH$_2$ | — | 263-264 |
| 38. | CH, CH, C-iPr, CH | (pyridin-4-yl)methyl | CH$_2$ | — | 262-263 |
| 39. | CH, CH, C-Et, CH | (pyridin-4-yl)methyl | CH$_2$ | — | 255-256 |
| 40. | CH, CH, CBr, CH | (pyridin-4-yl)methyl | CH$_2$ | — | 298-299 |
| 41. | CH, C—NO$_2$, CH, CH | (pyridin-4-yl)methyl | CH$_2$ | — | [MH]$^+$ 453 |
| 42. | C—CH$_3$, CH, CH, C—CH$_3$ | (pyridin-4-yl)methyl | CH$_2$ | — | 308-309 |

TABLE 2-continued

| No. | $X_1, X_2, X_3, X_4$ | R' | $G_1$ | Salt/Base | Mp(° C.) or $[MH]^+$ |
|---|---|---|---|---|---|
| 43. | CH, C—SO$_2$CH$_3$, CH, CH | (pyridin-4-yl)methyl | CH$_2$ | — | $[MH]^+$ 486 |
| 44. | C—F, CH, CH, CH | (pyridin-4-yl)methyl | CH$_2$ | — | 275-276 |
| 45. | CH, CH, C-OiPr, CH | (pyridin-4-yl)methyl | CH$_2$ | — | 257-258 |
| 46. | CH, CH, C—CH$_3$, CH | (pyridin-4-yl)methyl | CH$_2$ | — | 302-303 |
| 47. | C—CH$_3$, CH, C—OCH$_3$, C—CH$_3$ | (pyridin-4-yl)methyl | CH$_2$ | — | 311-312 |
| 48. | CH, CH, CH, C-iPr | (pyridin-4-yl)methyl | CH$_2$ | — | 210-211 |
| 49. | CH, C—CF$_3$, CH, N | 3-fluorobenzyl | CH$_2$ | — | 253-254 |
| 50. | CH, C—CF$_3$, CH, N | (quinolin-2-yl)methyl | CH$_2$ | — | 300-301 |
| 51. | CH, C—CF$_3$, CH, N | (quinoxalin-2-yl)methyl | CH$_2$ | — | $[MH]^+$ 528 |
| 52. | CH, C—CF$_3$, CH, N | (5-trifluoromethylfuran-2-yl)methyl | CH$_2$ | — | $[MH]^+$ 534 |
| 53. | CH, C—CF$_3$, CH, N | 3-(dimethylamino)benzyl | CH$_2$ | — | $[MH]^+$ 519 |
| 54. | CH, C—CF$_3$, CH, N | (pyridin-3-yl)methyl | CH$_2$ | — | $[MH]^+$ 477 |
| 55. | CH, C—CF$_3$, CH, N | (pyridin-2-yl)methyl | CH$_2$ | — | $[MH]^+$ 477 |
| 56. | CH, C—CF$_3$, CH, N | (6-methylpyridin-2-yl)methyl | CH$_2$ | — | $[MH]^+$ 491 |
| 57. | CH, C—CF$_3$, CH, N | (2-methylpyridin-3-yl)methyl | CH$_2$ | — | $[MH]^+$ 491 |
| 58. | CH, C—CF$_3$, CH, N | (2-methylpyridin-4-yl)methyl | CH$_2$ | — | 275-276 |
| 59. | CH, C—CF$_3$, CH, N | (6-trifluoromethylpyridin-3-yl)methyl | CH$_2$ | — | $[MH]^+$ 545 |
| 60. | CH, C—CF$_3$, CH, N | (pyrazin-2-yl)methyl | CH$_2$ | — | $[MH]^+$ 478 |
| 61. | CH, C—CF$_3$, CH, N | (5-methylpyrazin-2-yl)methyl | CH$_2$ | — | 316-317 |
| 62. | CH, C—CF$_3$, CH, N | (thiazol-2-yl)methyl | CH$_2$ | — | $[MH]^+$ 483 |
| 63. | CH, C—CF$_3$, CH, N | (benzothiazol-2-yl)methyl | CH$_2$ | — | 307-308 |
| 64. | CH, C—CF$_3$, CH, N | [2-(morpholin-1-yl)-pyridin-3-yl]methyl | CH$_2$ | — | $[MH]^+$ 562 |
| 65. | CH, C—CF$_3$, CH, N | 2-(diethylaminocarbonyl)methyl | CH$_2$ | — | 276-277 |
| 66. | CH, C—F, CH, CH | 3-(dimethylamino)benzyl | CH$_2$ | — | 292-293 |
| 67. | CH, C—F, CH, CH | 2-fluorobenzyl | CH$_2$ | — | 250-251 |
| 68. | CH, C—F, CH, CH | 4-fluorobenzyl | CH$_2$ | — | 218-219 |
| 69. | CH, C—F, CH, CH | 4-(imidazol-1-yl)benzyl | CH$_2$ | — | $[MH]^+$ 491 |
| 70. | CH, C—F, CH, CH | benzyl | CH$_2$ | — | 232-233 |
| 71. | CH, C—F, CH, CH | (6-trifluoromethylpyridin-3-yl)methyl | CH$_2$ | — | 251-252 |
| 72. | CH, C—F, CH, CH | (2-methylpyridin-3-yl)methyl | CH$_2$ | — | 291-292 |
| 73. | CH, C—F, CH, CH | (pyridin-2-yl)ethyl | CH$_2$ | — | 180-181 |
| 74. | CH, C—F, CH, CH | (pyridin-4-yl)ethyl | CH$_2$ | — | $[MH]^+$ 440 |
| 75. | CH, C—F, CH, CH | (pyridin-3-yl)propyl | CH$_2$ | — | 208-209 |
| 76. | CH, C—F, CH, CH | (pyridin-4-yl)propyl | CH$_2$ | — | $[MH]^+$ 454 |
| 77. | CH, C—F, CH, CH | (pyridin-2-yl)propyl | CH$_2$ | — | 170-171 |
| 78. | CH, C—F, CH, CH | (6-methylpyridin-2-yl)propyl | CH$_2$ | — | $[MH]^+$ 468 |
| 79. | CH, C—F, CH, CH | [2-(4-methylphenylthio)-pyridin-3-yl]methyl | CH$_2$ | — | $[MH]^+$ 548 |
| 80. | CH, C—F, CH, CH | (quinolin-3-yl)methyl | CH$_2$ | — | $[MH]^+$ 476 |
| 81. | CH, C—F, CH, CH | 3-fluorobenzyl | CH$_2$N(CH$_3$) | — | $[MH]^+$ 472 |
| 82. | CH, C—F, CH, CH | 2-[5-methylpyridin-2-yloxy]ethyl | CH$_2$ | — | 209-210 |
| 83. | CH, C—F, CH, CH | 2-[(5-trifluoromethyl)-pyridin-2-yloxy]ethyl | CH$_2$ | — | $[MH]^+$ 524 |
| 84. | CH, C—F, CH, CH | 2-(benzyloxy)ethyl | CH$_2$ | — | 186-187 |
| 85. | CH, CH, CH, N | 3-methoxybenzyl | CH$_2$ | — | 407-408 |
| 86. | CH, CH, CH, N | 2-fluorobenzyl | CH$_2$ | — | $[MH]^+$ 426 |
| 87. | CH, CH, CH, N | 4-fluorobenzyl | CH$_2$ | — | 350-351 |
| 88. | CH, CH, CH, N | 3-chlorobenzyl | CH$_2$ | — | $[MH]^+$ 442 |
| 89. | CH, CH, CH, N | 3-methylbenzyl | CH$_2$ | — | 211-212 |
| 90. | CH, CH, CH, N | (naphth-1-yl)methyl | CH$_2$ | — | $[MH]^+$ 458 |
| 91. | CH, CH, CH, N | 2-(3-trifluoromethyl-phenyl)ethyl | CH$_2$ | — | 281-282 |
| 92. | CH, CH, CH, N | 2-(2-trifluoromethyl-phenyl)ethyl | CH$_2$ | — | 230-231 |
| 93. | CH, CH, CH, N | 2-(3-fluorophenyl)ethyl | CH$_2$ | — | $[MH]^+$ 440 |
| 94. | CH, CH, CH, N | 2-(4-fluorophenyl)ethyl | CH$_2$ | — | 233-234 |
| 95. | CH, CH, CH, N | 3-phenylpropyl | CH$_2$ | — | $[MH]^+$ 436 |

TABLE 2-continued

| No. | $X_1, X_2, X_3, X_4$ | R' | $G_1$ | Salt/Base | Mp(° C.) or $[MH]^+$ |
|---|---|---|---|---|---|
| 96. | CH, CH, CH, N | (pyridin-3-yl)methyl | $CH_2$ | — | $[MH]^+$ 409 |
| 97. | CH, CH, CH, N | (4-methyl-2-phenylpyrimidin-5-yl)methyl | $CH_2$ | — | $[MH]^+$ 500 |
| 98. | CH, CH, CH, N | (pyridin-2-yl)methyl | $CH_2$ | — | 265-266 |
| 99. | CH, CH, CH, N | (6-methylpyridin-2-yl)methyl | $CH_2$ | — | 262-263 |
| 100. | CH, CH, CH, N | (2-methylpyridin-4-yl)methyl | $CH_2$ | — | 263-264 |
| 101. | CH, CH, CH, N | (2-methylpyridin-3-yl)methyl | $CH_2$ | — | $[MH]^+$ 423 |
| 102. | CH, CH, CH, N | (6-trifluoromethylpyridin-3-yl)methyl | $CH_2$ | — | $[MH]^+$ 477 |
| 103 | CH, CH, CH, N | [6-(pyrrolidin-1-yl)pyridin-3- | $CH_2$ | — | $[MH]^+$ 478 |
| 104. | CH, CH, CH, N | [6-(N-diethylamino)pyridin-3-yl]methyl | $CH_2$ | — | 227-228 |
| 105. | CH, CH, CH, N | [2-(pyrrolidin-1-yl)pyridin-3-yl]methyl | $CH_2$ | — | $[MH]^+$ 478 |
| 106. | CH, CH, CH, N | [6-(morpholin-1-yl)pyridin-3-yl]methyl | $CH_2$ | — | 252-253 |
| 107. | CH, CH, CH, N | 2-(pyridin-2-yl)ethyl | $CH_2$ | — | $[MH]^+$ 423 |
| 108. | CH, CH, CH, N | 2-(pyridin-3-yl)ethyl | $CH_2$ | — | 408-409 |
| 109. | CH, CH, CH, N | 2-(pyridin-4-yl)ethyl | $CH_2$ | — | $[MH]^+$ 423 |
| 110. | CH, CH, CH, N | 3-(pyridin-4-yl)propyl | $CH_2$ | — | $[MH]^+$ 437 |
| 111. | CH, CH, CH, N | 3-(pyridin-3-yl)propyl | $CH_2$ | — | 217-218 |
| 112. | CH, CH, CH, N | 3-(6-methylpyridin-2-yl)propyl | $CH_2$ | — | 182-183 |
| 113. | CH, CH, CH, N | (quinolin-2-yl)methyl | $CH_2$ | — | 254-255 |
| 114. | CH, CH, CH, N | (quinolin-3-yl)methyl | $CH_2$ | — | 275-276 |
| 115. | CH, CH, CH, N | (quinolin-4-yl)methyl | $CH_2$ | — | $[MH]^+$ 459 |
| 116. | CH, CH, CH, N | (3,5-dimethyl-4-methoxypyridin-2-yl)methyl | $CH_2$ | — | 275-276 |
| 117. | CH, CH, CH, N | (quinolin-6-yl)methyl | $CH_2$ | — | 286-287 |
| 118. | CH, CH, CH, N | 3-(N-dimethylamino)benzyl | $CH_2$ | — | 155-156 |
| 119. | CH, CH, CH, N | (quinoxalin-2-yl)methyl | $CH_2$ | — | 287-288 |
| 120. | CH, CH, CH, N | [2-(4-methylphenylthio)pyridin-3-yl]methyl | $CH_2$ | — | $[MH]^+$ 531 |
| 121. | CH, CH, CH, N | (pyrazin-2-yl)methyl | $CH_2$ | — | $[MH]^+$ 410 |
| 122. | CH, CH, CH, N | (5-methylpyrazin-2-yl)methyl | $CH_2$ | — | $[MH]^+$ 424 |
| 123. | CH, CH, CH, N | (benzothiazol-2-yl)methyl | $CH_2$ | — | $[MH]^+$ 465 |
| 124. | CH, CH, CH, N | (thiazol-2-yl)methyl | $CH_2$ | — | $[MH]^+$ 415 |
| 125. | CH, CH, CH, N | 2-(diethylaminocarbonyl)methyl | $CH_2$ | — | 271-272 |
| 126. | CH, CH, CH, N | (5-trifluoromethylfuran-2-yl)methyl | $CH_2$ | — | $[MH]^+$ 466 |
| 127. | CH, C—F, CH, N | benzyl | $CH_2O$ | — | 231-232 |
| 128. | CH, C—F, CH, N | benzyl | $CH_2$ | — | 259-260 |
| 129. | N, C—$CF_3$, CH, CH | benzyl | $CH_2$ | — | 251-252 |
| 130. | CH, C—F, CH, N | (pyridin-4-yl)methyl | $CH_2$ | — | 283-285 |
| 131. | N, C—$CF_3$, CH, CH | (pyridin-4-yl)methyl | $CH_2$ | — | 270-271 |
| 132. | CH, C—F, CH, CH | 3-fluorobenzyl | $N(CH_3)CH_2$ | HCl (1:1) | 343-349 |
| 133. | N, C—$CF_3$, CH, CH | benzyl | NC(O)OtBu | — | 169-174 |
| 134. | CH, C—F, CH, N | benzyl | NC(O)OtBu | — | 160-164 |
| 135. | CH, C—F, CH, N | (pyridin-4-yl)methyl | NC(O)OtBu | — | 303-308 |
| 136. | CH, C—F, CH, CH | 3-fluorobenzyl | NC(O)OtBu | — | $[MH]^+$ 544 |
| 137. | N, C—$CF_3$, CH, CH | benzyl | NH | HCl (2:1) | $[MH]^+$ 477 |
| 138. | CH, C—F, CH, N | benzyl | NH | HCl (1:1) | $[MH]^+$ 427 |
| 139. | CH, C—F, CH, N | (pyridin-4-yl)methyl | NH | — | $[MH]^+$ 428 |
| 140. | CH, C—$CF_3$, CH, N | benzyl | N(Me) | HCl (1:1) | 337-339 |
| 141. | CH, C—F, CH, N | benzyl | N(Me) | HCl (1:1) | 330-333 |
| 142. | CH, C—F, CH, N | (pyridin-4-yl)methyl | N(Me) | HCl (3:2) | 318-320 |
| 143. | CH, C—F, CH, <u>CH</u> | 3-fluorobenzyl | $N(Me)(CH_2)_2$ | HCl 1:1 | 325-331 |
| 144. | CH, C—$CF_3$, CH, N | benzyl | NH | HCl (1:1) | $[MH]^+$ 477 |

TABLE 2-continued

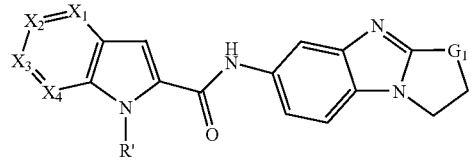

| No. | $X_1,X_2,X_3,X_4$ | R' | $G_1$ | Salt/Base | Mp(° C.) or [MH]$^+$ |
|---|---|---|---|---|---|
| 145. | CH, C—CF$_3$, CH, N | (pyridin-4-yl)methyl | CH$_2$ | — | 278-279 |
| 146. | CH, C—CF$_3$, CH, N | (pyridin-4-yl)methyl | CH$_2$O | — | 299-300 |
| 147. | CH, C—CF$_3$, CH, N | benzyl | NC(O)OtBu | — | [MH]$^+$ 577 |

The NMR data of some examples from the table are indicated hereinafter, by way of examples.

NMR for Compound No. 9: $^1$H NMR (DMSO D$_6$), δ (ppm): 2.68 (m, 2H); 2.98 (t, 2H); 3.04 (t, 2H); 4.11 (t, 2H); 4.82 (t, 2H); 7.1 (dxt, 1H); 7.2 (m, 1H); 7.3 (s, 1H); 7.49 (m, 5H); 8 (s, 1H); 8.3 (s, 1H); 8.32 (d, 1H); 10.11 (s, 1H).

NMR for Compound No. 10: $^1$H NMR (DMSO D$_6$), δ (ppm): 2.61 (m, 2H); 2.92 (t, 2H); 4.08 (t, 2H); 7.05 (dxt, 1H); 7.41 (m, 5H); 8.03 (s, 1H); 10.19 (s, 1H); 11.8 (s, 1H).

NMR for Compound No. 11: $^1$H NMR (DMSO D$_6$), δ (ppm): 2.32 (s, 3H); 2.4 (s, 3H); 2.61 (m, 2H); 2.8 (t, 2H); 4.06 (t, 2H); 7.11 (m, 3H); 7.41 (m, 5H); 7.89 (s, 1H); 10.4 (s, 1H).

NMR for Compound No. 12: $^1$H NMR (DMSO D$_6$), δ (ppm): 4.27 (m, 4H); 5.88 (s, 2H); 6.89 (m, 2H); 7.02 (txd, 1H); 7.14 (txd, 1H); 7.31 (m, 2H); 7.42 (s, 1H); 7.59 (m, 3H); 7.99 (s, 1H); 9.39 (s, 1H); 10.61 (s, 1H);

NMR for Compound No. 13: $^1$H NMR (DMSO D$_6$), δ (ppm): 2.61 (m, 2H); 2.91 (t, 2H); 4.03 (s, 3H); 4.1 (t, 2H); 7.11 (dxt, 1H); 7.25 (s, 1H); 7.48 (m, 4H); 8.1 (s, 1H); 10.25 (s, 1H);

NMR for Compound No. 14: $^1$H NMR (DMSO D$_6$), δ (ppm): 2.61 (m, 2H); 2.90 (t, 2H); 4.08 (t, 2H); 7.4 (m, 3H); 8.01 (s, 1H); 8.6 (d, 2H); 10.3 (s, 1H); 12.78 (s, 1H);

NMR for Compound No. 17: $^1$H NMR (DMSO D$_6$), δ (ppm): 2.39 (m, 1H); 2.89 (m, 1H); 4.02 (m, 1H); 4.18 (m, 1H); 5.07 (m, 1H); 5.85 (s, 2H); 6.8 (m, 2H); 6.97-7.32 (m, 3H); 7.34-7.6 (m, 5H); 8.02 (s, 1H).

NMR for Compound No. 18: $^1$H NMR (DMSO D$_6$), δ (ppm): 2.4 (s, 3H); 2.59 (m, 2H); 2.9 (t, 2H); 4.05 (t, 2H); 5.95 (s, 2H); 6.92-7.11 (m, 2H); 7.27-7.58 (m, 6H); 7.89 (d, 1H); 8.02 (d, 1H); 10.09 (s, 1H).

NMR for Compound No. 49: $^1$H NMR (DMSO D$_6$), δ (ppm): 2.66 (m, 2H); 2.95 (dxd, 2H); 4.11 (dxd, 2H); 6 (s, 2H); 6.93 (m, 2H); 7.05 (dxt, 1H); 7.3-7.5 (m, 3H); 7.59 (s, 1H); 7.95 (d, 1H); 8.71 (d, 1H); 8.81 (d, 1H); 10.55 (s, 1H).

NMR for Compound No. 136: $^1$H NMR (DMSO D$_6$), δ (ppm): 1.51 (s, 9H); 4.27 (m, 4H); 5.92 (s, 2H); 7.09-7.3 (m, 6H); 7.41 (dxd, 1H); 7.61 (s, 1H); 7.85 (s, 1H); 8.66 (s, 1H); 8.79 (s, 1H); 10.45 (s, 1H).

NMR for Compound No. 138: $^1$H NMR (DMSO D$_6$), δ (ppm): 4.3 (m, 4H); 5.92 (s, 2H); 7.1 (m, 2H); 7.21 (m, 3H); 7.39 (d, 1H); 7.41 (s, 1H); 7.58 (d, 1H); 7.99 (s, 1H); 8.17 (dxd, 1H); 8.49 (s, 1H); 9.3 (s, 1H); 10.62 (s, 1H).

NMR for Compound No. 139: $^1$H NMR (DMSO D$_6$), δ (ppm): 4.03 (m, 4H); 5.92 (s, 2H); 6.92 (s, 1H); 7.05 (m, 3H); 7.23 (d, 1H); 7.46 (s, 1H); 7.56 (s, 1H); 8.19 (dxd, 1H); 8.41 (d, 3H); 10.32 (s, 1H).

NMR for Compound No. 143: $^1$H NMR (CDCL$_3$), δ (ppm): 2.25 (m, 4H); 3.41 (s, 3H); 3.49 (m, 2H); 4.24 (m, 2H); 6.15 (s, 2H); 7.01-7.37 (m, 6H); 7.41-7.65 (m, 3H); 7.79 (m, 2H); 8.25 (s, 1H).

NMR for Compound No. 144: $^1$H NMR (DMSO D$_6$), δ (ppm): 4.29 (m, 4H); 5.98 (s, 2H); 7.11 (m, 2H); 7.25 (m, 3H); 7.4 (d, 1H); 7.55 (d, 1H); 7.57 (s, 1H); 7.99 (s, 1H); 8.71 (s, 1H); 8.8 (s, 1H); 9.26 (s, 1H); 10.74 (s, 1H).

NMR for Compound No. 145: $^1$H NMR (DMSO D$_6$), δ (ppm): 2.61 (m, 2H); 2.92 (t, 2H); 4.09 (t, 2H); 5.98 (s, 2H); 7.01 (d, 2H); 7.41 (m, 2H); 7.62 (s, 1H); 7.9 (s, 1H); 8.39 (d, 2H); 8.71 (d, 2H); 10.55 (s, 1H).

NMR for Compound No. 146: $^1$H NMR (DMSO D$_6$), δ (ppm): 4.19 (m, 4H); 4.95 (s, 2H); 6 (s, 2H); 7.05 (m, 2H); 7.51 (m, 2H); 7.66 (s, 1H); 7.99 (s, 1H); 8.44 (d, 2H); 8.78 (d, 2H).

TABLE 3

| No. | X | Y | R' | Salt/Base | Mp (° C.) |
|---|---|---|---|---|---|
| 148. | CH | CH | 3-fluorobenzyl | — | 261-262 |
| 149. | CH | CH | (pyridin-4-yl)methyl | — | 277-278 |
| 150. | N | CH | 3-fluorobenzyl | — | 295-298 |
| 151. | CH | N | 3-fluorobenzyl | HCl 1:1 | 225-230 |

TABLE 4

| No. | R' | $G_2$ | $G_3$ | Salt/Base | Mp (° C.) or [MH]$^+$ |
|---|---|---|---|---|---|
| 152. | (pyridin-4-yl)methyl | CH$_2$ | CH(CH$_3$) | HCl 1:1 | 285-290 |
| 153. | (pyridin-4-yl)methyl | CHOH | CH$_2$ | HCl 1:1 | 295-300 |
| 154. | 3-fluorobenzyl | CHOCH$_3$ | CH$_2$ | HCl 1:1 | 220-225 |

The NMR data of some examples from the table are indicated hereinafter, by way of examples:

NMR for Compound No. 152: $^1$H NMR (DMSO D$_6$), δ (ppm): 1.59 (d, 3H); 2.38 (m, 1H); 2.94 (m, 1H); 3.33 (m, 2H); 4.87 (m, 1H); 6.5 (s, 2H); 7.2 (dxt, 1H); 7.36 (d, 2H); 7.5-7.7 (m, 3H); 7.84 (m, 2H); 8.35 (s, 1H); 8.65 (d, 2H).

NMR for Compound No. 153: $^1$H NMR (DMSO D$_6$), δ (ppm): 3.11 (d, 1H); 3.62 (dxd, 1H); 4.2 (dxd, 1H); 4.49 (dxd, 1H); 5.1 (m, 1H); 6.09 (s, 2H); 7.19 (dxt, 1H); 7.43 (d, 2H); 7.5-7.7 (m, 3H); 7.81 (d, 2H); 8.32 (s, 1H); 8.7 (d, 2H); 10.7 (s, 1H).

The compounds according to the invention were the subject of in vitro and in vivo pharmacological assays which demonstrated their advantage as substances with therapeutic activities. These compounds have an antagonist or agonist activity with respect to TRPV1 (or VR1) receptors.

Test for Inhibition of the Current Induced by Capsaicin on Rat DRGs

Primary Culture of Rat Dorsal Root Ganglion (DRG) Cells:

The neurons of the DRG naturally express the TRPV1 receptor.

Newborn rat DRG primary cultures are prepared from 1-day-old rat pups. Briefly, after dissection, the ganglia are trypsinized and the cells are mechanically dissociated by controlled trituration. The cells are resuspended in an Eagle's basal culture medium containing 10% of fetal calf serum, 25 mM KCl, 2 mM glutamine, 100 µg/ml gentamicin and 50 ng/ml of NGF, and then deposited onto laminin-coated glass cover slips (0.25×10$^6$ cells per cover slip) which are then placed in 12-well Corning dishes. The cells are incubated at 37° C. in a humidified atmosphere containing 5% CO$_2$ and 95% air. Cytosine β-D-arabinoside (1 µM) is added 48 h after placing in culture, in order to prevent the development of non-neuronal cells. The cover slips are transferred into the experimental chambers for the patch-clamp studies after 7-10 days of culture.

Electrophysiology:

The measuring chambers (volume 800 µl) containing the cell preparation are placed on the platform of an inverted microscope (Olympus IMT2) equipped with Hoffman optics (Modulation Contrast, New York), and observed at the magnification of ×400. The chambers are continually perfused by gravity (2.5 ml/min) by means of a solution distributing device with 8 inlets, and the sole outlet of which, consisting of a polyethylene tube (500 µm aperture), is placed less than 3 mm from the cell studied. The "whole cell" configuration of the patch-clamp technique was used. The borosilicate glass pipettes (resistance 5-10 MOhms) are moved close to the cell by means of a 3D piezoelectric micromanipulator (Burleigh, PC1000). The overall currents (membrane potential fixed at −60 mV) are recorded with an Axopatch 1D amplifier (Axon Instruments, Foster City, Calif.), connected to a PC controlled by Pclamp8 software (Axon Instrument). The current traces are recorded on paper and simultaneously digitized (sampling frequency 15 to 25 Hz) and acquired on the hard drive of the PC.

The application of a 300 nM solution of capsaicin causes, on the DRG cells (voltage fixed at −70 mV), an inward cationic current. In order to minimize desensitization of the receptors, a minimum period of one minute is observed between two applications of capsaicin. After a controlled period (stabilization of the capsaicin response alone), the compounds of the invention to be tested are applied alone at a given concentration (concentration of 10 nM or of 1 nM) for a period of 4 to 5 minutes, during which several capsaicin+ compound tests are carried out (obtaining of maximum inhibition). The results are expressed as % inhibition of the control capsaicin response.

In the case of the VR1 antagonist compounds, the percentages of inhibition of the capsaicin response (1 microM) are between 20% and 100% for the most active compounds of the invention tested at concentrations of 0.1 to 10 nM. These are therefore effective antagonists of TRPV1-type receptors. Table 5 gives some examples of the % inhibition obtained with the compounds of the invention.

TABLE 5

| Compound No. | % inhibition in DRG patch |
|---|---|
| 1 | 37% (10 nM) |
| 5 | 53% (10 nM) |

The actual agonist effect of the compounds can be evaluated by measuring the current induced at various concentrations of compound on the rat DRG, in the presence or absence of capsazepine.

Mouse Corneal Irritation Test

The irritant nature of capsaicin can be readily assessed at the level of the cornea since this organ is one of the most innervated by C fibers. In this context, according to the preliminary experiments, the application of a very small amount of capsaicin (2 µl at a concentration of 160 µM) to the surface of the cornea of an animal results in a certain number of stereotyped behaviors associated with the irritation and that can be readily listed. Among these are: blinking of the eye, rubbing of the eye instilled with the ipsilateral forelimb, rubbing of the face with both forelimbs, scratching of the ipsilateral face with the hind limb. The duration of these behaviors does not exceed the 2 minutes of observation and the animal then returns to its normal activity. Its appearance is, moreover, also normal. The mouse is not hidden away in a corner with its coat bristling and does not develop any observable sign of sufferance. It can be concluded from this that the duration of action of capsaicin at these doses is less than 2 minutes.

Summary of the Methodology:

The principle of the series of experiments is to determine whether the compounds of the invention can influence the behavioral response induced by a given amount of capsaicin. The capsaicin is initially diluted to 25 mM in DMSO and diluted, for its final use, in physiological saline with 10% Tween 80. It appears, based on control studies, that, under these conditions, the solvent has no effect.

In practice, the product to be tested, prepared at 25 mM in DMSO and diluted for its final use in physiological saline with 10% Tween 80, at the highest concentration of 500 µM, is administered by local application to the surface of the cornea in a volume of 2 µl, 10 minutes before the application of the capsaicin. The animal receives the ocular instillation of 2 µl of a solution of capsaicin at 160 µm prepared as indicated above. Over the course of a period of observation of 2 minutes following the instillation, the number of times the instilled eye is rubbed by the ipsilateral forelimb is counted for each animal.

For a given group, the percentage protection is calculated as follows:

$P$=100−((average number of scratches of the group treated with the compound/average number of scratches of the group treated with the solvent)× 100).

This percentage protection is averaged for each group of animals (n=number of animals tested with the compound of the invention).

The protection percentages evaluated, in this model, for the most active compounds of the invention, used at the concentration of 500 μM, are between 20% and 100% (see example in Table 6):

TABLE 6

| Compound No. | % P 500 μM |
|---|---|
| 8 | 71% |
| 15 | 56% |
| 26 | 46% |

The results of these assays show that the most active compounds of the invention block, in vivo, the effects induced by the stimulation of TRPV1 receptors.

The compounds of the invention can therefore be used for the preparation of medicaments, in particular for the preparation of a medicament for preventing or treating pathologies in which TRPV1-type receptors are involved.

The compounds of the invention can be used for preventing or treating pathologies in which TRPV1-type receptors are involved.

Thus, a subject of the invention is medicaments which comprise at least one compound of formula (I), or a pharmaceutically acceptable salt, or else a hydrate or a solvate of said compound.

These medicaments can be used in therapeutics, in particular in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscle pain, trapped nerves (central and/or peripheral), spinal column and/or brain trauma, ischaemia (of the spinal column and/or of the brain), neurodegeneration, hemorrhagic strokes (of the spinal column and/or of the brain) and post-stroke pain.

The compounds of the invention can also be used for preventing and/or treating metabolic disorders such as diabetes.

The compounds of the invention can also be used for preventing and/or treating urological disorders such as bladder hyperactivity, bladder hyperreflexia, bladder instability, incontinence, urgent urination, urinary incontinence, cystitis, nephritic colic, pelvic hyper-sensitivity and pelvic pain.

The compounds of the invention can be used for preventing and/or treating gynecological disorders such as vulvodynia and pain associated with salpingitis or with dysmenorrhea.

These products can also be used for preventing and/or treating gastrointestinal disorders such as gastro-oesophageal reflex disorder, stomach ulcers, duodenal ulcers, functional dyspepsia, colitis, IBS, Crohn's disease, pancreatitis, oesophagitis and biliary colic. Similarly, the products of the present invention can be used in the prevention and/or treatment of respiratory disorders such as asthma, coughing, chronic obstructive pulmonary disease (COPD), bronchoconstriction and inflammatory disorders.

These products can also be used for preventing and/or treating psoriasis, pruritus, dermal, ocular or mucosal irritations, herpes and shingles.

The compounds of the invention can also be used for treating depression.

The compounds of the invention can also be used for treating central nervous system diseases such as multiple sclerosis.

According to another of its aspects, the present invention relates to pharmaceutical compositions comprising, as active ingredient, at least one compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected according to the pharmaceutical form and the desired method of administration, from the usual excipients known to those skilled in the art.

The pharmaceutical compositions of the present invention can be administered orally, sublingually, subcutaneously, intramuscularly, intravenously, topically, locally, intratracheally, intranasally, transdermally or rectally. These compositions can be administered in unit form, as a mixture with conventional pharmaceutical excipients. They are intended to be administered to animals and to human beings for the prophylaxis or treatment of the disorders or diseases mentioned above.

The appropriate unit administration forms include oral forms such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

Said unit forms are dosed so as to allow a daily administration of from 0.001 to 30 mg of active ingredient per kg of body weight, according to the galenical form.

There may be specific cases where higher or lower dosages are appropriate; such dosages do not depart from the scope of the invention. According to the usual practice, the dosage that is appropriate for each patient is determined by the physician according to the method of administration and the weight and the response of said patient.

The compounds of the invention can also be used for the preparation of medicaments, in particular for the preparation of a medicament for use in preventing or treating pathologies in which TRPV1-type receptors are involved, as mentioned above.

According to another of its aspects, the present invention also relates to a method for treating the pathologies indicated above, which comprises the administration, to a patient, of an effective dose of at least one compound according to the invention, or a pharmaceutically acceptable salt, a hydrate or a solvate thereof.

What is claimed is:

1. A compound of the formula (I):

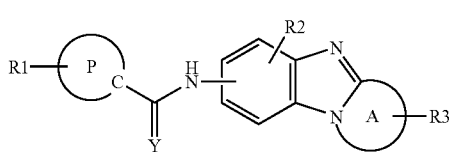

in which:

A is, with the C—N bond of the benzimidazole unit with which it is fused, a 4- to 7-membered monocyclic heterocycle or monocyclic heteroaryl, containing from one to three heteroatoms selected from O, S and N, including the nitrogen atom of the benzimidazole unit;

P is an 8-, 9-, 10- or 11-membered bicyclic heterocycle or bicyclic heteroaryl, containing from 1 to 6 heteroatoms selected from N, O and S; P being linked to the —C(Y)— group by a carbon atom;

with the proviso that, when A is a 7-membered saturated heterocycle, P is other than the 2,3-dihydro-1,4-benzodioxane group, the 1-benzopyran-2-one group and the isoindole group;

R1 is substituted on P one to four times and each R1 may be identical or different, R1 selected from a hydrogen atom, a halogen atom, and an oxo, thio, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylenethio-$C_1$-$C_6$-alkyl, heteroaryl-$C_1$-$C_3$-alkylenethio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)NR$_4$R$_5$, nitro, NR$_4$R$_5$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, SO$_2$NR$_4$R$_5$, SF$_5$, NR$_6$C(O)R$_7$, NR$_6$SO$_2$R$_8$, R$_4$R$_5$NC(O)—$C_1$-$C_3$-alkylene, aryl, heteroaryl, aryl-$C_1$-$C_5$-alkylene, heteroaryl-$C_1$-$C_5$-alkylene, aryloxy, arylthio, heteroaryloxy or heteroarylthio group;

said heteroaryl or aryl groups of R1 being optionally substituted with one or more substituents R$_9$, which may be identical to or different from one another;

with the proviso that, when R1 is attached to a nitrogen atom of P, then R1 is not a halogen atom, an oxo, thio, cyano, nitro, SF$_5$, NR$_4$R$_5$, $C_1$-$C_6$-thioalkyl, thioaryl, thioheteroaryl, $C_1$-$C_6$-alkoxy, aryloxy, heteroaryloxy, —NR$_6$COR$_7$ or NR$_6$SO$_2$R$_8$ group;

Y is an oxygen or sulphur atom;

R2 is a hydrogen atom, a halogen atom, or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl or $C_1$-$C_6$-alkoxy group;

R3 is substituted on a carbon atom of A, each R3 may be substituted 1 to 3 times on a carbon atom of A, each R3 substituted on a carbon atom of A may be identical or different, said R3 substituted on a carbon atom of A selected from hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy and $C_3$-$C_7$-cycloalkyl-$C_1$-$C_3$-alkylenoxy group;

or

R3 is substituted on a nitrogen atom of A, each R3 may be substituted once or twice on a nitrogen atom of A and may be identical or different, said R3 substituted on a nitrogen atom of A selected from hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O)$_2$—, $C_1$-$C_6$-alkyl-S(O)$_2$—, $C_1$-$C_6$-fluoro-alkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)— or heteroaryl-O—C(O)— group;

R$_4$ and R$_5$ are, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl group;

or R$_4$ and R$_5$ form, together with the nitrogen atom which carries them, an azetidine, pyrrolidine, piperidine, azepine, morpholine, thiomorpholine, piperazine or homopiperazine group, the NR$_4$R$_5$ group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_1$-$C_6$-fluoroalkyl, aryloxy-$C_1$-$C_6$-alkylene, aryloxy, heteroaryloxy-$C_1$-$C_6$-alkylene or heteroaryloxy group;

R$_6$ and R$_7$ are, independently of one another, a hydrogen atom, or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

or R$_6$ and R$_7$ together form a 4- to 7-membered lactam comprising the nitrogen atom and the C(O) group which carry them;

R$_8$ is a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

or R$_6$ and R$_8$ together form a 4- to 7-membered sultam comprising the nitrogen atom and the S(O)$_2$ group which carry them;

R$_9$ is a halogen atom, or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano, NR$_4$R$_5$, R$_4$R$_5$N—$C_1$-$C_3$-alkylene, aryl, heteroaryl, aryloxy, arylthio, heteroaryloxy or heteroarylthio group, said heteroaryl or aryl groups being optionally substituted with one or more substituents selected from a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano, NR$_4$R$_5$ or R$_4$R$_5$N—$C_1$-$C_3$-alkylene group;

the sulphur atom(s) of the heterocycle A may be in oxidized form (S(O) or S(O)$_2$);

the nitrogen atom(s) may be in oxidized form (N-oxide);

or an addition salt thereof; and with the proviso that 2-(2-chlorophenyl)-1,3-dioxo-N-(7,8,9,10-tetrahydro-6H-azepino[1,2-a]benzimidazol-3-yl)isoindoline-5-carboxamide is excluded.

2. The compound according to claim 1, which is of formula (II):

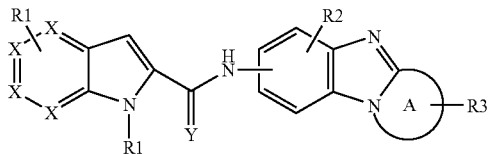

in which:

X is a carbon atom or a nitrogen atom; said X being identical to or different from one another and the number of X=N not being greater than 2;

R2, R3, Y and A being as defined in formula (I) according to claim 1;

and each R1 maybe the same or different and is defined as in Formula I according to claim 1; or an addition salt thereof.

3. The compound according to claim 2, which is of formula (III):

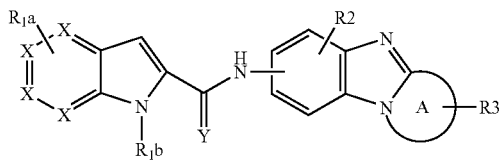

in which:

$R_{1a}$ is bonded to the ring containing X atoms one or more times, each $R_{1a}$ may be identical or different, each $R_{1a}$ is selected from hydrogen, a halogen a $C_1$-$C_6$-alkyl, $C_1$-$C_6$-fluoroalkyl, $C_1$-$C_6$-alkoxy, $C_1$-$C_6$-thioalkyl, $C_1$-$C_6$-alkyl-S(O)$_2$—, NR$_4$R$_5$ and nitro group;

$R_{1b}$ is a hydrogen atom, or a $C_1$-$C_6$-alkyl, heteroaryloxy-$C_1$-$C_6$-alkyl, aryl-$C_1$-$C_3$-alkylenoxy-$C_1$-$C_6$-alkyl, R$_4$R$_5$NC(O)—$C_1$-$C_3$-alkylene, aryl, heteroaryl, aryl-$C_1$-$C_3$-alkylene or heteroaryl-$C_1$-$C_6$-alkylene group;

said heteroaryl or aryl groups of $R_{1b}$ being optionally substituted with one or more substituents R$_9$, which may be identical to or different from one another;

R$_9$ is a halogen atom or a $C_1$-$C_6$-alkyl, $C_1$-$C_6$-alkoxy, $C_1$-$C_6$-fluoroalkyl, aryl, heteroaryl, NR$_4$R$_5$ or arylthio group, said heteroaryl or aryl groups being optionally substituted with one or more substituents selected from a halogen atom, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro, cyano or R$_4$R$_5$N—$C_1$-$C_3$-alkylene group;

R2, R3, R$_4$, R$_5$, A, X and Y are as defined in formula (II) according to claim 2;

or an addition salt thereof.

4. The compound according to claim 1, which is of formula (IV):

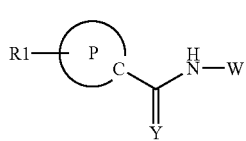

in which W is a tricyclic heterocycle or a tricyclic heteroaryl selected from:

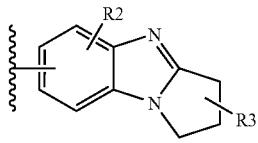

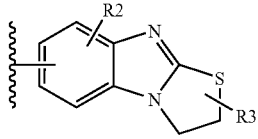

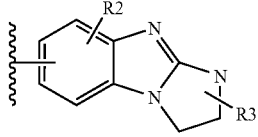

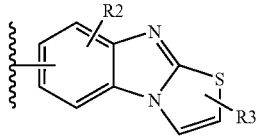

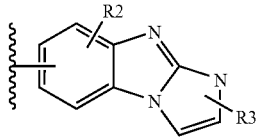

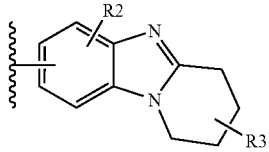

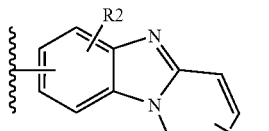

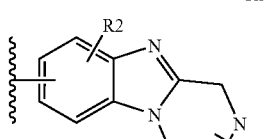

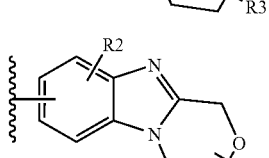

-continued

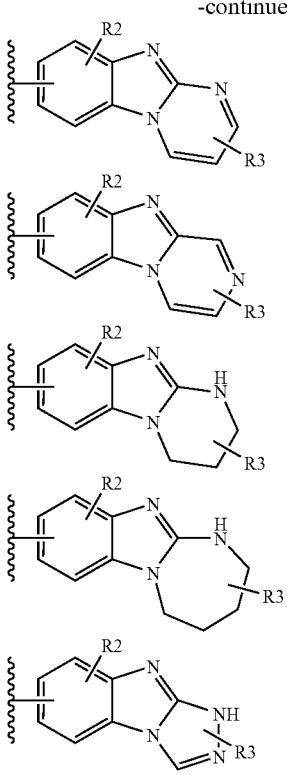

and wherein:
R1, R2, R3, P and Y being as defined in formula (I) according to claim 1;
or an addition salt thereof.

5. The compound according to claim 1, which is of formula (V):

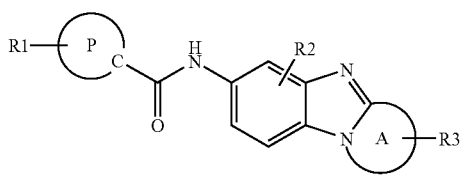
(V)

in which:
R1, R2, R3, A and P are as defined in formula (I) according to claim 1;
or an addition salt thereof.

6. The compound according to claim 1, which is of formula (V):

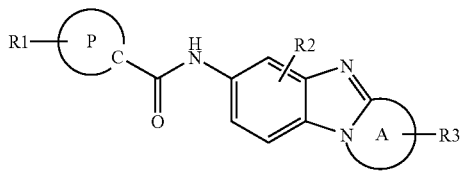
(V)

in which:
R2 is a hydrogen atom, or a $C_1$-$C_6$-alkyl or $C_1$-$C_6$-alkoxy group;

R3 is substituted on a carbon atom of A one to three times, each R3 substituted on a carbon atom of A may be identical or different, and is selected from hydrogen, $C_1$-$C_6$-alkyl, $C_1$-$C_6$-alkoxy and hydroxyl group;
or
R3 is substituted on a nitrogen atom of A, one to two times, each R3 substituted on a nitrogen atom of A may be identical or different, and is selected from hydrogen, $C_1$-$C_6$-alkyl, $C_1$-$C_6$-alkyl-O—C(O)— and aryl-$C_1$-$C_3$-alkyl-O—C(O)— group; and wherein
R1, A and P are as defined in formula (I) according to claim 1;
or an addition salt thereof.

7. The compound according to claim 1, which is of formula (V):

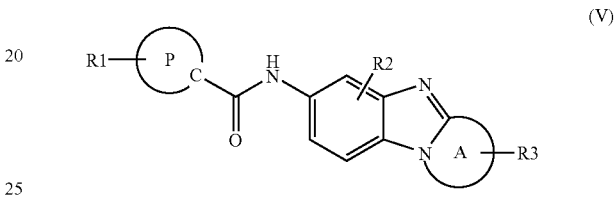
(V)

in which:
A is, with the C—N bond of the benzimidazole unit with which it is fused, a 5- to 7-membered monocyclic heterocycle or monocyclic heteroaryl containing from one to three heteroatoms selected from O, S and N, including the nitrogen atom of the benzimidazole unit; and wherein
$R_1$, $R_2$, $R_3$, and P are as defined in formula (I) according to claim 1;
or an addition salt thereof.

8. The compound according to claim 1, which is of formula (Va):

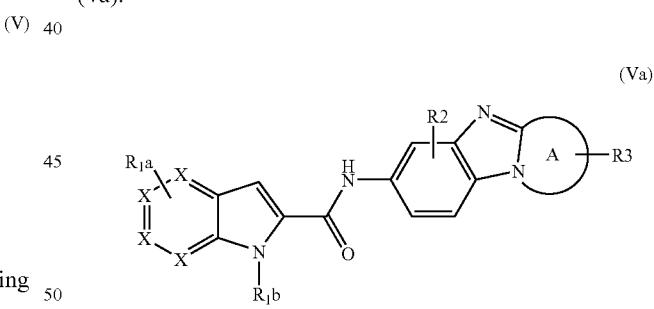
(Va)

in which
A is, with the C—N bond of the benzimidazole unit with which it is fused, a 5- to 7-membered monocyclic heterocycle or monocyclic heteroaryl containing one or two heteroatoms selected from O, S and N, including the nitrogen atom of the benzimidazole unit;
X is a carbon atom or a nitrogen atom; said X being identical to or different from one another and the number of X=N not being greater than 1;
$R_{1a}$ is one or more atoms or groups, which may be identical or different, selected from a hydrogen atom, a halogen atom or a $C_1$-$C_6$-alkyl group, a $C_1$-$C_6$-fluoroalkyl group, a $C_1$-$C_6$-alkoxy group, a $C_1$-$C_6$-thioalkyl group, a $C_1$-$C_6$-alkyl-S(O)$_2$— group, an $NR_4R_5$ group or a nitro group;

$R_{1b}$ is a hydrogen atom, or a $C_1$-$C_6$-alkyl, heteroaryloxy-$C_1$-$C_6$-alkyl, aryl-$C_1$-$C_3$-alkylenoxy-$C_1$-$C_6$-alkyl, $R_4R_5NC(O)$—$C_1$-$C_3$-alkylene, aryl, heteroaryl, aryl-$C_1$-$C_6$-alkylene or heteroaryl-$C_1$-$C_6$-alkylene group;

said heteroaryl or aryl groups of $R_{1b}$ being optionally substituted with one or more substituents $R_9$, which may be identical to or different from one another;

R2 is a hydrogen atom;

R3 is substituted on a carbon atom of X, and selected from hydrogen, $C_1$-$C_6$-alkyl, 6 $C_1$-$C_6$-alkoxy, and hydroxyl; or R3 is substituted on a nitrogen atom of X, and is selected from hydrogen, a $C_1$-$C_6$-alkyl group and a $C_1$-$C_6$-alkyl-O—C(O)— group;

$R_4$ and $R_5$ are, independently of one another, a $C_1$-$C_6$-alkyl group;

or $R_4$ and $R_5$ form, together with the nitrogen atom which carries them, a pyrrolidine or morpholine group; and $R_9$ is a halogen atom or a $C_1$-$C_6$-alkyl, $C_1$-$C_6$-alkoxy, $C_1$-$C_6$-fluoroalkyl, aryl, heteroaryl, $NR_4R_5$, or arylthio group, said aryl groups being optionally substituted with one or more $C_1$-$C_6$-alkyl groups;

or an addition salt thereof.

9. A process for preparing a compound of formula (I) according to claim 1 comprising:

reacting a compound of formula (VI):

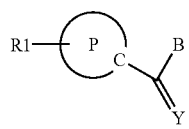

(VI)

in which P, R1 and Y are as defined in formula (I) according to claim 1 and B is a $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy group, with the resulting amide formed from the reaction of trimethyl-aluminum on the amine of formula VII:

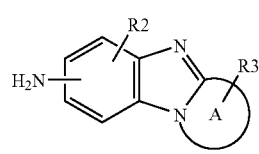

(VII)

in which A, R2 and R3 are as defined in formula (I) according to claim 1.

10. A process for preparing a compound of formula (I) according to claim 1 comprising:

converting a compound of formula (VI):

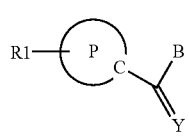

(VI)

in which P, R1 and Y are as defined in formula (I) according to claim 1 and B is a hydroxyl group, to an acid chloride by the action of thionyl chloride at the reflux of a solvent, and reacting the compound of formula (VI) obtained therefrom, in which P, R1 and Y are as defined in formula (I) according to claim 1 and B is a chlorine atom, in the presence of a base, with the compound of formula (VII):

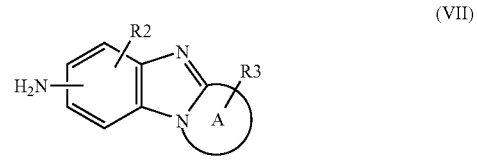

(VII)

in which A, R2 and R3 are as defined in formula (I) according to claim 1;

or subjecting to a coupling reaction a compound of formula (VI), in which P, R1 and Y are as defined in formula (I) according to claim 1 and B is a hydroxyl group, and a compound of formula (VII) in which A, R2 and R3 are as defined in formula (I) according to claim 1, in the presence of a coupling agent and a base in a solvent.

11. A compound of formula (VIIa), (VIIb), (VIIc), (VIId), (VIIe), (VIIf), (VIIg), (VIIh), (VIIi), (VIIj), (VIIk), (VIII), (VIIm) or (VIIn):

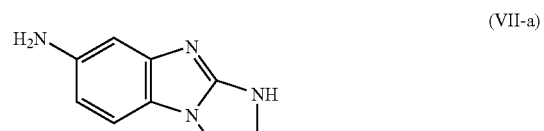

(VII-a)

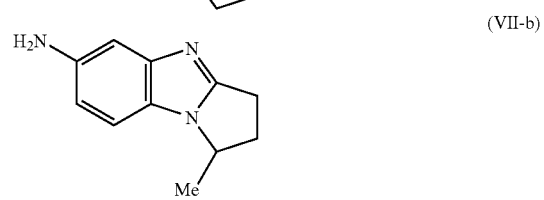

(VII-b)

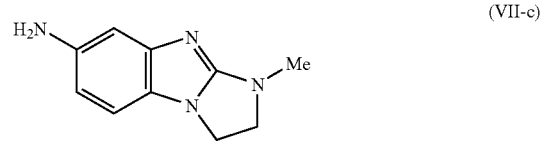

(VII-c)

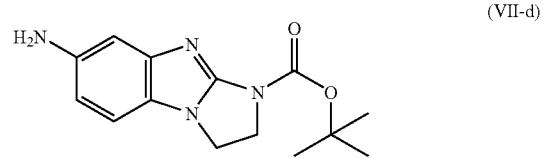

(VII-d)

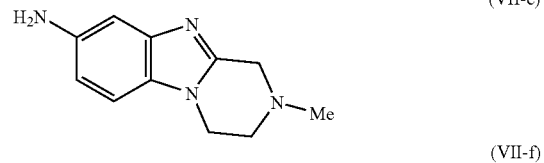

(VII-e)

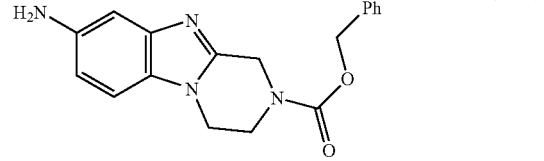

(VII-f)

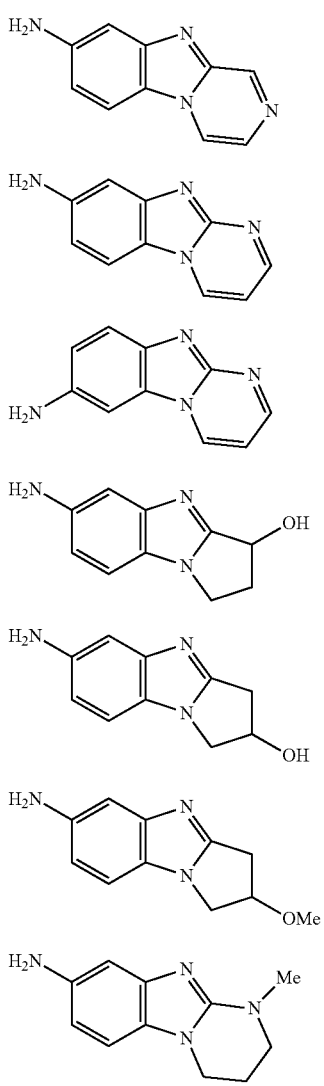

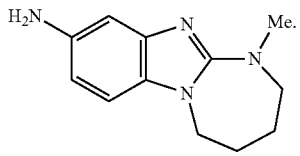

12. A pharmaceutical composition comprising at least one compound of formula (I) according to claim 1 or a pharmaceutically acceptable salt thereof in combination with at least one pharmaceutically acceptable excipient.

13. A pharmaceutical composition comprising at least one compound of formula (I) according to claim 2 or a pharmaceutically acceptable salt thereof in combination with at least one pharmaceutically acceptable excipient.

14. A pharmaceutical composition comprising at least one compound of formula (I) according to claim 3 or a pharmaceutically acceptable salt thereof in combination with at least one pharmaceutically acceptable excipient.

15. A pharmaceutical composition comprising at least one compound of formula (I) according to claim 4 or a pharmaceutically acceptable salt thereof in combination with at least one pharmaceutically acceptable excipient.

16. A pharmaceutical composition comprising at least one compound of formula (I) according to claim 5 or a pharmaceutically acceptable salt thereof in combination with at least one pharmaceutically acceptable excipient.

17. A pharmaceutical composition comprising at least one compound of formula (I) according to claim 6 or a pharmaceutically acceptable salt thereof in combination with at least one pharmaceutically acceptable excipient.

18. A pharmaceutical composition comprising at least one compound of formula (I) according to claim 7 or a pharmaceutically acceptable salt thereof in combination with at least one pharmaceutically acceptable excipient.

19. A pharmaceutical composition comprising at least one compound of formula (I) according to claim 8 or a pharmaceutically acceptable salt thereof in combination with at least one pharmaceutically acceptable excipient.

* * * * *